United States Patent [19]
Wöldike et al.

[11] Patent Number: 5,763,254
[45] Date of Patent: *Jun. 9, 1998

[54] ENZYME CAPABLE OF DEGRADING CELLULOSE OR HEMICELLULOSE

[75] Inventors: Helle Fabricius Wöldike, Lynge, Denmark; Fred Hagen, Seattle, Wash.; Carsten Mailand Hjort, Roskilde, Denmark; Sven Hastrup, Copenhagen, Denmark

[73] Assignee: Novo Nordisk A/S, Bagsvaerd, Denmark

[*] Notice: The term of this patent shall not extend beyond the expiration date of Pat. No. 5,457,046.

[21] Appl. No.: 483,432

[22] Filed: Jun. 7, 1995

Related U.S. Application Data

[63] Continuation of Ser. No. 361,920, Dec. 22, 1994, Pat. No. 5,457,046, which is a continuation of Ser. No. 940,860, filed as PCT/DK91/00124 May 8, 1991, abandoned.

[30] Foreign Application Priority Data

May 9, 1990 [DK] Denmark .................. 1158/90

[51] Int. Cl.$^6$ .................. C12N 9/42
[52] U.S. Cl. .................. 435/209
[58] Field of Search .................. 435/209

[56] References Cited

U.S. PATENT DOCUMENTS

| | | | |
|---|---|---|---|
| 4,435,307 | 3/1984 | Barbesgaard et al. | 252/174 |
| 5,457,046 | 10/1995 | Woldike et al. | 435/209 |

OTHER PUBLICATIONS

Tuula T. Teeri et al., Gene, vol. 51, pp. 43–52 (1987).
Rao et al., Chem. Abs. No. 110894p, vol. 105, p. 307 (1986).
Knowles et al., The Cellulase Genes of Trichoderma, pp. 335–340 (1987).
Azevedo et al., Nucleic Acids Research, vol. 18, No. 3, p. 668 (1990).
Kraulis et al., Biochemistry, vol. 28, pp. 7241–7257 (1989).
Sims et al., Gene, vol. 74, pp. 411–422 (1988).
Hayashida et al., Methods in Enzymology, vol. 160, pp. 323–332 (1988).
Hayashida et al., Chem. Abs. No. 207112c, vol. 109, p. 295 (1988).
Rodionova et al., Chem. Abs. No. 50208q, vol. 103, p. 237 (1985).
Hayashida et al., Chem. Abs. No. 20820g, vol. 105, p. 316 (1986).
Abuja et al., Biochem. Biophys. Research Comm., vol. 156, No. 1, pp. 180–185 (1988).
Ståhlberg et al., Eur. J. Biochem., vol. 173, pp. 179–183 (1988).
Knowles et al., Elsevier Publications, vol. 5, pp. 255–261 (1987).
Henrissat et al;. (1989) Comparison of *Trichoderma Cellulases* with Other Beta–Glycanases. In: *Trichoderma reesei* Cellulases: Biochemistry, Genetics, Physiology and Application. Kubisek, CP et al. (eds.) Royal Scoiety of Chemistry, Cambridge, UK, pp. 12–29.

*Primary Examiner*—Robert A. Wax
*Assistant Examiner*—Lisa J. Hobbs
*Attorney, Agent, or Firm*—Steve T. Zelson, Esq; Elias J. Lambiris, Esq

[57] ABSTRACT

The present invention relates to isolated and purified cellulose- or hemicellulose-degrading enzymes, comprising a catalytically active domain, a carbohydrate binding domain and a linking B region which operably links the catalytically active domain and the carbohydrate binding domain, wherein the carbohydrate binding domain has the following core sequence:

Xaa Xaa Gln Cys Gly Gly Xaa Xaa Xaa Xaa Gly Xaa Xaa Xaa Cys Xaa
 1   2   3   4   5   6   7   8   9  10  11  12  13  14  15  16

Xaa Xaa Xaa Xaa Cys Xaa Xaa Xaa Asn Xaa Xaa Tyr Xaa Gln Cys Xaa
17  18  19  20  21  22  23  24  25  26  27  28  29  30  31  32

Xaa
33  (SEQ ID NO:1), wherein the enzyme is endogenous to a strain of a fungus other than Trichoderma or Phanerochaete.

29 Claims, 22 Drawing Sheets

FIG. 11

```
agaccggaattcgcggccgccatctatccaacggtctagcttcacttcacaatgtatcgc
                                                         M Y R
atcgtcgcaaccgcctcggctcttattgccgctgctcgggctcaacaggtctgctctttg
I V A T A S A L I A A A R A Q Q V C S L
aacaccgagaccaagcctgccttgacctggtccaagtgtacatccagcggctgcagcgat
N T E T K P A L T W S K C T S S G C S D
gtcaagggctccgttgttattgatgccaactggcgatggactcaccagacttctgggtct
V K G S V V I D A N W R W T H Q T S G S
accaactgttacaccggaaacaagtgggacacctccatctgcactgatggcaagacctgc
T N C Y T G N K W D T S I C T D G K T C
GCCGAAAAGTGCTGTCTTGATGGCGCCGACTATTCTGGTACCTACGGAATCACCTCCAGC
A E K C C L D G A D Y S G T Y G I T S S
ggcaaccagctcagtcttggattcgtcaccaacggtccctacagcaagaacatcggcagc
G N Q L S L G F V T N G P Y S K N I G S
cgaacctacctcatggagaacgagaacaccatccagatgttccagcttctgggcaacgag
R T Y L M E N E N T Y Q M F Q L L G N E
ttcacctttgatgtcgatgtctctggtatcggctgcggtctgaacggtgcccctcacttc
F T F D V D V S G I G C G L N G A P H F
gtcagcatggacgaggatggtggcaaggccaagtactccggaaacaaggccggagccaag
V S M D E D G G K A K Y S G N K A G A K
tacggaactggcTActgtgATGcccAgTGCCCTCGTGATGTCAAGTTCATCAACGGAGTT
Y G T G Y C D A Q C P R D V K F I N G V
GCCAACTCTGAGGGCTGGAAGCCCTCTGACAGTGATGTCAACGCtggtgttggtaatctg
A N S E G W K P S D S D V N A G V G N L
ggcacctgctgccccgagatggatatctgggaggccaactccatctccaccgccttcact
G T C C P E M D I W E A N S I S T A F T
cctcatccttgcaccaagctcacacagcactcttgcactggcgactcttgtggtggaacc
P H P C T K L T Q H S C T G D S C G G T
tactctagtgaccgatatggcggtacttgcgatgccgacggttgtgatttcaatgcctac
Y S S D R Y G G T C D A D G C D F N A Y
cgtcagggcaacaagaccttctacggtcctggatccaacttcaacatcgacaccaccaag
R Q G N K T F Y G P G S N F N I D T T K
aagatgactgttgtcactcagttccacaagggcAGCAAcGGACGTCTTTCTGAGATCACC
K M T V V T Q F H K G S N G R L S E I T
CGTCTGTACGTCCAGAACGGCAAGGTCATTGCCAACTCAGAGTCCAAGATTGCAGGCAAC
R L Y V Q N G K V I A N S E S K I A G N
CCCGGTAGCTCTCTCACCTCTGACTTCTGCTCCAAGCAGAAGAGCGTCTTTGGCGATATC
P G S S L T S D F C S K Q K S V F G D I
GATGACTTCTCTAAGAAGGGTGGCTGGAACGgCATGAGCGATGCTCTCTCTGCCCCTATG
D D F S K K G G W N G M S D A L S A P M
GTTCTTGTTATGTCTCTCTGGCACGACCACCACTCCAACATGCTCTGGCTGgACtctacc
V L V M S L W H D H H S N M L W L D S T
tacccaaccgactctaccaaggttggatctcaacgaggttcttgcgctaccacctctggc
Y P T D S T K V G S Q R G S C A T T S G
aagcccctccgaccttgagcgagatgttcccaactccaaggtttccttctccaacatcaAG
K P S D L E R D V P N S K V S F S N I K
TTCGGTCCCATCGGAAGCACCTACAAGAGCGACGGCACCACCCCCAACCCCCCTgCCAGC
F G P I G S T Y K S D G T T P N P P A S
AGCAGCACCACTGGTTCTTCCACTCCCACCAACCCCCCTGCCGGTAGCGTCGACCAATGG
S S T T G S S T P T N P P A G S V D Q W
GGACAgTGcGGTGGCCAgaactacagcggccccacgacctgcaagtctcctttcacctgc
G Q C G G Q N Y S G P T T C K S P F T C
aagaagatcaacgacttctactcccagtgtcagtaaaggggctgccgagctatctagcat
K K I N D F Y S Q C Q .
gagattgagaaacgatgtgatgagtggacgatcaaggagaagtgtgtggatgatatgaac
ttgatgtgggaggac
```

FIG. 12

```
gaattcgcggccgcctgcttcgaagcatcagctcattgagatcagtcaaaatgcatacc
                                                         M  H  T
ctttcggttctcctcgctctcgctcccgtgtccgcccttgctcaggctcccatctgggga
 L  S  V  L  L  A  L  A  P  V  S  A  L  A  Q  A  P  I  W  G
cagtgcggtggcaatggttggaccggtgctacaacctgcgctagtggtctgaagtgtgag
 Q  C  G  G  N  G  W  T  G  A  T  T  C  A  S  G  L  K  C  E
aagatcaacgactggtactatcagtgtgttcctggatctggaggatctgaacccagcct
 K  I  N  D  W  Y  Y  Q  C  V  P  G  S  G  G  S  E  P  Q  P
tcgtcaactcaggtggtggcactcctcagcctactggcggtaacagcggcggcactggt
 S  S  T  Q  G  G  G  T  P  Q  P  T  G  G  N  S  G  G  T  G
ctcgacgccaaattcaaggccaagggcaagcagtactttggtaccgagattgaccactac
 L  D  A  K  F  K  A  K  G  K  Q  Y  F  G  T  E  I  D  H  Y
caccttaacaacaatcctctgatcaacattgtcaaggcccagtttggccaagtgacatgc
 H  L  N  N  N  P  L  I  N  I  V  K  A  Q  F  G  Q  V  T  C
gagaacagcatgaagtgggatgccattgagcttcacgcaactccttcaccttcagtaac
 E  N  S  M  K  W  D  A  I  E  P  S  R  N  S  F  T  F  S  N
gctgacaaggtcgtcgacttcgccactcagaacggcaagctcatccgtgGCCACACTCTT
 A  D  K  V  V  D  F  A  T  Q  N  G  K  L  I  R  G  H  T  L
CTCTGGCACTCTCAGCTGCCTCAGTGGGTTCAGAACATCAACGATCGCTCTACCCTCACC
 L  W  H  S  Q  L  P  Q  W  V  Q  N  I  N  D  R  S  T  L  T
GCGGTCATCGAGAACCACGTCAAGACCATGGTCACCCGCTACAAGGGCAAGATCCTCCAG
 A  V  I  E  N  H  V  K  T  M  V  T  R  Y  K  G  K  I  L  Q
TGGGACGTTGTCAACAACGAGATCTTCGCTGAGGACGGTAACCTCCGCGACAGTGTCTTC
 W  D  V  V  N  N  E  I  F  A  E  D  G  N  L  R  D  S  V  F
AGCCGAGTTCTCGGTGAGGACTTTGTCGGTATTGCTTTCCGCGCTGCCCGCGCCGCTGAT
 S  R  V  L  G  E  D  F  V  G  I  A  F  R  A  A  R  A  A  D
CCCGCTGCCAAGCTCTACATCAACGATTATAACCTCGACAAGTCCGACTATGCTAAGGTC
 P  A  A  K  L  Y  I  N  D  Y  N  L  D  K  S  D  Y  A  K  V
ACCCGCGGAATGGTCGCTCACGTTAATAAGTGGATTGCTGCTGGTATTCCCATCGACGGT
 T  R  G  M  V  A  H  V  N  K  W  I  A  A  G  I  P  I  D  G
ATTGGATCTCAGGGCCATCTTGCTGCTCCTAGTGGCTGGAACCCTGCCTCTGGTGTTCCT
 I  G  S  Q  G  H  L  A  A  P  S  G  W  N  P  A  S  G  V  P
GCTGCTCTCCGAGCTCTTGCCGCCTCGGACGCCAAGGAGATTGCTATcactgagcttgat
 A  A  L  R  A  L  A  A  S  D  A  K  E  I  A  I  T  E  L  D
attgccggtgccagtgctaacgattaccttactgtcatgaacgcttgccttgccgttccc
 I  A  G  A  S  N  D  Y  L  T  V  M  N  A  C  L  A  V  P
aagtgtgtcggcatcactgtctggggtgtctctgacaaggactcgtggcgacctggtgac
 K  C  V  G  I  T  V  W  G  V  S  D  K  D  S  W  R  P  G  D
aaccccctcctctacgacagcaactaccagcccaaggctgctttcaatgccttggctaac
 N  P  L  L  Y  D  S  N  Y  Q  P  K  A  A  F  N  A  L  A  N
gctctgtgagctgttgttgatgtatgtcgctggatcatacaacgaaacgtcctagttgga
 A  L
taaagcgttgatggtagaatgat
```

FIG. 13

```
gaattcgcggccgcctagataagtcactacctgatctctgaataatctttcatcatgaag
                                                           M  K
tctctctcactcatcctctcagccctggctgtccaggtcgctgttgctcaaaccccgac
 S  L  S  L  I  L  S  A  L  A  V  Q  V  A  V  A  Q  T  P  D
aaggccaaggagcagcaccccaagctcgagacctaccgctgcaccaaggcctctggctgc
 K  A  K  E  Q  H  P  K  L  E  T  Y  R  C  T  K  A  S  G  C
aagaagcaaaccaactacatcgtcgccgaCgcaggtattcacggcattCgcagaagcgCC
 K  K  Q  T  N  Y  I  V  A  D  A  G  I  H  G  I  R  R  S  A
GGCTGCGGTGACTGGGGTCAAAAGCCCAACGCCACAGCCTGCCCCGATGAGGCATCCTGC
 G  C  G  D  W  G  Q  K  P  N  A  T  A  C  P  D  E  A  S  C
GCTAAGAACTGTATCCTCAGTGGTATGGACTCAAACGCTTACAAGAACGCTGGTATCACT
 A  K  N  C  I  L  S  G  M  D  S  N  A  Y  K  N  A  G  I  T
ACTTCTGGCAACAAGCTTCGTCTTCAGCAGCTTATCAACAACCAGCTTGTTTCTCCTCGG
 T  S  G  N  K  L  R  L  Q  Q  L  I  N  N  Q  L  V  S  P  R
GTTTATCTGCTTGAGGAGAACAAGAAGAAGTATGAGATGCTTCAGCTCACTGGTACTGAA
 V  Y  L  L  E  E  N  K  K  K  Y  E  M  L  H  L  T  G  T  E
TTCTCTTTCGACGTTGAGATGGAGAAGCTTCCTTGTGGTATGAATGGTGCTTTGTACCTT
 F  S  F  D  V  E  M  E  K  L  P  C  G  M  N  G  A  L  Y  L
TCCGAGATGCCACAGGATGGTGGTAAGAGCACGAGCCGAAACAGCAAGGCTGGTGCCTAC
 S  E  M  P  Q  D  G  G  K  S  T  S  R  N  S  K  A  G  A  Y
TATGGTGCTGGATACTGTGATGCTCAGTGCTACGTCactccttTcATCAACGGAGTTGGC
 Y  G  A  G  Y  C  D  A  Q  C  Y  V  T  P  F  I  N  G  V  G
AACATCAAGGGACAGGGTGTCTGCTGTAACGAGCTCGACATCTGGGAGGCCAACTCCCGC
 N  I  K  G  Q  G  V  C  C  N  E  L  D  I  W  E  A  N  S  R
GCAACTCACATTGCTCCTCACCCTTGCAGCAAGCCCGGCCTCTACGGCTGCACAGGCGAT
 A  T  H  I  A  P  H  P  C  S  K  P  G  L  Y  G  C  T  G  D
GAGTGCGGCAGCTCCGGTTTCTGCGACAAGGCCGGCTGCGGCTGGAACCACAACCGCATC
 E  C  G  S  S  G  I  C  D  K  A  G  C  G  W  N  H  N  R  I
AACGTGACCGACTTCTACGGccgcggCAAGCAGTACAAGGTCGACAGCACCCGCAAGTTC
 N  V  T  D  F  Y  G  R  G  K  Q  Y  K  V  D  S  T  R  K  F
ACCGTGACATCTCAGTTCGTCGCCAACAAGCAGGGTGATCTCATCGAGCTGCACCGCCAC
 T  V  T  S  Q  F  V  A  N  K  Q  G  D  L  I  E  L  H  R  H
TACATCCAGGACAACAAGGTCAtcgagtctgctgtcgtcaacatctccggccctcccaag
 Y  I  Q  D  N  K  V  I  E  S  A  V  V  N  I  S  G  P  P  K
atcaacttcatcaatgacaagtactgcgctgccaccggcgccaacgagtacatgcgcctc
 I  N  F  I  N  D  K  Y  C  A  A  T  G  A  N  E  Y  M  R  L
ggcggtactaagcaaatgggcgatgccatgtcccgcggaatggttctcgccatgagcgtc
 G  G  T  K  Q  M  G  D  A  M  S  R  G  M  V  L  A  M  S  V
tggtggagcgagggtgatttcatggcctggttggatcagggtgttgctggaccctgtgac
 W  W  S  E  G  D  F  M  A  W  L  D  Q  G  V  A  G  P  C  D
gccaccgagggcgatcccaagaacatcgtcaaggtgcagcccaaccctgaagtgacattt
 A  T  E  G  D  P  K  N  I  V  K  V  Q  P  N  P  E  V  T  F
agcaacatcagaattggagagattggatctacttcatcggtcaaggctcctgcgtatcct
 S  N  I  R  I  G  E  I  G  S  T  S  S  V  K  A  P  A  Y  P
ggtcctcaccgcttgtaaaaacatcaaacaacaccgtgtccaatatggATCTTAGTGTCC
 G  P  H  R  L  .
ACTTGCTGGGAAGCTATTGGAGCACATATGCAAAACAGATGTCCACTAGCTTGACACGTA

TGTCGGGGCAAAAAAATCTCTTTCTAGGATAGGAGAACATATTGGGTGTTTGGACTTGTA

TATAAATGATACATTTTTCATATTATATTATTTTCAACATATTTTATTTCACGAAAAAAA

AAAAAAAAAAAAAAAAAAAAAAA
```

FIG. 14A

```
           10         20        30        40        50        60
            |          |         |         |         |         |
TTTCTTCGTCGAGCTCGAGTCGTCCGCCGTCTCCTCCTCCTCCTCCTTCCAGTCTTTGAG 70        80        90       100       110       120
            |         |         |         |         |         |
TTCCTTCGACCTGCAGCGTCCTGAACAACTCGCTCTAGCTCAACAACCATGGCTCGCGGT
                                                  MetAlaArgGly 130       140       150       160       170       180
            |         |         |         |         |         |
ACCGCTCTCCTCGGCCTGACCGCGCTCCTCCTGGGGCTGGTCAACGGCCAGAAGCCTGGT
ThrAlaLeuLeuGlyLeuThrAlaLeuLeuLeuGlyLeuValAsnGlyGlnLysProGly 190       200       210       220       230       240
            |         |         |         |         |         |
GAGACCAAGGAGGTTCACCCCCAGCTCACGACCTTCCGCTGCACGAAGAGGGGTGGTTGC
GluThrLysGluValHisProGlnLeuThrThrPheArgCysThrLysArgGlyGlyCys 250       260       270       280       290       300
            |         |         |         |         |         |
AAGCCGGCGACCAACTTCATCGTGCTTGACTCGCTGTCGCACCCCATCCACCGCGCTGAG
LysProAlaThrAsnPheIleValLeuAspSerLeuSerHisProIleHisArgAlaGlu
```

FIG. 14B

```
         310       320       330       340       350       360
          |         |         |         |         |         |
GGCCTGGGCCCTGGCGGCTGCGGCGACTGGGGCAACCCGCCGCCCAAGGACGTCTGCCCG
GlyLeuGlyProGlyGlyCysGlyAspTrpGlyAsnProProProLysAspValCysPro 370       380       390       400       410       420
          |         |         |         |         |         |
GACGTCGAGTCGTGCGCCAAGAACTGCATCATGGAGGGCATCCCCGACTACAGCCAGTAC
AspValGluSerCysAlaLysAsnCysIleMetGluGlyIleProAspTyrSerGlnTyr 430       440       450       460       470       480
          |         |         |         |         |         |
GGCGTCACCACCAACGGCACCAGCCTCCGCCTGCAGCACATCCTCCCCGACGGCCGCGTC
GlyValThrThrAsnGlyThrSerLeuArgLeuGlnHisIleLeuProAspGlyArgVal 490       500       510       520       530       540
          |         |         |         |         |         |
CCGTCGCCGCGTGTCTACCTGCTCGACAAGACGAAGCGCCGCTATGAGATGCTCCACCTG
ProSerProArgValTyrLeuLeuAspLysThrLysArgArgTyrGluMetLeuHisLeu 550       560       570       580       590       600
          |         |         |         |         |         |
ACCGGCTTCGAGTTCACCTTCGACGTCGACGCCACCAAGCTGCCCTGCGGCATGAACAGC
ThrGlyPheGluPheThrPheAspValAspAlaThrLysLeuProCysGlyMetAsnSer 610       620       630       640       650       660
          |         |         |         |         |         |
GCTCTGTACCTGTCCGAGATGCACCCGACCGGTGCCAAGAGCAAGTACAACTCCGGCGGT
AlaLeuTyrLeuSerGluMetHisProThrGlyAlaLysSerLysTyrAsnSerGlyGly
```

FIG. 14C

```
       670        680        690        700        710        720
        |          |          |          |          |          |
GCCTACTACGGTACTGGCTACTGCGATGCTCAGTGCTTCGTGACGCCCTTCATCAACGGC
AlaTyrTyrGlyThrGlyTyrCysAspAlaGlnCysPheValThrProPheIleAsnGly 730        740        750        760        770        780
        |          |          |          |          |          |
TTGGGCAACATCGAGGGCAAGGGCTCGTGCTGCAACGAGATGGATATCTGGGAGGTCAAC
LeuGlyAsnIleGluGlyLysGlySerCysCysAsnGluMetAspIleTrpGluValAsn 790        800        810        820        830        840
        |          |          |          |          |          |
TCGCGCGCCTCGCACGTGGTTCCCCACACCTGCAACAAGAAGGGCCTGTACCTTTGCGAG
SerArgAlaSerHisValValProHisThrCysAsnLysLysGlyLeuTyrLeuCysGlu 850        860        870        880        890        900
        |          |          |          |          |          |
GGTGAGGAGTGCGCCTTCGAGGGTGTTTGCGACAAGAACGGCTGCGGCTGGAACAACTAC
GlyGluGluCysAlaPheGluGlyValCysAspLysAsnGlyCysGlyTrpAsnAsnTyr 910        920        930        940        950        960
        |          |          |          |          |          |
CGCGTCAACGTGACTGACTACTACGGCCGGGGCGAGGAGTTCAAGGTCAACACCCTCAAG
ArgValAsnValThrAspTyrTyrGlyArgGlyGluGluPheLysValAsnThrLeuLys 970        980        990       1000       1010       1020
        |          |          |          |          |          |
CCCTTCACCGTCGTCACTCAGTTCTTGGCCAACCGCAGGGGCAAGCTCGAGAAGATCCAC
ProPheThrValValThrGlnPheLeuAlaAsnArgArgGlyLysLeuGluLysIleHis
```

FIG. 14D

```
           1030       1040       1050       1060       1070        080
            |          |          |          |          |          |
      CGCTTCTACGTGCAGGACGGCAAGGTCATCGAGTCCTTCTACACCAACAAGGAGGGAGTC
      ArgPheTyrValGlnAspGlyLysValIleGluSerPheTyrThrAsnLysGluGlyVal 1090       1100       1110       1120       1130       1140
            |          |          |          |          |          |
      CCTTACACCAACATGATCGATGACGAGTTCTGCGAGGCCACCGGCTCCCGCAAGTACATG
      ProTyrThrAsnMetIleAspAspGluPheCysGluAlaThrGlySerArgLysTyrMet 1150       1160       1170       1180       1190       1200
            |          |          |          |          |          |
      GAGCTCGGCGCCACCCAGGGCATGGGCGAGGCCCTCACCCGCGGCATGGTCCTGGCCATG
      GluLeuGlyAlaThrGlnGlyMetGlyGluAlaLeuThrArgGlyMetValLeuAlaMet 1210       1220       1230       1240       1250       1260
            |          |          |          |          |          |
      AGCATCTGGTGGGACCAGGGCGGCAACATGGAGTGGCTCGACCACGGCGAGGCCGGCCCC
      SerIleTrpTrpAspGlnGlyGlyAsnMetGluTrpLeuAspHisGlyGluAlaGlyPro 1270       1280       1290       1300       1310       1320
            |          |          |          |          |          |
      TGCGCCAAGGGCGAGGGCGCCCCGTCCAACATTGTCCAGGTTGAGCCCTTCCCCGAGGTC
      CysAlaLysGlyGluGlyAlaProSerAsnIleValGlnValGluProPheProGluVal 1330       1340       1350       1360       1370       1380
            |          |          |          |          |          |
      ACCTACACCAACCTCCGCTGGGGCGAGATCGGCTCGACCTACCAGGAGGTTCAGAAGCCT
      ThrTyrThrAsnLeuArgTrpGlyGluIleGlySerThrTyrGlnGluValGlnLysPro
```

FIG. 14E

```
         1390        1400        1410        1420        1430        1440
          |           |           |           |           |           |
AAGCCCAAGCCCGGCCACGGCCCCCGGAGCGACTAAGTGGTGATGGGATAGAGGGATAGA
LysProLysProGlyHisGlyProArgSerAspEND 1450        1460        1470        1480        1490        1500
          |           |           |           |           |           |
ATAGTGGATAGCACATAGATCGGCGGTTTTGGATAGTTTAATACATTCCGTTGCCGTTGT

1510
          |
GAAAAAAAAA - poly-A
```

FIG. 15A

```
         10        20        30        40        50        60
          |         |         |         |         |         |
ATGCGTTCCTCCCCCCTCCTCCCGTCCGCCGTTGTGGCCGCCCTGCCGGTGTTGGCCCTT

METArgSerSerProLeuLeuProSerAlaValValAlaAlaLeuProValLeuAlaLeu
    43 kdal signalpeptide and N terminal 70        80        90       100       110       120
          |         |         |         |         |         |
GCCGCTGATGGCAGGAGTGATGTCACTTTCACGATTAATACGCAGTCGGAACGTGCAGCG AlaAlaAspGlyArgSerAspValThrPheThrIleAsnThrGlnSerGluArgAlaAla
N terminal 130       140       150       160       170       180
          |         |         |         |         |         |
ATCAGCCCCAATATTTACGGAACCAATCAGGATCTGAGCGGGACGGAGAACTGGTCATCC IleSerProAsnIleTyrGlyThrAsnGlnAspLeuSerGlyThrGluAsnTrpSerSer 190       200       210       220       230       240
          |         |         |         |         |         |
CGCAGGCTCGGAGGCAACCGGCTGACGGGTTACAACTGGGAGAACAACGCATCCAGCGCC ArgArgLeuGlyGlyAsnArgLeuThrGlyTyrAsnTrpGluAsnAsnAlaSerSerAla 250       260       270       280       290       300
          |         |         |         |         |         |
GGAAGGGACTGGCTTCATTACAGCGATGATTTTCTCTGCGGCAACGGTGGTGTTCCAGAC GlyArgAspTrpLeuHisTyrSerAspAspPheLeuCysGlyAsnGlyGlyValProAsp
Endo 1 core 310       320       330       340       350       360
          |         |         |         |         |         |
ACCGACTGCGACAAGCCGGGGCGGTTGTTACCGCTTTTCACGATAAATCTTTGGAGAAT ThrAspCysAspLysProGlyAlaValThrAlaPheHisAspLysSerLeuGluAsn 370       380       390       400       410       420
          |         |         |         |         |         |
GGAGCTTACTCCATTGTAACGCTGCAAATGGCGGGTTATGTGTCCCGGGATAAGAACGGT GlyAlaTyrSerIleValThrLeuGlnMETAlaGlyTyrValSerArgAspLysAsnGly 430       440       450       460       470       480
          |         |         |         |         |         |
CCAGTTGACGAGAGTGAGACGGCTCCGTCACCGCGTTGGGATAAGGTCGAGTTTGCCAAA ProValAspGluSerGluThrAlaProSerProArgTrpAspLysValGluPheAlaLys
```

FIG. 15B

```
              490       500       510       520       530       540
               |         |         |         |         |         |
          AATGCGCCGTTCTCCCTTCAGCCTGATCTGAACGACGGACAAGTGTATATGGATGAAGAA
          AsnAlaProPheSerLeuGlnProAspLeuAsnAspGlyGlnValTyrMETAspGluGlu 550       560       570       580       590       600
               |         |         |         |         |         |
          GTTAACTTCCTGGTCAACCGGTATGGAAACGCTTCAACGTCAACGGGCATCAAAGCGTAT
          ValAsnPheLeuValAsnArgTyrGlyAsnAlaSerThrSerThrGlyIleLysAlaTyr 610       620       630       640       650       660
               |         |         |         |         |         |
          TCGCTGGATAACGAGCCGGCGCTGTGGTCTGAGACGCATCCAAGGATTCATCCGGAGCAG
          SerLeuAspAsnGluProAlaLeuTrpSerGluThrHisProArgIleHisProGluGln 670       680       690       700       710       720
               |         |         |         |         |         |
          TTACAAGCGGCAGAACTCGTCGCTAAGAGCATCGACTTGTCAAAGGCGGTGAAGAACGTC
          LeuGlnAlaAlaGluLeuValAlaLysSerIleAspLeuSerLysAlaValLysAsnVal 730       740       750       760       770       780
               |         |         |         |         |         |
          GATCCGCATGCCGAAATATTCGGTCCTGCCCTTTACGGTTTCGGCGCATATTTGTCTCTG
          AspProHisAlaGluIlePheGlyProAlaLeuTyrGlyPheGlyAlaTyrLeuSerLeu 790       800       810       820       830       840
               |         |         |         |         |         |
          CAGGACGCACCGGATTGGCCGAGTTTGCAAGGCAACTACAGCTGGTTTATCGATTACTAT
          GlnAspAlaProAspTrpProSerLeuGlnGlyAsnTyrSerTrpPheIleAspTyrTyr 850       860       870       880       890       900
               |         |         |         |         |         |
          CTGGATCAGATGAAGAATGCTCATACGCAGAACGGCAAAAGATTGCTCGATGTGCTGGAC
          LeuAspGlnMETLysAsnAlaHisThrGlnAsnGlyLysArgLeuLeuAspValLeuAsp 910       920       930       940       950       960
               |         |         |         |         |         |
          GTCCACTGGTATCCGGAAGCACAGGGCGGAGGCCAGCGAATCGTCTTTGGCGGGGCGGGC
          ValHisTrpTyrProGluAlaGlnGlyGlyGlnArgIleValPheGlyGlyAlaGly
```

FIG. 15C

```
            970       980       990      1000      1010      1020
             |         |         |         |         |         |
        AATATCGATACGCAGAAGGCTCGCGTACAAGCGCCAAGATCGCTATGGGATCCGGCTTAC
        AsnIleAspThrGlnLysAlaArgValGlnAlaProArgSerLeuTrpAspProAlaTyr 1030      1040      1050      1060      1070      1080
             |         |         |         |         |         |
        CAGGAAGACAGCTGGATCGGCACATGGTTTTCAAGCTACTTGCCCTTAATTCCGAAGCTG
        GlnGluAspSerTrpIleGlyThrTrpPheSerSerTyrLeuProLeuIleProLysLeu 1090      1100      1110      1120      1130      1140
             |         |         |         |         |         |
        CAATCTTCGATTCAGACGTATTATCCGGGTACGAAGCTGGCGATCACAGAGTTCAGCTAC
        GlnSerSerIleGlnThrTyrTyrProGlyThrLysLeuAlaIleThrGluPheSerTyr 1150      1160      1170      1180      1190      1200
             |         |         |         |         |         |
        GGCGGAGACAATCACATTTCGGGAGGCATAGCTACCGCGGACGCGCTCGGCATTTTTGGA
        GlyGlyAspAsnHisIleSerGlyGlyIleAlaThrAlaAspAlaLeuGlyIlePheGly 1210      1220      1230      1240      1250      1260
             |         |         |         |         |         |
        AAATATGGCGTTTATGCCGCGAATTACTGGCAGACGGAGGACAATACCGATTATACCAGC
        LysTyrGlyValTyrAlaAlaAsnTyrTrpGlnThrGluAspAsnThrAspTyrThrSer 1270      1280      1290      1300      1310      1320
             |         |         |         |         |         |
        GCTGCTTACAAGCTGTATCGCAACTACGACGGCAATAAATCGGGGTTCGGCTCGATCAAA
        AlaAlaTyrLysLeuTyrArgAsnTyrAspGlyAsnLysSerGlyPheGlySerIleLys 1330      1340      1350      1360      1370      1380
             |         |         |         |         |         |
        GTGGACGCCGCTACGTCCGATACGGAGAACAGCTCGGTATACGCTTCGGTAACTGACGAG
        ValAspAlaAlaThrSerAspThrGluAsnSerSerValTyrAlaSerValThrAspGlu 1390      1400      1410      1420      1430      1440
             |         |         |         |         |         |
        GAGAATTCCGAACTCCACCTGATCGTGCTGAATAAAAATTTCGACGATCCGATCAACGCT
        GluAsnSerGluLeuHisLeuIleValLeuAsnLysAsnPheAspAspProIleAsnAla
```

FIG. 15D

```
       1450      1460      1470      1480      1490      1500
         |         |         |         |         |         |
ACTTTCCAGCTGTCTGGTGATAAAACCTACACATCCGGGAGAGTATGGGGCTTCGACCAA

ThrPheGlnLeuSerGlyAspLysThrTyrThrSerGlyArgValTrpGlyPheAspGln 1510      1520      1530      1540      1550      1560
         |         |         |         |         |         |
ACCGGATCCGACATTACGGAACAAGCAGCTATAACGAATATTAACAACAATCAATTCACG

ThrGlySerAspIleThrGluGlnAlaAlaIleThrAsnIleAsnAsnAsnGlnPheThr 1570      1580      1590      1600      1610      1620
         |         |         |         |         |         |
TATACGCTTCCTCCATTGTCGGCTTACCACATTGTTCTGAAAGCGGATAGCACCGAACCG

TyrThrLeuProProLeuSerAlaTyrHisIleValLeuLysAlaAspSerThrGluPro 1630      1640      1650      1660      1670      1680
         |         |         |         |         |         |
GTCATCTCCGAGATCCCCTCCAGCAGCACCAGCTCTCCGGTCAACCAGCCTACCAGCACC

ValIleSerGluIleProSerSerSerThrSerSerProValAsnGlnProThrSerThr
     Linker                         43 kdal B region 1690      1700      1710      1720      1730      1740
         |         |         |         |         |         |
AGCACCACGTCCACCTCCACCACCTCGAGCCCGCCAGTCCAGCCTACGACTCCCAGCGGC SerThrThrSerThrSerThrThrSerSerProProValGlnProThrThrProSerGly 1750      1760      1770      1780      1790      1800
         |         |         |         |         |         |
TGCACTGCTGAGAGGTGGGCTCAGTGCGGCGGCAATGGCTGGAGCGGCTGCACCACCTGC CysThrAlaGluArgTrpAlaGlnCysGlyGlyAsnGlyTrpSerGlyCysThrThrCys
                           43 kdal A region 1810      1820      1830      1840      1850
         |         |         |         |         |
GTCGCTGGCAGCACTTGCACGAAGATTAATGACTGGTACCATCAGTGCCTGTAG ValAlaGlySerThrCysThrLysIleAsnAspTrpTyrHisGlnCysLeu---
```

ENZYME CAPABLE OF DEGRADING CELLULOSE OR HEMICELLULOSE

CROSS-REFERENCE TO RELATED APPLICATIONS

This application is a continuation of application Ser. No. 08/361,920 filed Dec. 22, 1994 now U.S. Pat. No. 5,457,046, which is a continuation of Ser. No. 07/940,860 filed Oct. 28, 1992, now abandoned which is a national application of PCT/DK91/00124 filed May 8, 1991, the contents of which are fully incorporated herein by reference.

FIELD OF INVENTION

The present invention relates to a cellulose- or hemicellulose-degrading enzyme, a DNA construct coding for the enzyme, a method of producing the enzyme, and an agent for degrading cellulose or hemicellulose comprising the enzyme.

BACKGROUND OF THE INVENTION

Enzymes which are able to degrade cellulose have previously been suggested for the conversion of biomass into liquid fuel, gas and feed protein. However, the production of fermentable sugars from biomass by means of cellulolytic enzymes is not yet able to compete economically with, for instance, the production of glucose from starch by means of α-amylase due to the inefficiency of the currently used cellulolytic enzymes. Cellulolytic enzymes may furthermore be used in the brewing industry for the degradation of β-glucans, in the baking industry for improving the properties of flour, in paper pulp processing for removing the noncrystalline parts of cellulose, thus increasing the proportion of crystalline cellulose in the pulp, and in animal feed for improving the digestibility of glucans. A further important use of cellulolytic enzymes is for textile treatment, e.g. for reducing the harshness of cottoncontaining fabrics (cf., for instance, GB 1 368 599 or U.S. Pat. No. 4,435,307), for soil removal and colour clarification of fabrics (cf., for instance, EP 220 016) or for providing a localized variation in colour to give the fabrics a "stone-washed" appearance (cf., for instance, EP 307 564).

The practical exploitation of cellulolytic enzymes has, to some extent, been set back by the nature of the known cellulase preparations which are often complex mixtures of a variety of single cellulase components, and which may have a rather low specific activity. It is difficult to optimise the production of single components in multiple enzyme systems and thus to implement industrial cost-effective production of cellulolytic enzymes, and their actual use has been hampered by difficulties arising from the need to employ rather large quantities of the enzymes to achieve the desired effect.

The drawbacks of previously suggested cellulolytic enzymes may be remedied by using single-component enzymes selected for a high specific activity.

Single-component cellulolytic enzymes have been isolated from, e.g. *Trichoderma reesei* (cf. Teeri et al., *Gene* 51, 1987, pp. 43–52; P. M. Abuja, *Biochem. Biophys. Res. Comm.* 156, 1988, pp. 180–185; and P. J. Kraulis, *Biochemistry* 28, 1989, pp. 7241–7257). The *T. reesei* cellulases have been found to be composed of a terminal A region responsible for binding to cellulose, a B region linking the A region to the core of the enzyme, and a core containing the catalytically active domain. The A region of different *T. reesei* cellulases has been found to be highly conserved, and a strong homology has also been observed with a cellulase produced by *Phanerochaete chrysosporium* (Sims et al., *Gene* 74, 1988, pp. 411–422).

SUMMARY OF THE INVENTION

It has surprisingly been found that other fungi, which are not closely related to either *Trichoderma reesei* or *Phanerochaete chrysosporium*, are capable of producing enzymes which contain a region which is homologous to the A region of *T. reesei* cellulases.

Accordingly, the present invention relates to a cellulose- or hemicellulose-degrading enzyme which is derivable from a fungus other than Trichoderma or Phanerochaete, and which comprises a carbohydrate binding domain homologous to a terminal A region of *Trichoderma reesei* cellulases, which carbohydrate binding domain comprises the following amino acid sequence

```
1                                           10
Xaa Xaa Gln Cys Gly Gly Xaa Xaa Xaa Xaa Gly Xaa Xaa Xaa Cys Xaa
         20                                  30
Xaa Xaa Xaa Xaa Cys Xaa Xaa Xaa Asn Xaa Xaa Tyr Xaa Gln Cys Xaa
Xaa  (SEQ ID NO: 1)
``` or a subsequence thereof capable of effecting binding of the enzyme to an insoluble cellulosic or hemicellulosic substrate.

"Xaa" is intended to indicate variations in the amino acid sequence of the carbohydrate binding domain of different enzymes. A hyphen is intended to indicate a "gap" in the amino acid sequence (compared to other, similar enzymes).

In the present context, the term "cellulose" is intended to include soluble and insoluble, amorphous and crystalline forms of cellulose. The term "hemicellulose" is intended to include glucans (apart from starch), mannans, xylans, arabinans or polyglucuronic or polygalacturonic acid. The term "carbohydrate binding domain" ("CBD") is intended to indicate an amino acid sequence capable of effecting binding of the enzyme to a carbohydrate substrate, in particular cellulose or hemicellulose as defined above. The term "homologous" is intended to indicate a high degree of identity in the sequence of amino acids constituting the carbohydrate binding domain of the present enzyme and the amino acids constituting the A region found in *T. reesei* cellulases ("A region" is the term used to denote the cellulose (i.e. carbohydrate) binding domain of *T. reesei* cellulases).

It is currently believed that cellulose- or hemicellulose-degrading enzymes which contain a sequence of amino acids which is identifiable as a carbohydrate binding domain (or "A region" based on its homology to the A region of *T. reesei* cellulases possess certain desirable characteristics as a result of the function of the carbohydrate binding domain in the enzyme molecule which is to mediate binding to solid substrates (including cellulose) and consequently to enhance the activity of such enzymes towards such substrates. The identification and preparation of carbohydrate binding domain-containing enzymes from a variety of microorganisms is therefore of considerable interest.

Cellulose- or hemicellulose-degrading enzymes of the invention may conveniently be identified by screening genomic or cDNA libraries of different fungi with a probe comprising at least part of the DNA encoding the A region of *T. reesei* cellulases. Due to the intraspecies (i.e. different *T. reesei* cellulases) and interspecies homology observed for the carbohydrate binding domains of different cellulose- or hemicellulose-degrading enzymes, there is reason to believe that this screening method constitutes a convenient way of isolating enzymes of current interest.

acid is preferentially Gly or Pro. In position 19, the amino acid (if present) is preferentially Ser, Thr, Phe, Leu or Ala. In position 20, the amino acid is preferentially Thr or Lys. In position 24, the amino acid is preferentially Gln or Ile. In position 26, the amino acid is preferentially Gln, Asp or Ala. In position 27, the amino acid is preferentially Trp, Phe or Tyr. In position 29, the amino acid is preferentially Ser, His or Tyr. In position 32, the amino acid is preferentially Leu, Ile, Gln, Val or Thr.

Examples of specific CBD-containing enzymes of the invention are those which comprise one of the following amino acid sequences

```
Trp Gly Gln Cys Gly Gly Gln Gly Trp Asn Gly Pro Thr Cys Cys Glu Ala Gly Thr Thr Cys
Arg Gln Gln Asn Gln Trp Tyr Ser Gln Cys Leu     (SEQ ID NO:2);

Trp Gly Gln Cys Gly Gly Ile Gly Trp Asn Gly Pro Thr Thr Cys Val Ser Gly Ala Thr Cys
Thr Lys Ile Asn Asp Trp Tyr His Gln Cys Leu     (SEQ ID NO:3);

Trp Gly Gln Cys Gly Gly Ile Gly Phe Asn Gly Pro Thr Cys Cys Gln Ser Gly Ser Thr Cys
Val Lys Gln Asn Asp Trp Tyr Ser Gln Cys Leu     (SEQ ID NO:4);

Trp Gly Gln Cys Gly Gly Asn Gly Tyr Ser Gly Pro Thr Thr Cys Ala Glu Gly  –  Thr Cys
Lys Lys Gln Asn Asp Trp Tyr Ser Gln Cys Thr Pro (SEQ ID NO:5);

Trp Gln Gln Cys Gly Gly Gln Gly Trp Gln Gly Pro Thr Cys Cys Ser Gln Gly  –  Thr Cys
Arg Ala Gln Asn Gln Trp Tyr Ser Gln Cys Leu Asn (SEQ ID NO:6);

Trp Gly Gln Cys Gly Gly Gln Gly Tyr Ser Gly Cys Thr Asn Cys Glu Ala Gly Ser Thr Cys
Arg Gln Gln Asn Ala Tyr Tyr Ser Gln Cys Ile     (SEQ ID NO:7);

Trp Gly Gln Cys Gly Gly Gln Gly Tyr Ser Gly Cys Arg Asn Cys Glu Ser Gly Ser Thr Cys
Arg Ala Gln Asn Asp Trp Tyr Ser Gln Cys Leu     (SEQ ID NO:8);

Trp Ala Gln Cys Gly Gly Asn Gly Trp Ser Gly Cys Thr Thr Cys Val Ala Gly Ser Thr Cys
Thr Lys Ile Asn Asp Trp Tyr His Gln Cys Leu     (SEQ ID NO:9);

Trp Gly Gln Cys Gly Gly Gln Asn Tyr Ser Gly Pro Thr Thr Cys Lys Ser Pro Phe Thr Cys
Lys Lys Ile Asn Asp Phe Tyr Ser Gln Cys Gln     (SEQ ID NO:10); or

Trp Gly Gln Cys Gly Gly Asn Gly Trp Thr Gly Ala Thr Thr Cys Ala Ser Gly Leu Lys Cys
Glu Lys Ile Asn Asp Trp Tyr Tyr Gln Cys Val     (SEQ ID NO:11).
```

DETAILED DISCLOSURE OF THE INVENTION

Carbohydrate binding domain (CBD) containing enzymes of the invention may, in particular, be derivable from strains of Humicola, e.g. *Humicola insolens*, Fusarium, e.g. *Fusarium oxysporum*, or Myceliopthora, e.g. *Myceliopthora thermophile*.

Some of the variations in the amino acid sequence shown above appear to be "conservative", i.e. certain amino acids are preferred in these positions among the various CBD-containing enzymes of the invention. Thus, in position 1 of the sequence shown above, the amino acid is preferentially Trp or Tyr. In position 2, the amino acid is preferentially Gly or Ala. In position 7, the amino acid is preferentially Gln, Ile or Asn. In position 8, the amino acid is preferentially Gly or Asn. In position 9, the amino acid is preferentially Trp, Phe or Tyr. In position 10, the amino acid is preferentially Ser, Asn, Thr or Gln. In position 12, the amino acid is preferentially Pro, Ala or Cys. In position 13, the amino acid is preferentially Thr, Arg or Lys. In position 14, the amino acid is preferentially Thr, Cys or Asn. In position 18, the amino The cellulose- or hemicellulose-degrading enzyme of the invention may further comprise an amino acid sequence which defines a linking B region (to use the nomenclature established for *T. reesei* cellulases) adjoining the carbohydrate binding domain and connecting it to the catalytically active domain of the enzyme. The B region sequences established so far for enzymes of the invention indicate that such sequences are characterized by being predominantly hydrophilic and uncharged, and by being enriched in certain amino acids, in particular glycine and/or asparagine and/or proline and/or serine and/or threonine and/or glutamine. This characteristic structure of the B region imparts flexibility to the sequence, in particular in sequences containing short, repetitive units of primarily glycine and asparagine. Such repeats are not found in the B region sequences of *T. reesei* or *P. chrysosporium* which contain B regions of the serine/threonine type. The flexible structure is believed to facilitate the action of the catalytically active domain of the enzyme bound by the A region to the insoluble substrate, and therefore imparts advantageous properties to the enzyme of the invention.

Specific examples of B regions contained in enzymes of the invention have the following amino acid sequences Ala Arg Thr Asn Val Gly Gly Gly Ser Thr Gly Gly Gly Asn Asn Gly Gly Gly Asn Asn Gly
Gly Asn Pro Gly Gly Asn Pro Gly Gly Asn Pro Gly Gly Asn Pro Gly Gly Asn Pro Gly Gly
Asn Pro Gly Gly Asn Cys Ser Pro Leu (SEQ ID NO:12);

Pro Gly Gly Asn Asn Asn Asn Pro Pro Pro Ala Thr Thr Ser Gln Trp Thr Pro Pro Pro Ala
Gln Thr Ser Ser Asn Pro Pro Pro Thr Gly Gly Gly Gly Gly Asn Thr Leu His Glu Lys
(SEQ ID NO:13);

Gly Gly Ser Asn Asn Gly Gly Gly Asn Asn Asn Gly Gly Gly Asn Asn Asn Gly Gly Gly Gly
Asn Asn Asn Gly Gly Gly Asn Asn Asn Gly Gly Gly Asn Thr Gly Gly Gly Ser Ala Pro Leu
(SEQ ID NO:14);

Val Phe Thr Cys Ser Gly Asn Ser Gly Gly Gly Ser Asn Pro Ser Asn Pro Asn Pro Pro Thr
Pro Thr Thr Phe Ile Thr Gln Val Pro Asn Pro Thr Pro Val Ser Pro Pro Thr Cys Thr Val Ala
Lys (SEQ ID NO:15);

Pro Ala Leu Trp Pro Asn Asn Asn Pro Gln Gln Gly Asn Pro Asn Gln Gly Gly Asn Asn Gly
Gly Gly Asn Gln Gly Gly Gly Asn Gly Gly Cys Thr Val Pro Lys (SEQ ID NO:16);

Pro Gly Ser Gln Val Thr Thr Ser Thr Thr Ser Ser Ser Ser Thr Thr Ser Arg Ala Thr Ser Thr
Thr Ser Ala Gly Gly Val Thr Ser Ile Thr Thr Ser Pro Thr Arg Thr Val Thr Ile Pro Gly Gly
Ala Ser Thr Thr Ala Ser Tyr Asn (SEQ ID NO:17);

Glu Ser Gly Gly Gly Asn Thr Asn Pro Thr Asn Pro Thr Asn Pro Thr Asn Pro Thr Asn Pro
Thr Asn Pro Trp Asn Pro Gly Asn Pro Thr Asn Pro Gly Asn Pro Gly Gly Gly Asn Gly Gly
Asn Gly Gly Asn Cys Ser Pro Leu (SEQ ID NO:18); or

Pro Ala Val Gln Ile Pro Ser Ser Ser Thr Ser Ser Pro Val Asn Gln Pro Thr Ser Thr Ser Thr
Thr Ser Thr Ser Thr Thr Ser Ser Pro Pro Val Gln Pro Thr Thr Pro Ser Gly Cys Thr Ala Glu
Arg (SEQ ID NO:19).

In another aspect, the present invention relates to a carbohydrate binding domain homologous to a terminal A region of *Trichoderma reesei* cellulases, which carbohydrate binding domain comprises the following amino acid sequence

```
1                                    10
Xaa Xaa Gln Cys Gly Gly Xaa Xaa Xaa Xaa Gly Xaa Xaa Xaa Cys Xaa
            20                              30
Xaa Xaa Xaa Xaa Cys Xaa Xaa Xaa Asn Xaa Xaa Tyr Xaa Gln Cys Xaa

Xaa (SEQ ID NO:1)
``` or a subsequence thereof capable of effecting binding of a protein to an insoluble cellulosic or hemicellulosic substrate.

Examples of specific carbohydrate binding domains are those with the amino acid sequence indicated above.

In a further aspect, the present invention relates to a linking B region derived from a cellulose- or hemicellulose-degrading enzyme, said region comprising an amino acid sequence enriched in the amino acids glycine and/or asparagine and/or proline and/or serine and/or threonine and/or glutamine. As indicated above, these amino acids may often occur in short, repetitive units. Examples of specific B region sequences are those shown above.

The present invention provides a unique opportunity to "shuffle" the various regions of different cellulose- or hemicellulose-degrading enzymes, thereby creating novel combinations of the CBD, B region and catalytically active domain resulting in novel activity profiles of this type of enzymes. Thus, the enzyme of the invention may be one which comprises an amino acid sequence defining a CBD, which amino acid sequence is derived from one naturally occurring cellulose- or hemicellulose-degrading enzyme, an amino acid sequence defining a linking B region, which amino acid sequence is derived from another naturally occurring cellulose- or hemicellulose-degrading enzyme, as well as a catalytically active domain derived from the enzyme supplying either the CBD or the B region or from a third enzyme. In a particular embodiment, the catalytically active domain is derived from an enzyme which does not, in nature, comprise any CBD or B region. In this way, it is possible to construct enzymes with improved binding properties from enzymes which lack the CBD and B regions.

The enzyme of the invention is preferably a cellulase such as an endoglucanase (capable of hydrolyzing amorphous regions of low crystallinity in cellulose fibres), a cellobiohydrolase (also known as an exoglucanase, capable of initiating degradation of cellulose from the non-reducing chain ends by removing cellobiose units) or a β-glucosidase.

In a still further aspect, the present invention relates to a DNA construct which comprises a DNA sequence encoding a cellulose- or hemicellulose-degrading enzyme as described above.

A DNA sequence encoding the present enzyme may, for instance, be isolated by establishing a cDNA or genomic library of a microorganism known to produce cellulose- or hemicellulose-degrading enzymes, such as a strain of Humicola, Fusarium or Myceliopthora, and screening for positive clones by conventional procedures such as by hybridization to oligonucleotide probes synthesized on the basis of the full or partial amino acid sequence of the enzyme or probes based on the partial or full DNA sequence of the A region from *T. reesei* cellulases, as indicated above, or by selecting for clones expressing the appropriate enzyme activity, or by selecting for clones producing a protein which is reactive with an antibody raised against a native cellulose- or hemicellulose-degrading enzyme.

Alternatively, the DNA sequence encoding the enzyme may be prepared synthetically by established standard methods, e.g. the phosphoramidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoramidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. Thus, it may be envisaged that a DNA sequence encoding the CBD of the enzyme may be of genomic origin, while the DNA sequence encoding the B region of the enzyme may be of synthetic origin, or vice versa; the DNA sequence encoding the catalytically active domain of the enzyme may conveniently be of genomic or cDNA origin. The DNA construct may also be prepared by polymerase chain reaction using specific primers, for instance as described in U.S. Pat. No. 4,683,202 or R. K. Saiki et al., *Science* 239, 1988, pp. 487–491.

The present invention also relates to an expression vector which carries an inserted DNA construct as described above. The expression vector may suitably comprise appropriate promotor, operator and terminator sequences permitting the enzyme to be expressed in a particular host organism, as well as an origin of replication enabling the vector to replicate in the host organism in question.

The resulting expression vector may then be transformed into a suitable host cell, such as a fungal cell, a preferred example of which is a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238,023 (of Novo Industri A/S), the contents of which are hereby incorporated by reference.

Alternatively, the host organisms may be a bacterium, in particular strains of Streptomyces and Bacillus, and *E. coli*. The transformation of bacterial cells may be performed according to conventional methods, e.g. as described in Sambrook et al., *Molecular Cloning: A Laboratory Manual*, Cold Spring Harbor, 1989.

The screening of appropriate DNA sequences and construction of vectors may also be carried out by standard procedures, cf. Sambrook et al., op. cit.

The invention further relates to a method of producing a cellulose- or hemicellulose-degrading enzyme as described above, wherein a cell transformed with the expression vector of the invention is cultured under conditions conducive to the production of the enzyme, and the enzyme is subsequently recovered from the culture. The medium used to culture the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of fermentation and mutation or other techniques which are well known in the art, it is possible to provide cellulose- or hemicellulose-degrading enzymes of a high purity and in a high yield.

The present invention further relates to an agent for degrading cellulose or hemicellulose, the agent comprising a cellulose- or hemicellulose-degrading enzyme as described above. It is contemplated that, dependent on the specificity of the enzyme, it may be employed for one (or possibly more) of the applications mentioned above. In a particular embodiment, the agent may comprise a combination of two or more enzymes of the invention or a combination of one or more enzymes of the invention with one or more other enzymes with cellulose- or hemicellulose-degrading activity.

BRIEF DESCRIPTION OF THE DRAWINGS

FIG. 11 shows the DNA sequence and derived amino acid sequence of *F. oxysporum* C-family cellobiohydrolase (SEQ ID NO:20);

FIG. 12 shows the DNA sequence and derived amino acid sequence of *F. oxysporum* F-family cellulase (SEQ ID NO:22);

FIG. 13 shows the DNA sequence and derived amino acid sequence of *F. oxysporum* C-family endoglucanase (SEQ ID NO:24);

FIGS. 14.A–E show the DNA sequence and derived amino acid sequence of *H. insolens* endoglucanase 1(EG1) (SEQ ID NO:26); and FIGS. 15A–D show the DNA sequence and derived amino acid sequence of a fusion of the *B. lautus* (NCIMB 40250) Endo 1 catalytic domain and the CBD and B region of *H. insolens* ~43 kD endoglucanase (SEQ ID NO:28).

Figure 1:
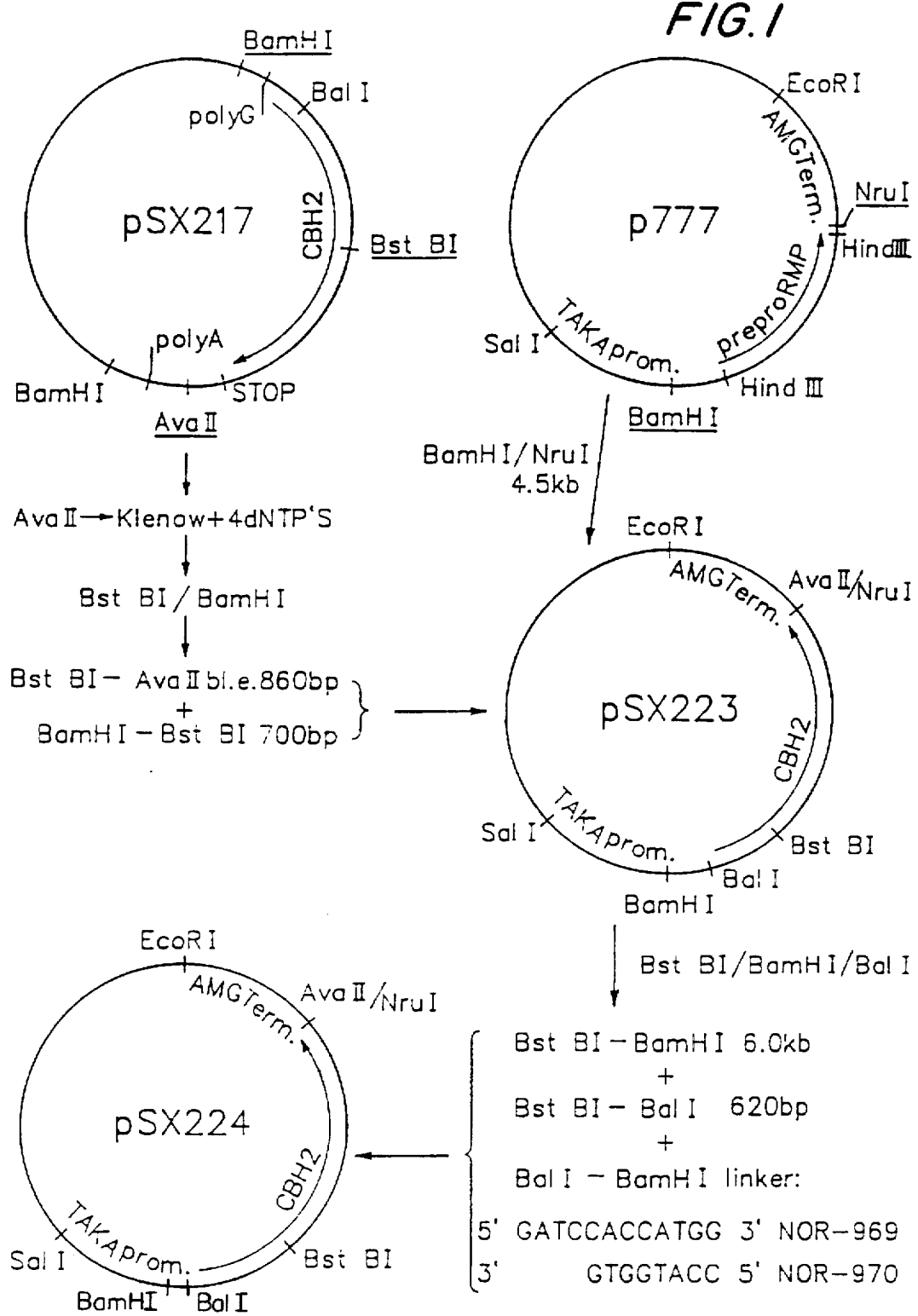
FIG. 1 shows the construction of plasmid p SX224.

The invention is further illustrated in the following examples which are not in any way intended to limit the scope of the invention as claimed.

EXAMPLE 1

Isolation of A Region-Containing Clones from *H. Insolens*

From *H. insolens* strain DSM 1800 (described in, e.g. WO 89/09259) grown on cellulose, mRNA was prepared according to the method described by Kaplan et al., *Biochem. J.* 183 (1979) 181–184. A cDNA library containing 20,000 clones was obtained substantially by the method of Okayama and Berg, *Methods in Enzymology* 154, 1987, pp. 3–28.

The cDNA library was screened as described by Gergen et al., *Nucl. Acids Res.* 7(8), 1979, pp. 2115–2136, with oligonucleotide probes in the antisense configuration, designed according to the published sequences of the N-terminal part of the A-region of the four *T. reesei* cellulase genes (Penttilä et al., Gene 45 (1986), 253–63; Saloheimo et al., Gene 63, (1988), 11–21; Shoemaker et al., Biotechnology, October 1983, 691–696; Teeri et al., Gene 51 (1987) 43–52. The probe sequences were as follows:

| | |
|---|---|
| NOR-804 (~EG 1) | 5'-CTT GCA CCC GCT GTA CCC AAT GCC ACC GCA CTG CCC CCA-3' (SEQ ID NO:30) |
| NOR-805 1) | 5'-CGT GGG GCC GCT GTA GCC AAT ACC GCC GCA CTG GCC (~CBH GTA-3' (SEQ ID NO:31) |
| NOR-807 2) | 5'-AGT CGG ACC CGA CCA ATT CTG GCC ACC ACA TTG GCC (~CBH CCA-3' (SEQ ID NO:32) |
| NOR-808 3) | 5'-CGT AGG TCC GCT CCA ACC AAT ACC TCC ACA CTG GCC (~EG CCA-3' (SEQ ID NO:33) |

Screening yielded a large number of candidates hybridising well to the A-region probes. Restriction mapping reduced the number of interesting clones to 17, of which 8 have so far been sequenced (as described by Haltiner et al., Nucl. Acids Res. 13, 1985, pp. 1015–1025) sufficiently to confirm the presence of a terminal CBD as well as a B-region.

The deduced amino acid sequences obtained for the CBDs were as follows

| | |
|---|---|
| A-1: | Trp Gly Gln Cys Gly Gly Gln Gly Trp Asn Gly Pro Thr Cys Cys Glu Ala Gly Thr Thr Cys Arg Gln Gln Asn Gln Trp Tyr Ser Gln Cys Leu (SEQ ID NO:2); |
| A-5: | Trp Gly Gln Cys Gly Gly Ile Gly Trp Asn Gly Pro Thr Thr Cys Val Ser Gly Ala Thr Cys Thr Lys Ile Asn Asp Trp Tyr His Gln Cys Leu (SEQ ID NO:3); |
| CBH-2: | Trp Gly Gln Cys Gly Gly Ile Gly Phe Asn Gly Pro Thr Cys Cys Gln Ser Gly Ser Thr Cys Val Lys Gln Asn Asp Trp Tyr Ser Gln Cys Leu (SEQ ID NO:4); |
| A-8: | Trp Gly Gln Cys Gly Gly Asn Gly Tyr Ser Gly Pro Thr Thr Cys Ala Glu Gly - Thr Cys Lys Lys Gln Asn Asp Trp Tyr Ser Gln Cys Thr Pro (SEQ ID NO:5); |
| A-9: | Trp Gly Gln Cys Gly Gly Gln Gly Trp Gln Gly Pro Thr Cys Cys Ser Gln Gly - Thr Cys Arg Ala Gln Asn Gln Trp Tyr Ser Gln Cys Leu Asn (SEQ ID NO:6); |
| A-11: | Trp Gly Gln Cys Gly Gly Gln Gly Tyr Ser Gly Cys Thr Asn Cys Glu Ala Gly Ser Thr Cys Arg Gln Gln Asn Ala Tyr Tyr Ser Gln Cys Ile (SEQ ID NO:7); |
| A-19: | Trp Gly Gln Cys Gly Gly Gln Gly Tyr Ser Gly Cys Arg Asn Cys Glu Ser Gly Ser Thr Cys Arg Ala Gln Asn Asp Trp Tyr Ser Gln Cys Leu (SEQ ID NO:8); and |
| ~43 kD: | Trp Ala Gln Cys Gly Gly Asn Gly Trp Ser Gly Cys Thr Thr Cys Val Ala Gly Ser Thr Cys Thr Lys Ile Asn Asp Trp Tyr His Gln Cys Leu (SEQ ID NO:9). |

The deduced amino acid sequences obtained for the B region were as follows

| | |
|---|---|
| A1: | Ala Arg Thr Asn Val Gly Gly Gly Ser Thr Gly Gly Gly Asn Asn Gly Gly Gly Asn Asn Gly Gly Asn Pro Gly Gly Asn Pro Gly Gly Asn Pro Gly Gly Asn Pro Gly Gly Asn Pro Gly Gly Asn Pro Gly Gly Asn Cys Ser Pro Leu (SEQ ID NO: 12); |
| A5: | Pro Gly Gly Asn Asn Asn Asn Pro Pro Pro Ala Thr Thr Ser Gln Trp Thr Pro Pro Pro Ala Gln Thr Ser Ser Asn Pro Pro Pro Thr Gly Gly Gly Gly Gly Asn Thr Leu His Glu Lys (SEQ ID NO:13); |
| A8: | Gly Gly Ser Asn Asn Gly Gly Gly Asn Asn Asn Gly Gly Gly Asn Asn Asn Gly Gly Gly Gly Asn Asn Asn Gly Gly Gly Asn Asn Asn Gly Gly Gly Asn Thr Gly Gly Gly Ser Ala Pro Leu (SEQ ID NO:14); |
| A11: | Val Phe Thr Cys Ser Gly Asn Ser Gly Gly Gly Ser Asn Pro Ser Asn Pro Asn Pro Pro Thr Pro Thr Thr Phe Ile Thr Gln Val Pro Asn Pro Thr Pro Val Ser Pro Pro Thr Cys Thr Val Ala Lys (SEQ ID NO:15); |
| A19: | Pro Ala Leu Trp Pro Asn Asn Asn Pro Gln Gln Gly Asn Pro Asn Gln Gly Gly Asn Asn Gly Gly Gly Asn Gln Gly Gly Gly Asn Gly Gly Cys Thr Val Pro Lys (SEQ ID NO: 16); |
| CBH2: | Pro Gly Ser Gln Val Thr Thr Ser Thr Thr Ser Ser Ser Ser Thr Thr Ser Arg Ala Thr Ser Thr Thr Ser Ala Gly Gly Val Thr Ser Ile Thr Thr Ser Pro Thr Arg Thr Val Thr Ile Pro Gly Gly Ala Ser Thr Thr Ala Ser Tyr Asn (SEQ ID NO: 17); |
| A9: | Glu Ser Gly Gly Gly Asn Thr Asn Pro Thr Asn Pro Thr Asn Pro Thr Asn Pro Thr Asn Pro Thr Asn Pro Trp Asn Pro Gly Asn Pro Thr Asn Pro Gly Asn Pro Gly Gly Asn Gly Gly Asn Gly Gly Asn Cys Ser Pro Leu (SEQ ID NO:18); or |
| | Pro Ala Val Gln Ile Pro Ser Ser Ser Thr Ser Ser Pro Val Asn Gln Pro Thr Ser Thr Ser Thr |

Thr Ser Thr Ser Thr Thr Ser Ser Pro Pro Val Gln Pro Thr Thr Pro Ser Gly Cys Thr Ala Glu Arg (SEQ ID NO:19).

EXAMPLE 2

Expression in *A. oryzae* of a CBH 2-type Cellulase from *H. insolens*

The complete sequence of one of the CBD clones shows a striking similarity to a cellobiohydrolase (CBH 2) from *T. reesei*.

The construction of the expression vector pSX224 carrying the *H. insolens* CBH 2 gene for expression in and secretion from *A. oryzae* is outlined in FIG. 1. The vector p777 containing the pUC 19 replicon and the regulatory regions of the TAKA amylase promoter from *A. oryzae* and glucoamylase terminator from *A. niger* is described in EP 238 023. pSX 217 is composed of the cloning vector pcDV1-pL1 (cf. Okayama and Berg, op. cit.) carrying the *H. insolens* CBH 2 gene on a 1.8 kb fragment. The CBH 2 gene contains three restriction sites used in the construction: A BalI site at the initiating methionine codon in the signal sequence, a BstBI site 620 bp downstream from the BalI site and an AvaII site 860 bp downstream from the BstBI site. The AvaII site is located in the non-translated C-terminal part of the gene upstream of the poly A region, which is not wanted in the final construction. Nor is the poly G region upstream of the gene in the cloning vector. This region is excised and replaced by an oligonucleotide linker which places the translational start codon close to the BamHI site at the end of the TAKA promoter.

The expression vector pSX 224 was transformed into *A. oryzae* IFO 4177 using the amdS gene from *A. nidulans* as the selective marker as described in EP 238 023. Transformants were grown in YPD medium (Sherman et al., Methods in Yeast Genetics, Cold Spring Harbor Laboratory, 1981) for 3–4 days and analysed for new protein species in the supernatant by sodium dodecyl sulphate polyacrylamide gel electrophoresis. The CBH 2 from *H. insolens* formed a band with an apparent Mw of 65 kD indicating a substantial glycosylation of the protein chain, which is calculated to have a Mw of 51 kD on the basis of the amino acid composition. The intact enzyme binds well to cellulose, while enzymatic degradation products of 55 kD and 40 kD do not bind, indicating removal of the A-region and possibly the B-region. The enzyme has some activity towards filter paper, giving rise to release of glucose. As expected, it has very limited endoglucanase activity as measured on soluble cellulose in the form of carboxy methyl cellulose.

EXAMPLE 3

Isolation of *Fusarium Oxysporum* Genomic DNA

A freeze-dried culture of *Fusarium oxysporum* was reconstituted with phosphate buffer, spotted 5 times on each of 5 FOX medium plates (6% yeast extract, 1.5% $K_2HPO_4$, 0.75% $MgSO_4$ $7H_2O$, 22.5% glucose, 1.5% agar, pH 5.6) and incubated at 37° C. After 6 days of incubation the colonies were scraped from the plates into 15 ml of 0.001% Tween-80 which resulted in a thick and cloudy suspension.

Four 1-liter flasks, each containing 300 ml of liquid FOX medium, were inoculated with 2 ml of the spore suspension and were incubated at 30° C. and 240 rpm. On the 4th day of incubation, the cultures were filtered through 4 layers of sterile gauze and washed with sterile water. The mycelia were dried on Whatman filter paper, frozen in liquid nitrogen, ground into a fine powder in a cold mortar and added to 75 ml of fresh lysis buffer (10 mM Tris-Cl 7.4, 1% SDS, 50 mM EDTA, 100 µl DEPC). The thoroughly mixed suspension was incubated in a 65° C. waterbath for 1 hour and then spun for 10 minutes at 4000 rpm and 5° C. in a bench-top centrifuge. The supernatant was decanted and EtOH precipitated. After 1 hour on ice the solution was spun at 19,000 rpm for 20 minutes. The supernatant was decanted and isopropanol precipitated. Following centrifugation at 10,000 rpm for 10 minutes, the supernatant was decanted and the pellets allowed to dry.

One milliliter of TER solution (10 mM Tris-HCl, pH 7.4, 1 mM EDTA, 100 µg RNAse A) was added to each tube, and the tubes were stored at 4° C. for two days. The tubes were pooled and placed in a 65° C. waterbath for 30 minutes to suspend non-dissolved DNA. The solution was extracted twice with phenol/$CHCl_3$/isoamyl alcohol, twice with $CHCl_3$/isoamyl alcohol and then ethanol precipitated. The pellet was allowed to settle and the EtOH was removed. 70% EtOH was added and the DNA stored overnight at −20° C. After decanting and drying, 1 ml of TER was added and the DNA was dissolved by incubating the tubes at 65° C. for 1 hour. The preparation yielded 1.5 mg of genomic DNA.

Amplification, Cloning and Sequencing of DNA Amplified with Degenerate Primers

To amplify DNA from C-family (according to the nomenclature of Henrissat et al. *Gene* 81 (1), 1989, pp. 83–96) cellulases using PCR (cf. U.S. Pat. No. 4,683,195 and U.S. Pat. No. 4,683,202) each "sense" oligonucleotide was used in combination with each "antisense" oligonucleotide. Thus, the following primer pair was used:

| Primer 1 | Primer 2 |
| --- | --- |
| ZC3220 | ZC3221 |

ZC3220: GCC AAC TAC GGT ACC GG(A/C/G/T) TA(C/T) TG(C/T) GA(C/T) (A/G/T)(C/G)(A/G/C/T) CA(G/A) TG (SEQ ID NO:34)
ZC3221: GCG TTG GCC TCT AGA AT(G/A) TCC AT(C/T) TC(A/G/C/T) (C/G/T)(A/T)(G/A) CA(G/A) CA (SEQ ID NO:35)

In the PCR reaction, 1 µg of *Fusarium oxysporum* genomic DNA was used as the template. Ten times PCR buffer is 100mM Tris-HCl pH 8.3, 500 mM KCl, 15 mM $MgCl$, 0.1% gelatin (Perkin-Elmer Cetus). The reactions contained the following ingredients:

| | |
| --- | --- |
| dH2O | 35.75 µl |
| 10X PCR buffer | 5 µl |
| template DNA | 5 µl |
| primer 1 | 2 µl (40 pmol) |
| primer 2 | 2 µl (40 pmol) |
| Taq polymerase | 0.25 µl (1.25 U) |
| total | 50 µl |

The PCR reactions were performed for 40 cycles under the following conditions:

| | |
| --- | --- |
| 94° C. | 1.5 min |
| 45° | 2.0 min |
| 72° | 2.0 min |

Five microliters of each reaction was analyzed by agarose gel electrophoresis. The sizes of the DNA fragments were estimated from DNA molecular weight markers. The reacton primed with ZC3220 and ZC3221, produced two DNA fragments of appropriate size to be candidates for fragments of C-family cellulases. The agarose sections containing these two fragments were excised, and the DNA was electroeluted and digested with the restriction enzymes Kpnl and Zbal. The fragments were ligated into the vector pUC18 which had been cut with the same two restriction enzymes. The ligations were transformed into *E. coli* and mini-prep DNA was prepared from the resulting colonies. The DNA sequences of these inserts were determined and revealed that two new C-family cellulases had been identified, one a new cellobiohydrolase and the other a new endoglucanase.

The PCR cloning strategy described above for the C-family cellulases was applied using other primers which encoded conserved cellulase sequences within the known F-family cellulases (cf. Henrissat et al., op. cit.). The following primer pair was used for amplification of Fusarium genomic DNA.

| Primer 1 | Primer 2 |
| --- | --- |
| ZC3226 | ZC3227 |

ZC3226: TCC TGA CGC CAA GCT TT(A/G/T) (C/T)(A/T)(A/T) (A/C/T) AA (C/T)GA (C/T)TA (C/T)AA (SEQ ID NO:36)
ZC3227: CAC CGG CAC CAT CGA T(G/A/)T C(A/C/G/T)A (G/A)(C/T)T C(A/G/C/T)G T(A/G/T)A T (SEQ ID NO:37)

The PCR reactions were performed for 40 cycles as follows:

| 94° C. | 1.5 min |
| --- | --- |
| 50° C. | 2.0 min |
| 72° C. | 2.0 min |

The 180 bp band was eluted from an agarose gel fragment, digested with the restriction enzymes Hind III and Cla I and ligated into pUC19 which had been digested with Hind III and AccI. The ligated DNA was transformed into *E. coli* and mini-prep DNA was prepared from colony isolates. The DNA sequence of the cloned DNA was determined. This fragment encoded sequences corresponding to a new member of the F-family cellulases.

Construction of a *Fusarium oxysporum* cDNA Library

*Fusarium oxysporum* was grown by fermentation and samples were withdrawn at various times for RNA extraction and cellulase activity analysis. The activity analysis included an assay for total cellulase activity as well as one for colour clarification. *Fusarium oxysporum* samples demonstrating maximal colour clarification were extracted for total RNA from which poly(A)+RNA was isolated.

To construct a *Fusarium oxysporum* cDNA library, first-strand cDNA was synthesized in two reactions, one with and the other without radiolabelled dATP. A 2.5× reaction mixture was prepared at room temperature by mixing the following reagents in the following order: 10 µl of 5× reverse transcriptase buffer (Gibco-BRL, Gaithersburg, Maryland) 2.5 µl 200 mM dithiothreitol (made fresh or from a stock solution stored at −70° C.), and 2.5 µl of a mixture containing 10 mM of each deoxynucleotide triphosphate, (dATP, dGTP, dTTP and 5-methyl dCTP, obtained from Pharmacia LKB Biotechnology, Alameda, Calif.). The reaction mixture was divided into each of two tubes of 7.5 µl. 1.3 µl of 10 µCi/µl $^{32}P$ α-dATP (Amersham, Arlington Heights, Ill.) was added to one tube and 1.3 µl of water to the other. Seven microliters of each mixture was transferred to final reaction tubes. In a separate tube, 5 µg of *Fusarium oxysporum* poly (A)+RNA in 14 µl of 5 mM Tris-HCl pH 7.4, 50 µM EDTA was mixed with 2 µl of 1 µg/µl first strand primer (ZC2938GACAGAGCACAGAATTCACTAGTGAGCTCT$_{15}$ (SEQ ID NO:38)). The RNA-primer mixture was heated at 65° C. for 4 minutes, chilled in ice water, and centrifuged briefly in a microfuge. Eight microliters of the RNA-primer mixture was added to the final reaction tubes. Five microliters of 200 U/µl Superscript™ reverse transcriptase (Gibco-BRL) was added to each tube. After gentle agitation, the tubes were incubated at 45° C. for 30 minutes. Eighty microliters of 10 mM Tris-HCl pH 7.4, 1 mM EDTA was added to each tube, the samples were vortexed, and briefly centrifuged. Three microliters was removed from each tube to determine counts incorporated by TCA precipitation and the total counts in the reaction. A 2 µl sample from each tube was analyzed by gel electrophoresis. The remainder of each sample was ethanol precipitated in the presence of oyster glycogen. The nucleic acids were pelleted by centrifugation, and the pellets were washed with 80% ethanol. Following the ethanol wash, the samples were air dried for 10 minutes. The first strand synthesis yielded 1.6 µg of Fusarium oxysporum cDNA, a 33% conversion of poly(A)+RNA into DNA.

Second strand cDNA synthesis was performed on the RNA-DNA hybrid from the first strand reactions under conditions which encouraged first strand priming of second strand synthesis resulting in hairpin DNA. The first strand products from each of the two first strand reactions were resuspended in 71 µl of water. The following reagents were added, at room temperature, to the reaction tubes: 20 µl of 5× second strand buffer (100 mM Tris pH 7.4, 450 mM KCl, 23 mM $MgCl_2$, and 50 mM $(NH_4)_2(SO_4)$, 3 µl of 5 mM β-NAD, and µl of a deoxynucleotide triphosphate mixture with each at 10 mM. One microliter of α-$^{32}P$ dATP was added to the reaction mixture which received unlabeled dATP for the first strand synthesis while the tube which received labeled dATP for first strand synthesis received 1 µl of water. Each tube then received 0.6 µl of 7 U/µl *E. coli* DNA ligase (Boehringer-Mannheim, Indianapolis, Ind.), 3.1 µl of 8 U/µl *E. coli* DNA polymerase I (Amersham), and 1 µl 2 U/µl of RNase H (Gibco-BRL). The reactions were incubated at 16° C. for 2 hours. After incubation, 21 µl from each reaction was used to determine TCA precipitable counts and total counts in the reaction, and 2 µl from each reaction was analyzed by gel electrophoresis. To the remainder of each sample, 2 µl of 2.5 µg/µl oyster glycogen, 5 µl of 0.5 EDTA and 200 µl of 10 mM Tris-HCl pH 7.4, 1 mM EDTA were added. The samples were phenol-chloroform extracted and isopropanol precipitated. After centrifugation the pellets were washed with 100 µl of 80% ethanol and air dried. The yield of double stranded cDNA in each of the reactions was approximately 2.5 µg.

Mung bean nuclease treatment was used to clip the single-stranded DNA of the hair-pin. Each cDNA pellet was resuspended in 15 µl of water and 2.5 µl of 10× mung bean buffer (0.3M NaAc pH 4.6, 3M NaCl, and 10 mM $ZnSO_4$), 2.5 µl of 10 mM DTT, 2.5 µl of 50% glycerol, and 2.5 µl of 10 U/µl mung bean nuclease (New England Biolabs, Beverly, Mass.) were added to each tube. The reactions were incubated at 30° C. for 30 minutes and 75 µl of 10 mM Tris-HCl pH 7.4 and 1 mM EDTA was added to each tube. Two-microliter aliquots were analyzed by alkaline agarose gel analysis. One hundred microliters of 1M Tris-HCl pH 7.4 was added to each tube and the samples were phenol-chloroform extracted twice. The DNA was isopropanol precipitated and pelleted by centrifugation. After centrifugation, the DNA pellet was washed with 80% ethanol and air dried. The yield was approximately 2 μg of DNA from each of the two reactions.

The cDNA ends were blunted by treatment with T4 DNA polymerase. DNA from the two samples were combined after resuspension in a total volume of 24 μl of water. Four microliters of 10× T4 buffer (330 mM Tris-acetate pH 7.9, 670 mM KAc, 100 mM MgAc, and 1 mg/ml gelatin), 4 μl of 1 mM dNTP, 4 μl 50 mM DTT, and 4 μl of 1 U/μl T4 DNA polymerase (Boehringer-Mannheim) were added to the DNA. The samples were incubated at 15° C. for 1 hour. After incubation, 160 μl of 10 mM Tris-HCl pH 7.4, 1 mM EDTA was added, and the sample was phenol-chloroform extracted. The DNA was isopropanol precipitated and pelleted by centrifugation. After centrifugation the DNA was washed with 80% ethanol and air dried.

After resuspension of the DNA in 6.5 μl water, Eco RI adapters were added to the blunted DNA. One microliter of 1 μg/μl Eco RI adapter (Invitrogen, San Diego, Calif. Cat. # N409-20), 1 μl of 10× ligase buffer (0.5M Tris pH 7.8 and 50 mM MgCl$_2$), 0.5 μl of 10 mM ATP, 0.5 μl of 100 mM DTT, and 1 μl of 1 U/μl T4 DNA ligase (Boehringer-Mannheim) were added to the DNA. After the sample was incubated overnight at room temperature, the ligase was heat denatured at 65° C. for 15 minutes.

The Sst I cloning site encoded by the first strand primer was exposed by digestion with Sst I endonuclease. Thirty-three microliters of water, 5 μl of 10× Sst I buffer (0.5M Tris pH 8.0, 0.1M MgCl$_2$, and 0.5M NaCi), and 2 μl of 5 U/μl Sst I were added to the DNA, and the samples were incubated at 37° C. for 2 hours. One hundred and fifty microliters of 10 mM Tris-HCl pH 7.4, 1 mM EDTA was added, the sample was phenol-chloroform extracted, and the DNA was isopropanol precipitated.

The cDNA was chromatographed on a Sepharose CL 2B (Pharmacia LKB Biotechnology) column to size-select the cDNA and to remove free adapters. A 1.1 ml column of Sepharose CL 2B was poured into a 1 ml plastic disposable pipet and the column was washed with 50 column volumes of buffer (10 mM Tris pH 7.4 and 1 mM EDTA). The sample was applied, one-drop fractions were collected, and the DNA in the void volume was pooled. The fractionated DNA was isopropanol precipitated. After centrifugation the DNA was washed with 80% ethanol and air dried.

A *Fusarium oxysporum* cDNA library was established by ligating the cDNA to the vector pYcDE8' (cf. WO 90/10698) which had been digested with Eco RI and Sst I. Three hundred and ninety nanograms of vector was ligated to 400 ng of cDNA in a 80 μl ligation reaction containing 8 μl of 10×ligase buffer, 4 μl of 10 mM ATP, 4 μl 200 mM DTT, and 1 unit of T4 DNA ligase (Boehringer-Mannheim. After overnight incubation at room temperature, 5 μg of oyster glycogen and 120 μl of 10 mM Tris-HCl and 1 mM EDTA were added and the sample was phenol-chloroform extracted. The DNA was ethanol precipitated, centrifuged, and the DNA pellet washed with 80% ethanol. After air drying, the DNA was resuspended in 3 μl of water. Thirty seven microliters of electroporation competent DH10B cells (Gibco-BRL) was added to the DNA, and electroporation was completed with a Bio-Rad Gene Pulser (Model #1652076) and Bio-Rad Pulse Controller (Model #1652098) electroporation unit (Bio-Rad Laboratories, Richmond, Calif.). Four milliliters of SOC (Hanahan, J. Mol. Biol. 166 (1983), 557–580) was added to the electroporated cells, and 400 μl of the cell suspension was spread on each of ten 150 mm LB amipicillin plates. After an overnight incubation, 10 ml of LB amp media was added to each plate, and the cells were scraped into the media. Glycerol stocks and plasmid preparations were made from each plate. The library background (vector without insert) was established at aproximately 1% by ligating the vector without insert and titering the number of clones after electroporation.

Screening the cDNA Library

Full length cellulase cDNA clones were isolated from the *Fusarium oxysporum* cDNA library by hybridization to PCR generated genomic oligonucleotide probes.

The PCR-generated oligonucleotides: ZC3309, a 40-mer coding for part of the C family cellobiohydrolase, ATT ACC AAC ACC AGC GTT GAC ATC ACT GTC AGA GGG CTT C; ZC3310 (SEQ ID NO:39), a 28-mer coding for the C family endoglucanase, AAC TCC GTT GAT GAA AGG AGT GAC GTA G (SEQ ID NO:40); and ZC3311, a 40-mer coding for the F family cellulase, CGG AGA GCA GCA GGA ACA CCA GAG GCA GGG TTC CAG CCA C (SEQ ID NO:41), were end labeled with T$_4$ polynucleotide kinase and $^{32}$P gamma ATP. For the kinase reaction 17 picomoles of each oligonucleotide were brought up to 12.5 μl volume with deionized water. To these were added 2 μl 10× kinase buffer (1×: 10 mM magnesium chloride, 0.1 mM EDTA, 50 mM Tris pH 7.8), 0.5 μl 200 mM dithiothreitol, 1 μl $^{32}$P gamma ATP 150 mCi/ml, Amersham), 2 μl T$_4$ polynucleotide kinase (10 U/μl BRL). The samples were then mixed and incubated at 37° C. for 30 minutes.

Oligonucleotides were separated from unincorporated nucleotides by precipitation with 180 μl TE (10 mM tris pH 8.0, 1 mM EDTA), 100 μl 7.5M ammonium acetate, 2 μl mussel glycogen (20 mg/ml, Gibco-BRL) and 750 μl 100% ethanol. Pellets where dissolved in 200 μl distilled water. To determine the amount of radioactivity incorporated in the oligonucleotides, 10 μl of 1: 1000 dilutions of oligonucleotides were read without scintillation fluid in a Beckman LS 1800 Liquid Scintillation System. Activities were: 115 million cpm for ZC3309, 86 million cpm for ZC33 10, and 79 million cpm for ZC3311.

Initially, a library of 20,000 cDNA clones was probed with a mixture of each of the three oligonucleotides corresponding to the C family cellobiohydrolase, C family endoglucanase and F family cellulase clones. The cDNA library was plated out from titered glycerol stocks stored at −70° C. Four thousand clones were plated out on each of five 150 mm LB ampicillin (1000 μg/ml) plates. Lifts were taken in duplicate following standard methodology Sambrook et al., *Molecular Cloning*, 1989) using Biotrans 0.2 μm 137 mm filters. The filters were baked at 80° C. in vacuum for 2 hours, then swirled overnight in a crystallizing dish (Pharmacia LKB Biotechnology, Alameda, Calif.) at 37° C. in 80 ml prehybridization solution (5×Denhardt's (1×: 0.02% Ficoll, 0.02% polyvinylpyrrolidone, 0.02% bovine serum albumen Pentax Fraction 5 (Sigma, St. Louis, Mo.)) 5×SSC (1×:0.15M sodium chloride, 0.15M sodium citrate pH 7.3)), 100 μl denatured sonicated salmon sperm DNA, 50 mM sodium phosphate pH 6.8, 1 mM sodium pyrophosphate, 100 μM ATP, 20% formamide, 1% sodium dodecyl sulfate) (Ulrich et al. EMBO J. 3 (1984), 361–364).

Prehybridized filters were probed by adding them one at a time into a crystallizing dish with 80 ml prehybridization solution with 80 million cpm ZC3309, 86 million cmp ZC3310 and 79 million cpm ZC3311 and then swirled overnight at 37° C. Filters were then washed to high stringency. The probed filters were washed with three 400 ml volumes of low stringency wash solution (2×SSC, 0.1% SDS) at room temperature in the crystallizing dish, then with four 1-liter volumes in a plastic box. A further wash for 20 minutes at 68° C. with tetramethylammonium chloride wash solution (TMACL: 3M tetramethylammonium chloride, 50 mM Tris-HCl pH 8.0, 2 mM EDTA, 1 g/l SDS) (Wood et al., Proc. Natl. Acad. Sci. 82, pp. 1585–88 (1985)) provided a high stringency wash for the 28-mer ZC3310 independent of its base composition 1585–1588). The filters were then blotted dry, mounted on Whatman 3MM paper and covered with plastic wrap for autoradiography. They were exposed overnight at −70° C. with intensifying screens and Kodak XAR-5 film.

Two putative positives appeared on duplicate filters. The corresponding areas on the plates with colonies were picked into 1 ml of 1× polymerase chain reaction (PCR) buffer (100 mM Tris HCl pH 8.3, 500 mM KCl, 15 mM MgCl, 0.1% gelatin; Perkin Elmer Cetus) and plated out at five tenfold dilutions on 100 mm LB plates with 70 µg/ml ampicillin. These plates were grown at 37° C. overnight. Two dilutions of each putative clone were chosen for rescreening as outlined above. One isolated clone, pZFH196 was found. This was grown up overnight in 10 ml 2× YT broth (per liter: 16 g bacto-tryptone, 10 g bacto-yeast extract, 10 g NaCl). Twenty three micrograms of DNA were purifified by the rapid boiling method (Holmes and Quigley, Anal. Biochem. 114 (1981), 193–197). From restriction analysis the clone was found to be approximately 2,000 base pairs in length. Sequence analysis showed it to contain a fragment homologous to the C family cellobiohydrolase fragment cloned by PCR.

In an attempt to isolate additional cellulase cDNA clones, a cDNA library of 2 million clones was plated out on 20 150 mm LB plates (100 µl ampicillin) containing approximately 100,000 cDNA clones. Lifts were taken in duplicate as in the first screening attempt. This library was screened with oligonucleotides corresponding to the three cellulase species as described above except that the hybridization was carried out with formamide in the prehybridization buffer and at a temperature of 30° C. Washing with TMACL was carried out twice for 20 minutes at 67° C. Between 8 and 20 signals were found on duplicate filters of each of the 20 plates. Fifteen plugs were taken from the first plate with the large end of a pasteur pipet into 1 ml 1× PCR buffer (Perkin-Elmer Cetus). PCR was carried out on the bacterial plugs with three separate oligonucleotide mixtures. Each mixture contained the vector specific oligonucleotide ZC2847 and additionally, a different cellulase specific oligonucleotide (ZC3309, ZC33 10 or ZC33 11) within each mixture. Amplitaq polymerase (Perkin-Elmer Cetus) was used with Pharmacia Ultrapure dNTP and following Perkin Elmer Cetus procedures. Sixteen picomoles of each primer were used in 40 µl reaction volumes. Twenty microliters of cells in 1×PCR buffer were added to 20 µl mastermix which contained everything needed for PCR except for DNA. After an initial 1 minute 45 second denaturation at 94° C. 28 cycles of: 45 seconds at 94° C., 1 minute at 45° C. and 2 minutes at 72° C. with a final extension of 10 minutes at 72° C. were employed in a Perkin Elmer thermocycler. Ten of the 15 plugs yielded a band when primed with the C family specific oligonucleotide ZC3309 and ZC2847. The other mixtures gave no specific products. Five plugs which produced the largest bands by PCR, therefore possibly being full length C family cellobiohydrolases, along with the 5 plugs which did not produce PCR bands, were plated out at five 10 fold dilutions onto 100 mm LB plates with 70 µg/ml ampicillin and grown overnight. Duplicate lifts were taken of two ten fold dilutions each. Prehybridization and hybridization were carried out as described above with a mixture of the 3 oligonucleotides. Isolated clones were found on all 10 of the platings. These were picked from the dilution plates with a toothpick for single colony isolation on 100 mm LB plates with 70 µg/ml ampicillin. PCR was carried out on isolated bacterial colonies with 2 oligonucleotides specific for the C family cellobiohydrolase (ZC3409 (CCG TTC TGG ACG TAC AGA (SEQ ID NO:50)) and ZC3411 (TGA TGT CAA GTT CAT CAA (SEQ ID NO:52))). Conditions were identical to those described above except for using 10 picomoles of each primer in 25 µl reaction volumes. Colonies were added by toothpick into PCR tubes with 25 µl mastermix before cycling. Five of the 10 gave strong bands of the size expected for a C family cellobiohydrolase. Isolated colonies were then grown up in 20 ml of Terrific Broth (Sambrook et al., op. cit., A2) and DNA was isolated by the rapid boiling method. The clones were partially sequenced by Sanger dideoxy sequencing. From sequence analysis the 5 clones which did not give bands specific for a C family cellobiohydrolase by PCR were shown to be F family cellulase clones.

In order to clone the C family endoglucanase, the cDNA library of 2 million clones was rescreened with only ZC3310. Conditions of prehybridization and hybridization were like those used above. Filters were hybridized for 10 hours at 30° C. with one million CPM endlabeled ZC3310 per ml prehybridization solution without formamide. Washing with TMACL was carried out 2 times for 20 minutes at 60° C. Seven weak signals were found on duplicate filters. Plugs were picked with the large end of a pipet into 1 ml LB broth. These were each plated out in 5–10 fold dilutions on 100 mm LB plates with 70 µg/ml ampicillin. Duplicate lifts were taken of 2 dilutions each and were processed as described above. Prehybridization, hybridization, and washing were carried out as for the first level of screening. Three isolated clones were identified and streaked out for single colony hybridization. Isolates were grown overnight in 50 ml of Terrific Broth (per liter: 12 g tryptone, 24 g yeast extract, 4 ml glycerol, autoclaved, and 100 ml of 0.17M $KH_2PO_4$, 0.72M $K_2HPO_4$ (Sambrook et al., op. cit., A2) and DNA was isolated by alkaline lysis and PEG precipitation by standard methods (Maniatis 1989, 1.38–1.41). From restriction analysis, one clone (pZFH223) was longer than the others and was chosen for complete sequencing. Sequence analysis showed it to contain the PCR fragment cloned initially.

DNA Sequence Analysis

The cDNAs were sequenced in the yeast expression vector pYCDE8'. The dideoxy chain termination method (F. Sanger et al., Proc. Natl. Acad. Sci. USA 74, 1977, pp. 5463–5467) using @35-S dATP from New England Nuclear (cf. M. D. Biggin et al., Proc. Natl. Acad. Sci. USA 80, 1983, pp. 3963–3965) was used for all sequencing reactions. The reactions were catalysed by modified t7 DNA polymerase from Pharmacia (cf. S. Tabor and C. C. Richardson, Proc. Natl. Acad. Sci. USA 84, 1987, pp. 4767–4771) and were primed with an oligonucleotide complementary to the ADH1 promoter (ZC996: ATT GTT CTC GTT CCC TTT CTT (SEQ ID NO:42)), complementary to the CYC1 terminator (ZC3635: TGT ACG CAT GTA ACA TTA (SEQ ID NO:43)) or with oligonucleotides complementary to the DNA of interest. Double stranded templates were denatured with NaOH (E. Y. Chen and P. H. Seeburg, DNA 4, 1985, pp. 165–170) prior to hybridizing with a sequencing oligonucleotide. Oligonucleotides were synthesized on an Applied Biosystems Model 380A DNA synthesizer. The oligonucleotides used for the sequencing reactions are listed in the sequencing oligonucleotide table below:

C-family cellobiohydrolase sequencing primers

ZC3411  TGA TGT CAA GTT CAT CAA (SEQ ID NO:44)
ZC3408  TCT GTA CGT CCA GAA CGG (SEQ ID NO:45)
ZC3407  ATG ACT TCT CTA AGA AGG (SEQ ID NO:46)
ZC3406  TCC AAC ATC AAG TTC GGT (SEQ ID NO:47)
ZC3410  AGG CCA ACT CCA TCT GAA (SEQ ID NO:48)
ZC3309  ATT ACC AAC ACC AGC GTT GAC ATC ACT GTC AGA GGG CTC C
        (SEQ ID NO:49)
ZC3409  CCG TTC TGG ACG TAC AGA (SEQ ID NO:50)

F-family cellulase specific sequencing primers

ZC3413  CCA TCG ACG GTA TTG GAT (SEQ ID NO:51)
ZC3311  CGG AGA GCA GCA GGA ACA CCA GAG GCA GGG TTC CAG CCA
        C (SEQ ID NO:52)
ZC3412  GAG GGT AGA GCG ATC GTT (SEQ ID NO:53)

C-family endoglucanase specific sequencing primers

ZC3739  TGA TCT CAT CGA GCT GCA CC (SEQ ID NO:54)
ZC3684  GTG ATG CTC AGT GCT ACG TC (SEQ ID NO:55)
ZC3310  AAC TCC GTT GAT GAA AGG AGT GAC GTA G (SEQ ID NO:56)
ZC3750  TCC AAT AGC TTC CCA GCA AG (SEQ ID NO:57)
ZC3683  TGT CCC TTG ATG TTG CCA AC (SEQ ID NO:58)

The DNA sequences of the full-length cDNA clones, as well as the derived amino acid sequences, are shown in the appended FIGS. 11 (C-family cellobiohydrolase), 12 (F-family cellulase) and 13 (C-family endoglucanase), corresponding to SEQ ID NOS:20, 22 and 24, respectively.

EXAMPLE 4

Isolation of Endoglucanase EGI Gene from *H. insolens*

The cDNA library described in example 1 was also screened with a 35 bp oligonucleotide probe in the antisense configuration with the sequence: NOR-770: 5' GCTTCGC-CCATGCCTTGGGTGGCGCCGAGTTCCAT 3' (SEQ ID NO:59)

The sequence was derived from the amino acid sequence of an alcalase fragment of EGI purified from *H. insolens*, using our knowledge of codon bias in this organism. Complete clones of 1.6 kb contained the entire coding sequence of 1.3 kb as shown in FIG. 14A–E (SEQ ID NO:26). The probe sequence NOR-770 is located at $Met_{344}$-$Ala_{355}$.

Construction of Expression Plasmids of EGI (full length) and EGI' (truncated)

Figure 2:
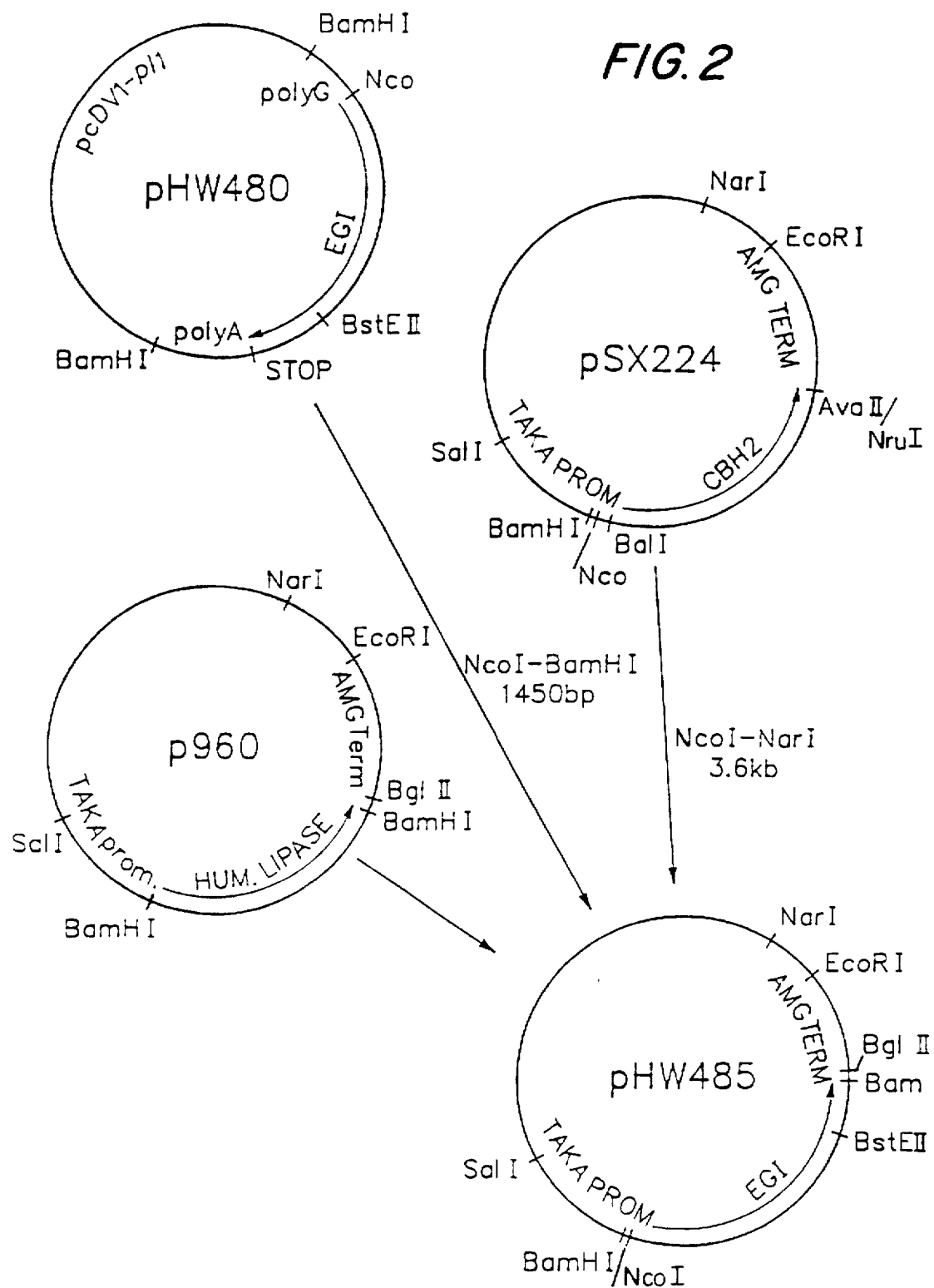
FIG. 2 shows the construction of plasmid pHW485.

The EGI gene still containing the poly-A tail was inserted into an *A. oryzae* expression plasmid as outlined in FIG. 2. The coding region of EGI was cut out from the NcoI-site in the initiating Met-codon to the BamH1-sit e downstream of the poly-A region as a 1450 bp fragment from pHW480. This was ligated to a 3.6 kb NcoI-NarI fragment from pSX224 (FIG. 1) containing the TAKA promoter and most of pUC19, and to a 960 bp NarI-BamHI fragment containing the remaining part with the AMG-terminator. The 960 bp fragment was taken from p960 which is equivalent to p777 (described in EP 238,023) except for the inserted gene. The resulting expression plasmid is termed pHW485.

Figure 3:
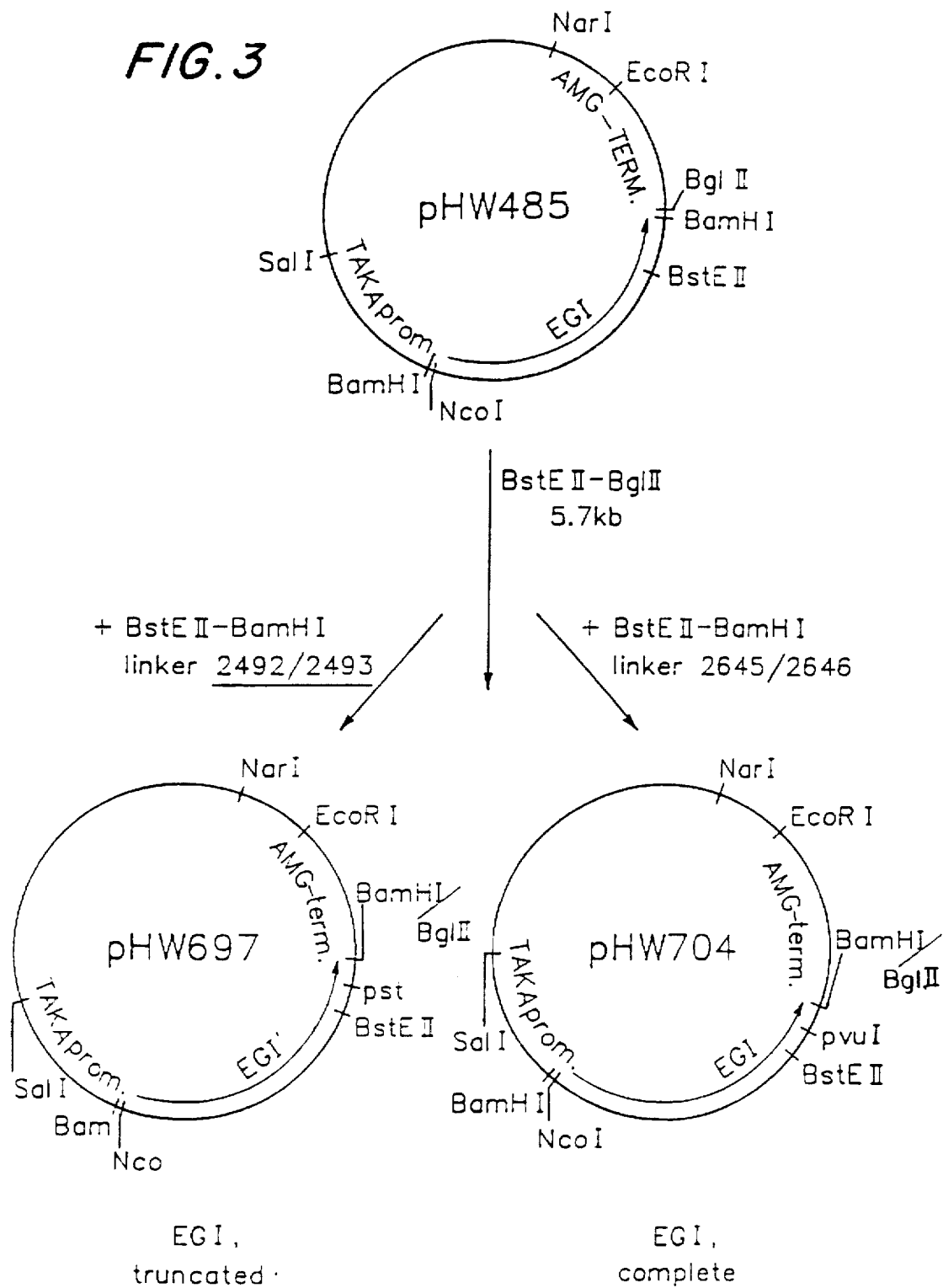
FIG. 3 shows the construction of plasmid pHW697 and pHW704.

The expression plasmid pHW704 with the full length EGI gene without poly A tail is shown in FIG. 3. From the BstEaII site 1300 bp downstream of the NcoI-site was inserted a 102 bp BstEII-BamHI linker (2645/2646) ligated to BglII-site in the vector. The linker contains the coding region downstream of BstEII-site with 2 stop codons at the end and a PvuI-sit e near the C-terminal to be used for addition of CBD and B-regions.

Expression plasmid pHW697 with the truncated EGI' gene was constructed similarly using a BstEII-BamHI linker (2492/2493) of 69 bp. In this linker we introduced a Pst1-site altering $Val_{421}$ to $Leu_{421}$ and the last 13 amino acids of the coding region: $K_{423}$PKPKPGHGPRSD$_{435}$ were eliminated. The short tail with the rather unusual sequence was cut off to give EGI' a C-terminal corresponding to the one found in *T. reesei* EGI just upstream of the A and B-region.

Figure 4:
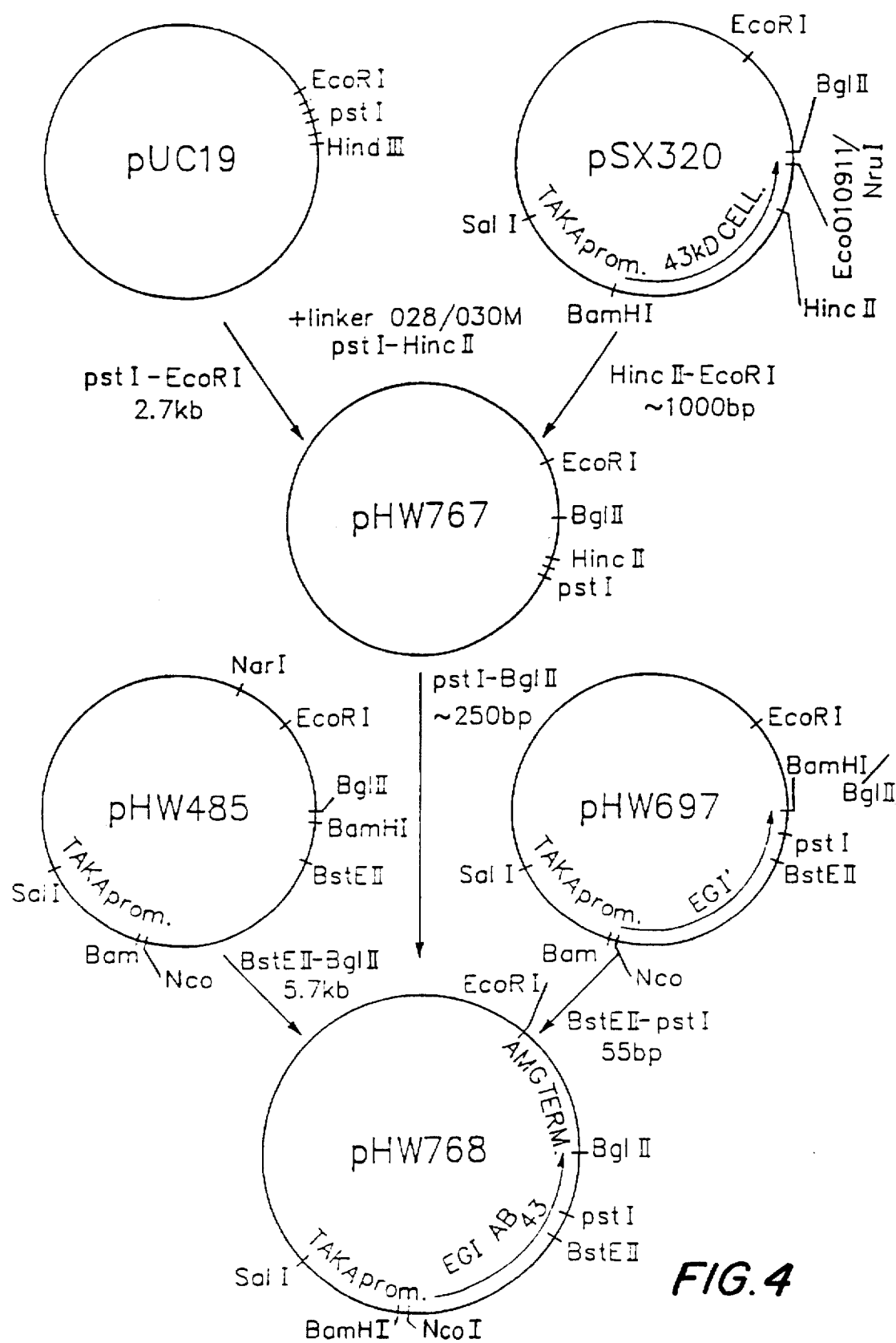
FIG. 4 shows the construction of plasmid pHw768.
Figure 5:
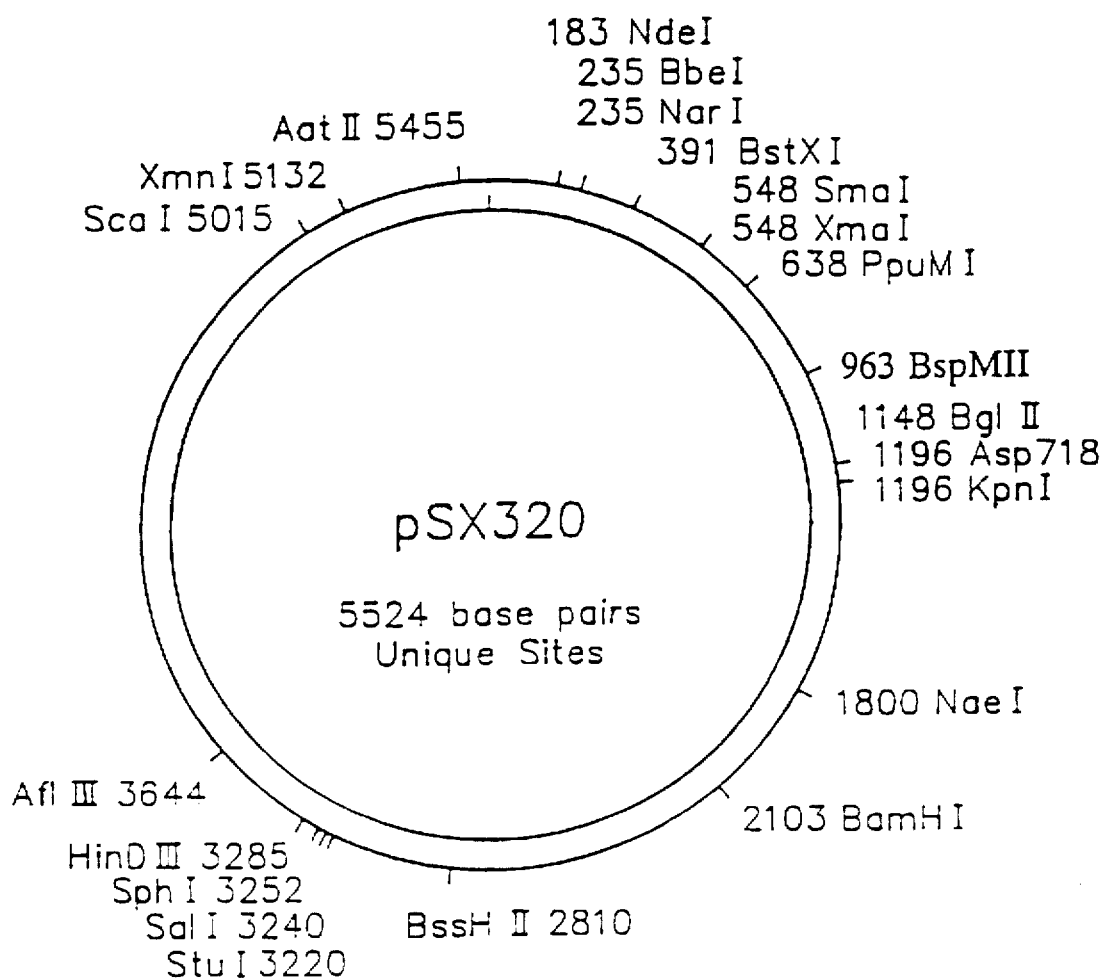
FIG. 5 is a restriction map of plasmid pSX320.

Construction of an Expression Plasmid of EGI' with CBD and B region from a ~43 kD Endoglucanase added C-terminally The ~43 kD endoglucanase of *H. insolens* described in DK patent application No. 736/91 has shown good washing performance. Besides the catalytic domain, 43 kD cellulase has a C-terminal CBD and B region which has been transferred to EGI' which does not have any CBD or B region itself. The construction was done in 2 steps, as outlined in FIG. 4. The PstI-HincII linker (028/030 M) intended to connect the C-terminal of EGI' to the B-region of 43 kD cellulase, was subcloned in pUC19 PstI-EcoRI with C-terminal Hinc2-EcoRI 100 bp fragment from 43 kD cellulase gene in pSX320 (FIG. 5; as described in DK 736/91). From the subclone pHW767 the CBD and B-region was cut out as a 250 bp PstI-BglII fragment and ligated to pHW485 (FIG. 2) BstEII-BglII fragment of 5.7 kb and to the remaining BstEII-PstI fragment of 55 bp from pHW697 (FIG. 3). The resulting expression plasmid pHW768 has the ~43 kD endoglucanase CBD and B region added to $Gln_{422}$ of EGI'.

Figure 6:
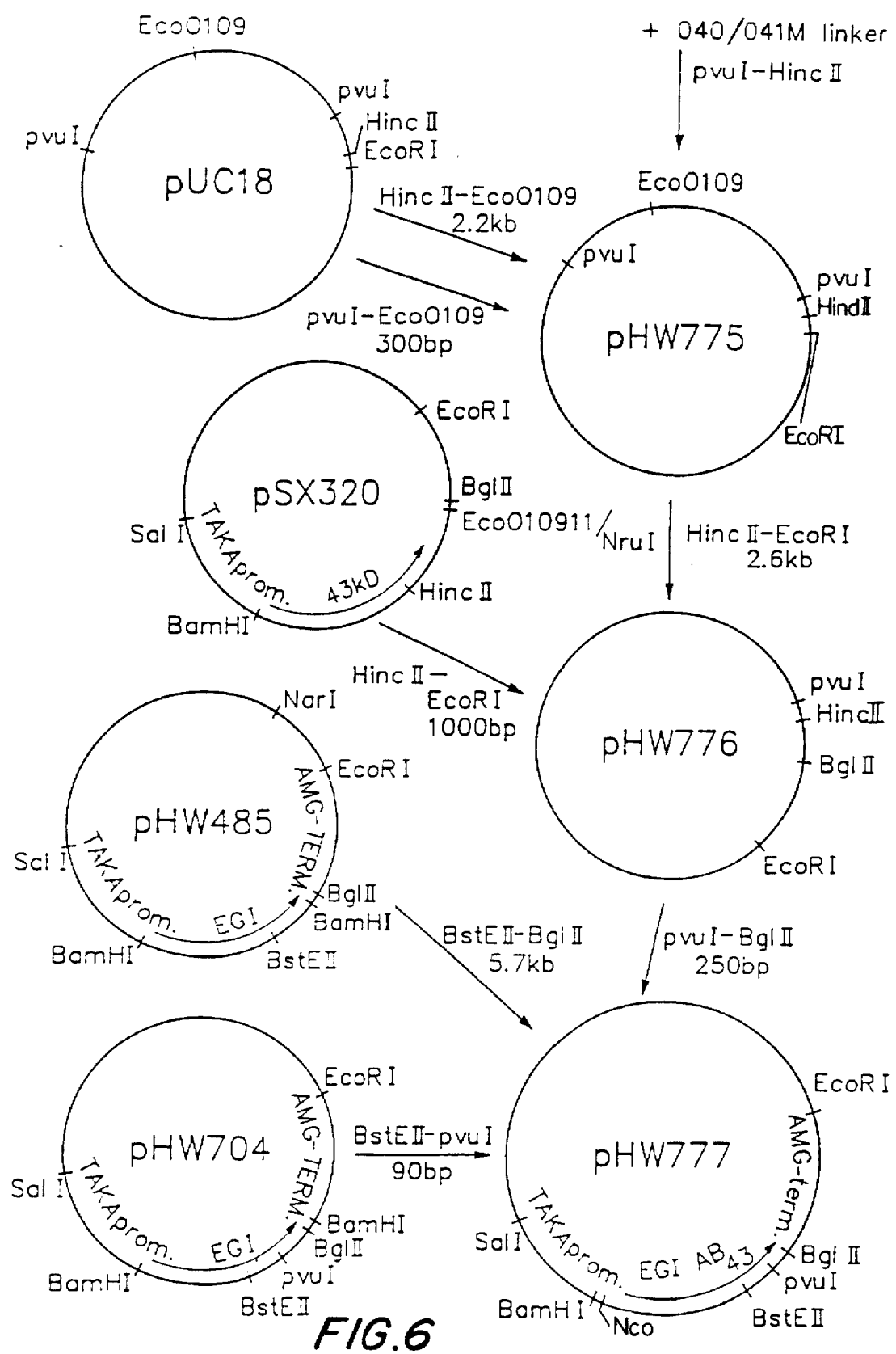
FIG. 6 shows the construction of plasmid pSX777

Construction of an Expression Plasmid of EGI with the CBD and B region from ~43 kD Endoglucanase added C-terminally This plasmid was constructed in a similar way as pHW768 except that, in this case, the C-terminal linker yielded the complete sequence of EGI. FIG. 6 shows the procedure in 3 steps. The PvuI-HincII linker (040 M/041 M) was subcloned in pUC18 to give pHW775, into which a HincII-EcoRI 1000 bp fragment from pSX 320 (FIG. 5) was inserted to give pHW776. From this the CBD and B region was cut out as a 250 bp PvuI-BglII fragment and ligated to 5.7 kb BstEII-BglII fragment from pHW485 (FIG. 2) and 90 bp BstEII-PvuI fragment from pHW704 (FIG. 3). The resulting expression plasmid pHW777 contains the ~43 kD endoglucanase CBD and B region added to $Asp_{435}$ in the complete EGI sequence.

Expression in *A. oryzae* of EGI and EGI' with and without the CBD and B region from ~43 kD endoglucanase The expression plasmids pHW485, pHW704, pHW697, pHW768 and pHW777 were transformed into *A. oryzae* IFO 4177 as described in example 2. Supernatants from transformants grown in YPD medium as described were analyzed by SDS-PAGE, where the native EGI has an apparent Mw of 53 kD. EGI' looks slightly smaller as expected, and the species with the added CBD and B region are increased in molecular weight corresponding to the size of the CBD and B region with some carbohydrate added. A polyclonal antibody AS169 raised against the ~43 kD endoglucanase recognizes EGI and EGI' only when the ~43 kD CBD and B region are added, while all 4 species are recognized by a polyclonal antibody AS78 raised against a cellulase preparation from *H. insolens*. All 4 species have endoglucanase activity as measured on soluble cellulose in the form of carboxy methyl cellulose.

the coding region of the gene. Primers used: NOR 3012 upstream and NOR 3011 downstream.

3) As 2) except that the fragment covered the CBD and B region of A-8 and the Xho I site in the expression vector downstream of gene. Primers: NOR 3017 and NOR 2516.

4) As 2) but with primers NOR 3016 and NOR 3015 covering the CBD and B region from A-9.

5) As 3) but with primers NOR 3021 and NOR 2516 covering the CBD and B region from A-11.

6) As 2) but with primers NOR 3032 and NOR 3022 covering the CBD and B region from A-19.

7) A PCR fragment which includes the CBD from ~43 kD endoglucanase and the Xho I site downstream from the gene Linkers 2492/2493:    BstE2-Pst1-BamH1

5'   GTCACCTACACCAACCTCCGCTGGGGCGAG
3'         GATGTGGTTGGAGGCGACCCCGCTC

ATCGGCTCGACCTACCAGGAGCTGCAGTAGTAA
TAGCCGAGCTGGATGGTCCTCGACGTCATCATT

TGATAG     3'         69 bp (SEQ ID NO:60)
ACTATCCTAG 5'         68 bp (SEQ ID NO:61)

2645/2646:    BstE2-Xma1-PvuI-BamH1

5'   GTCACCTACACCAACCTCCGCTGGGGCGAGATCGGC
3'         GATGTGGTTGGAGGCGACCCCGCTCTAGCCG

TCGACCTACCAGGAGGTTCAGAAGCCTAAGCCCAAG
AGCTGGATGGTCCTCCAAGTCTTCGGATTCGGGTTC

CCCGGGCACGGCCCCCGATCGGACTAATAG        3' 102 bp (SEQ ID NO:62)
GGGCCCGTGCCGGGGGCTAGCCTGATTATCCTAG    5' 101 bp (SEQ ID NO:63)

028 M/030 M:  PstI-HincII

5'   GTCCAGCAGCACCAGCTCTCCGGTC           3' 25 bp (SEQ ID NO:64)
3'   ACGTCAGGTCGTCGTGGTCGAGAGGCCAG       5' 29 bp (SEQ ID NO:65)

040 M/041 M:  PvuI-HincII

5'   CGTCCAGCAGCACCAGCTCTCCGGTC          3' 26 bp (SEQ ID NO:66)
3'   TAGCAGGTCGTCGTGGTCGAGAGGCCAG        5' 28 bp (SEQ ID NO:67)

EXAMPLE 5

~43 kD Endoglucanase with Different CBDs and B-regions:

In order to test the influence on the ~43 kD endoglucanase of the different CBDs and B regions from the A region clones we have substituted the original CBD and B region from ~43 kD with the other C-terminal CBDs and B regions, i.e. A-1, A-8, A-9, A-11, and A-19 (cf. Example 1). In order to test the concept we have also made a construction where the 43 kD B region has been deleted.

Fragments:

All fragments were made by PCR amplification using a Perkin-Elmer/Cetus DNA Amplification System following the manufacturers instructions.

1) A PCR fragment was made which covers the DNA from 56 bp upstream of the Bam HI site on pSX 320 (FIG. 5) to 717 bp within the coding region of the ~43 kD endoglucanase gene and at the same time introduces a Kpn I site at pos. 708 and a Sma I site at pos. 702 in the coding region which is at the very beginning of the B region. This PCR fragment was made with the primers NOR 1542 and NOR 3010 (see list of oligonucleotides below).

2) A PCR fragment was made which includes the CBD and B region of A-1 introducing a Kpn I site at the very beginning of the B region in frame with the Kpn I site introduced in 1) and introducing a Xho I site downstream of on pSX 320 introducing a Pvu II site at the very end of the B region. Primers: NOR3023 and NOR2516.

Combinations:

1)+2) inserted as Bam HI-Kpn I and Kpn I-Xho I into pToC 68 (described in DK736/91) Bam HI-Xho I, thus coding for the 43 kD core enzyme with the CBD and B region from A-1.

1)+3): Like above giving a 43 kD enzyme with the A-8 CBD/B region.

1)+4): As above, but with the A-9 CBD and B region.

1)+5): As above, but with the A-11 CBD and B region.

1)+6): As above, but with the A-19 CBD and B region.

1)+7) inserted as Bam HI-Sma I and Pvu II-Xho I into pToC 68 Bam HI-Xho I, thus coding for the 43 kD enzyme without the B region.

Oligonucleotides:

NOR 1542: 5' - CGACAACATCACATCAAGCTCTCC - 3' (SEQ ID NO:68)

NOR 2516: 5' - CCATCCTTTAACTATAGCGA - 3' (SEQ ID NO:69)

NOR 3010: 5' - GCTGGTGCTGGTACCCGGGATCTGGACGGCAGGG - 3' (SEQ ID NO:70)
              Kpn    Sma

NOR 3011: 5' - GCATCGGTACCGGCGGCGGCTCCACTGGCG - 3' (SEQ ID NO:71)
              Kpn

NOR 3012: 5' - CTCACTCCATCTCGAGTCTTTCAATTTACA - 3' (SEQ ID NO:72)
              Xho

NOR 3015: 5' CTTTTCTCGAGTCCCTTAGTTCAAGCACTGC - 3' (SEQ ID NO:73)
              Xho

NOR 3016: 5' - TGACCGGTACCGGCGGCGGCAACACCAACC - 3' (SEQ ID NO:74)
              Kpn

NOR 3017: 5' - TCACCGGTACCGGCGGTGGAAGCAACAATG - 3' (SEQ ID NO:75)
              Kpn

NOR 3021: 5' - TCTTCGGTACCAGCGGCAACAGCGGCGGCG - 3' (SEQ ID NO:76)
              Kpn

NOR 3022: 5' - CGCTGGGTACCAACAACAATCCTCAGCAGG - 3' (SEQ ID NO:77)
              Kpn

NOR 3023: 5' - CTCCCAGCAGCTGCACTGCTGAGAGGTGGG - 3' (SEQ ID NO:78)
              Pvu II

NOR 3032: 5' - CGGCCTCGAGACCTTACAGGCACTGCGAGT - 3' (SEQ ID NO:79)
              Xho

EXAMPLE 6

Fusion of a Bacterial Catalytic Domain to a Fungal CBD

The endoglucanase Endo 1 produced by Bacillus lautus NCIMB 40250 (described in PCT/DK91/00013) consists of a catalytic domain (core) (Ala(32)-Val(555)) and a C terminal cellulose binding domain (CBD) (Gln556-Pro700) homologous to the CBD of a *B. subtilis* endoglucanase (R. M. MacKay et al. 1986. Nucleic Acids Res. 14, 9159–70). The CBD is proteolytically cleaved off when the enzyme is expressed in *B. subtilis* or *E. coli* generating a CMC degrading core enzyme. In this example this core protein was fused with the B region and CBD of the ~43 kD endoglucanase from *Humicola insolens* (described in DK 736/91). Construction of the fusion.

Figure 7:
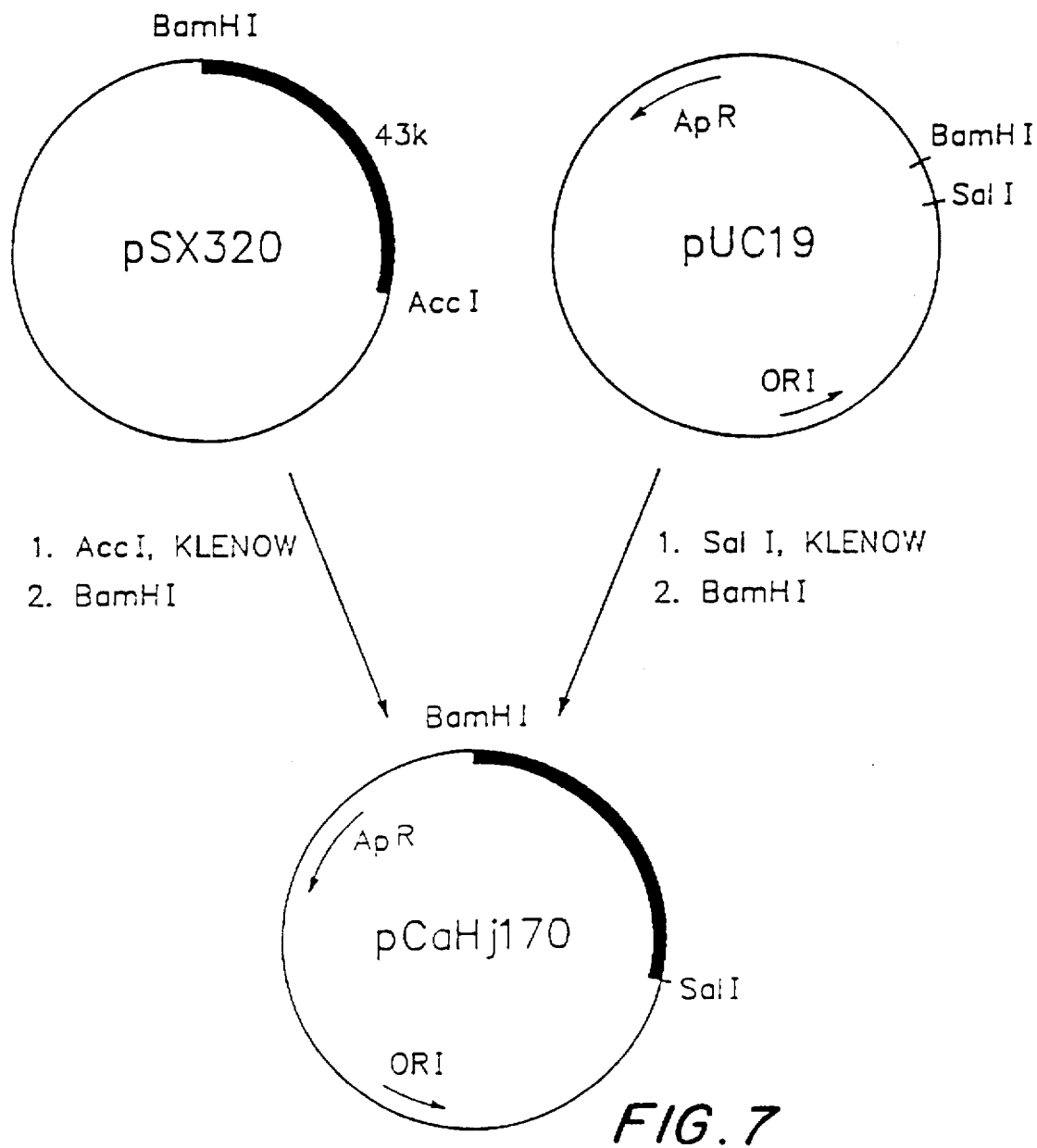
FIG. 7 shows the construction of plasmid pCaHj170.
Figure 8:
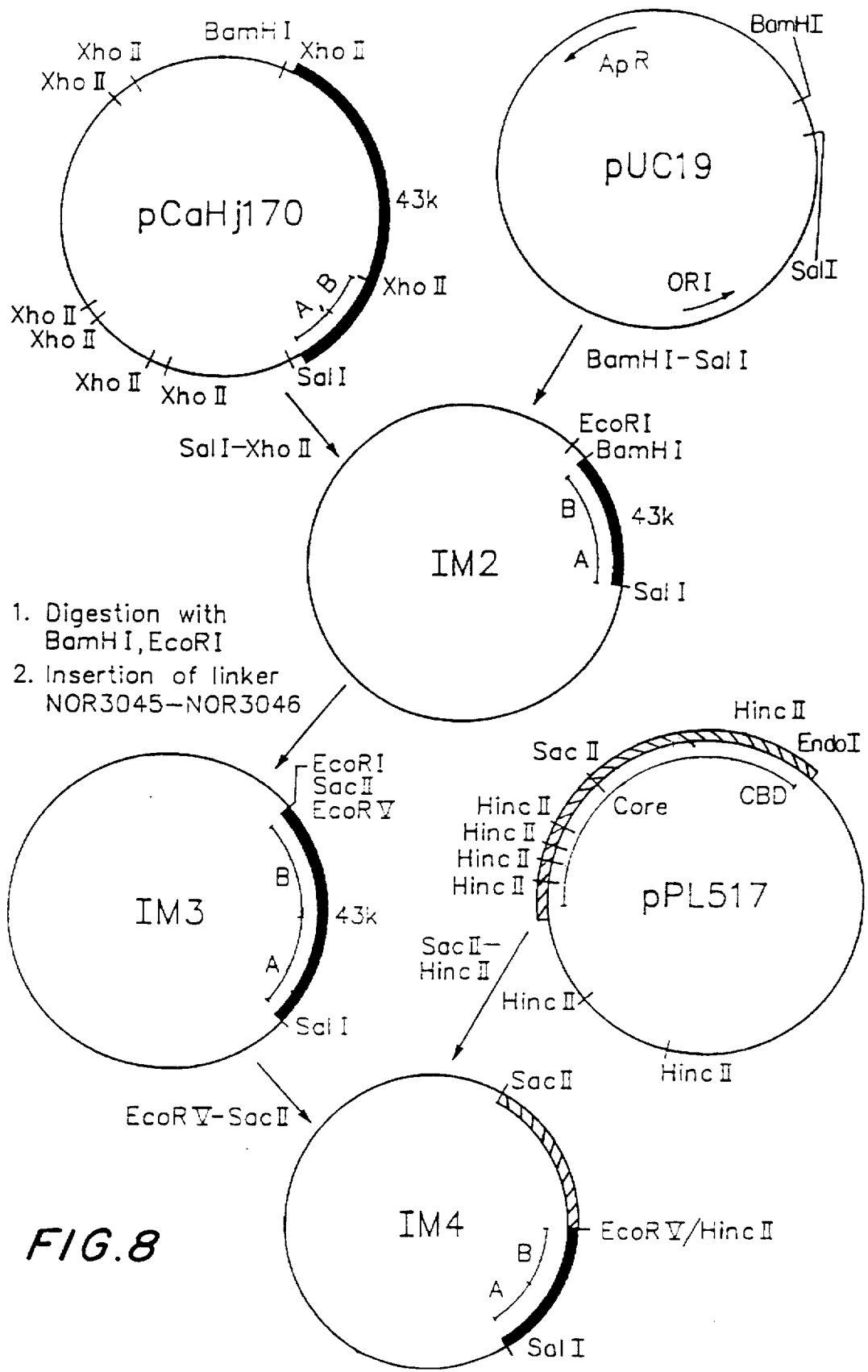
FIG. 8 shows the construction of plasmid IM4.

The plasmid pCaHj 170 containing the cDNA gene encoding the ~43 kD endoglucanase was constructed as shown in FIG. 7. pCaHj 170 was digested with Xho II and Sal I. The 223 bp Xho II-Sal I fragment was isolated and ligated into pUC 19 (Yanisch-Perron et al. 1985. Gene 33, 103–119) digested with BamH I and Sal I. The BamH I site was regenerated by this Xho II-BamH I ligation. The resulting plasmid, IM 2, was digested with Eco R1 and BamH I and ligated with the linker NOR 3045-NOR 3046:

```
NOR 3045  5'  AATTCCGCGGAACGATATCTCCGA       3' (SEQ ID NO:80)
NOR 3046  3'          GGCGCCTTGCTATAGAGGCTCTAG 5' (SEQ ID NO:81)
          EcoR I          EcoR V       Mbo I
             Sac II
```

Figure 9:
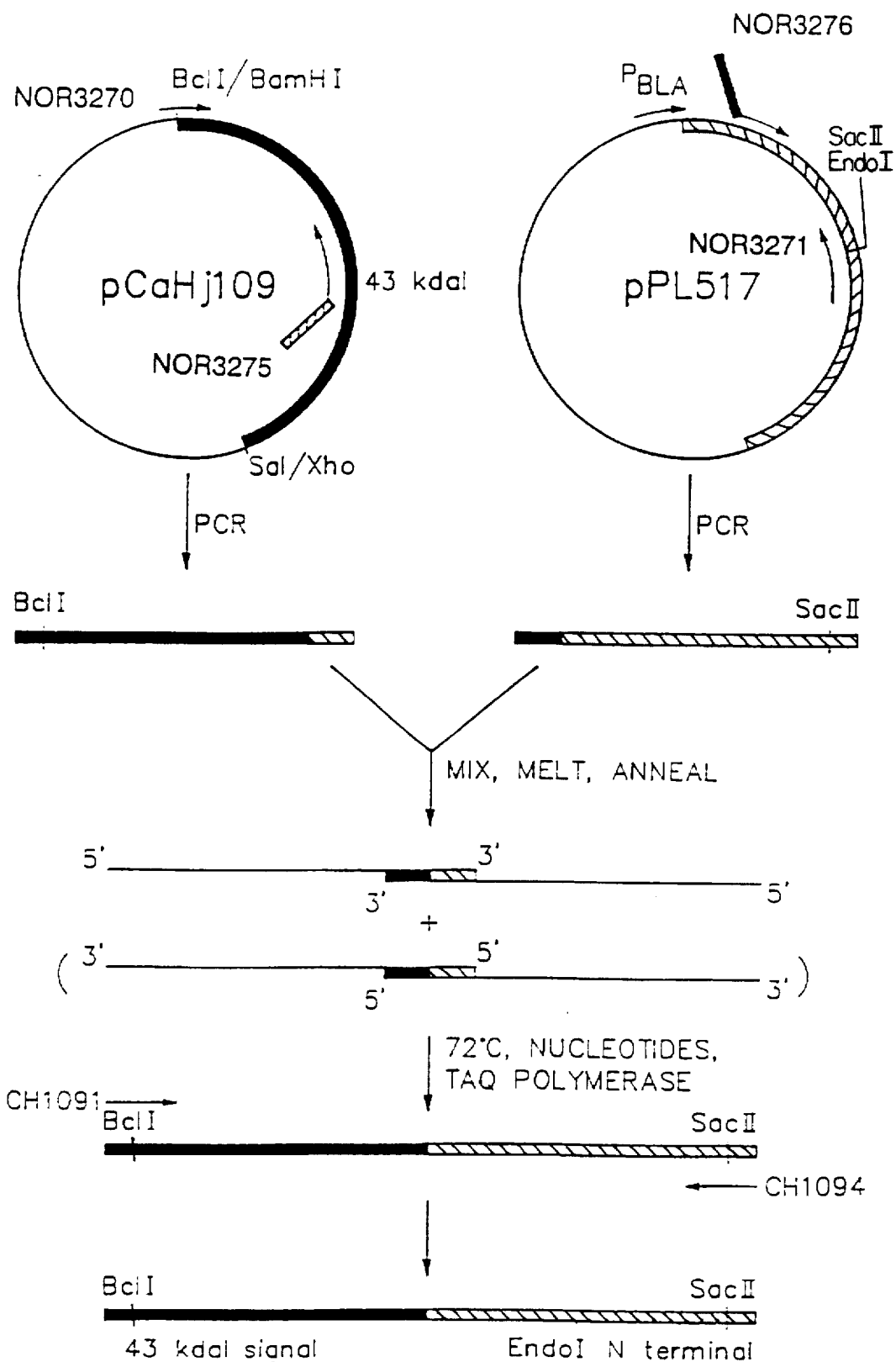
FIG. 9 shows the SOE fusion of the ~43 kD endoglucanase signal peptide and the N-terminal of EndoI.
Figure 10:
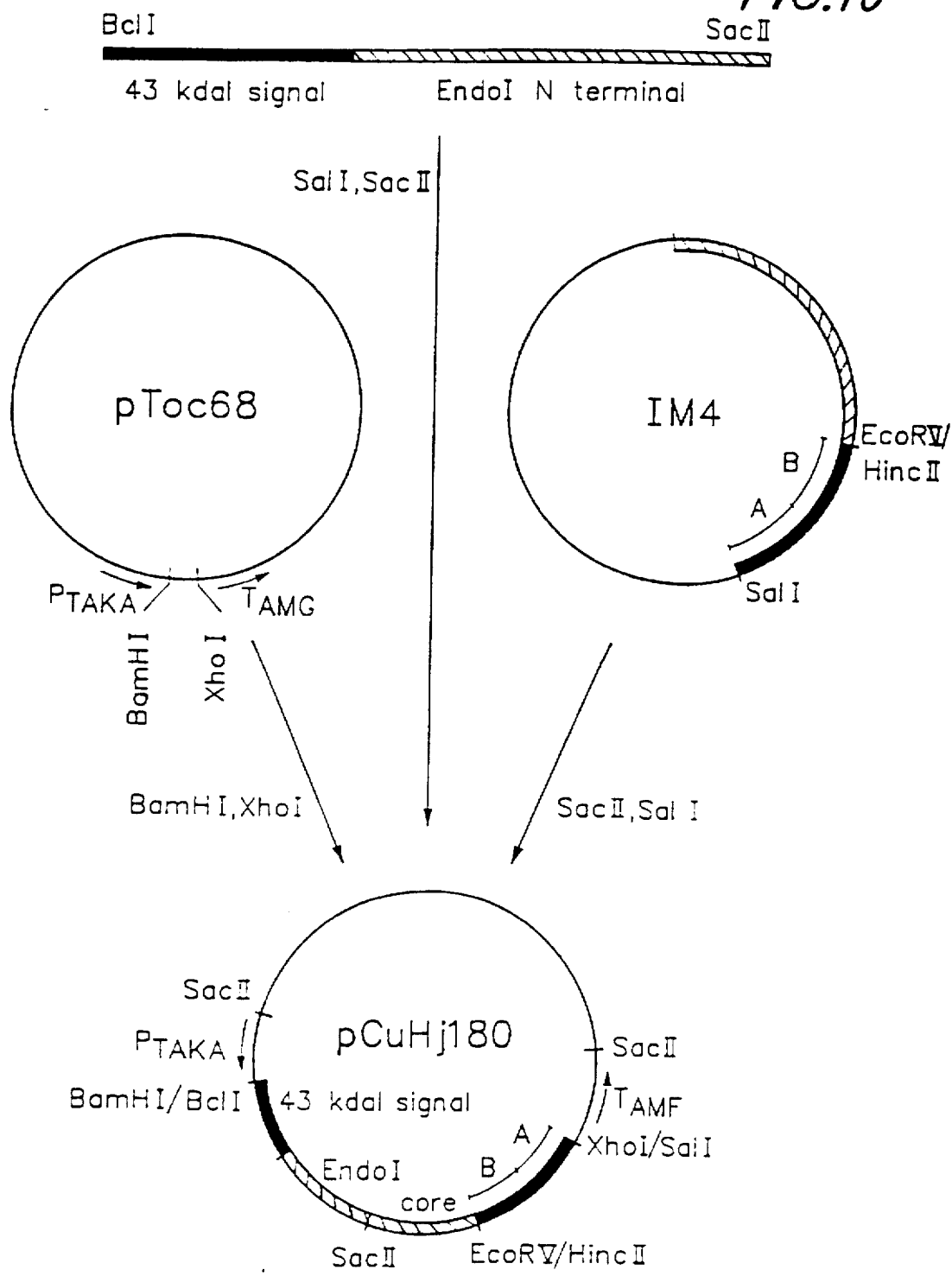
FIG. 10 shows the construction of plasmid pCaHj180.

The resulting plasmid, IM 3, was digested with EcoR V and SacII and ligated to the 445 bp Hinc II-Sac II pPL 517 fragment. pPL 517 contains the entire Bacillus Endo 1 gene (PCT/DK91/00013). The product of this ligation was termed IM 4. In order to replace the Bacillus signal peptide of Endo 1 with the fungal signal peptide from the 43 kdal endoglucanase four PCR primers were designed for "Splicing by Overlap Extension" (SOE) fusion (R. M. Horton et al.(1989) :Gene, 77, 61–68). The 43 kD signal sequence was amplified from the plasmid pCaHj 109 (DK 736/91) introducing a Bcl I site in the 5' end and a 21 bp homology to the Bacillus endo 1 gene in the 3' end using the 5' primer NOR 3270 and the 3' primer NOR 3275. The part of the Endo I gene 5' to the unique Sac II site was amplified using the 5' primer NOR 3276 introducing a 21 bp homology to the 43 kdal gene and the 3' primer NOR 3271 covering the Sac II site. The two PCR fragments were mixed, melted, annealed and filled up with the taq polymerase (FIG. 9). The resulting hybrid was amplified using the primers NOR 3270 and NOR 3271. The hybrid fragment was digested with Bcl 1 and SacII and ligated to the 676 bp Sac II-Sal I fragment from IM 4 and the Aspergillus expression vector pToc 68 (DK 736/91) digested with BamH I. The product of this ligation, pCaHj 180 (FIG. 10), contained an open reading frame encoding the 43 kD signal peptide and the first four N terminal aminoacids of the mature ~43 kD endoglucanase (Met(1)-Arg(25)) fused to the core of Endo 1 (Ser(34)-Val(549)) followed by the peptide Ile-Ser-Glu (encoded by the linker) fused to the 43 kD B region and CBD (Ile(233)-Leu(285)). pCaHj 180 was used to transform Aspergillus oryzae IFO 4177 using selection on acetamide by cotransformation with pToC 90 (cf. DK 736/91) as described in published EP patent application No. 238 023.

NOR 3270  5' TTGAATTCTGATCAAGATGCGTTCCTCCC 3' (SEQ ID NO:82)

NOR 3275  5' AATGGTGAAAGTGACATCACTCCTGCCATCAGCGGCAAGGGC 3' (SEQ ID NO:83)

NOR 3276  5' GCCCTTGCCGCTGATGGCAGGAGTGATGTCACTTTCACCATT 3' (SEQ ID NO:84)

NOR 3271  5' AGCGCGTCCGCGGTAGCTATG 3' (SEQ ID NO:85)

The sequence of the Endo 1 core and the ~43 kD CBD and B region is shown in the appended FIG. 15A–D.

---

We claim:

1. An isolated and purified cellulose- or hemicellulose-degrading enzyme, comprising a catalytically active domain, a carbohydrate binding domain and a linking B region which operably links the catalytically active domain and the carbohydrate binding domain, wherein the carbohydrate binding domain has the following core sequence:

Xaa Xaa Gln Cys Gly Gly Xaa Xaa Xaa Xaa Gly Xaa Xaa Xaa Cys Xaa
1   2   3   4   5   6   7   8   9   10  11  12  13  14  15  16

Xaa Xaa Xaa Xaa Cys Xaa Xaa Xaa Asn Xaa Xaa Tyr Xaa Gln Cys Xaa
17  18  19  20  21  22  23  24  25  26  27  28  29  30  31  32

Xaa
33  (SEQ ID NO:1), wherein:
Xaa in position 1 is Trp or Tyr;
Xaa in position 2 is Gly or Ala ;
Xaa in position 7 is Gln, Ile or Asn;
Xaa in position 8 is Gly or Asn;
Xaa in position 9 is Trp, Phe or Tyr;
Xaa in position 10 is Ser, Asn, Thr or Gln;
Xaa in position 12 is Pro, Ala or Cys;
Xaa in position 13 is Thr, Arg or Lys;
Xaa in position 14 is Thr, Cys or Asn;
Xaa in position 16 is one of the twenty standard L-α-amino acids found in proteins;
Xaa in position 17 is one of the twenty standard L-α-amino acids found in proteins;
Xaa in position 18 is Gly or Pro;
Xaa in position 19 is Ser, Thr, Phe, Leu or Ala, or is absent;
Xaa in position 20 is Thr or Lys;
Xaa in position 22 is Val, Thr, Arg, Glu or Lys;
Xaa in position 23 is Lys, Gln or Ala;
Xaa in position 24 is Gln or Ile;
Xaa in position 26 is Gln, Asp or Ala;
Xaa in position 27 is Trp, Phe or Tyr;
Xaa in position 29 is Tyr, Ser, His or Ala;
Xaa in position 32 is Leu, Ile, Gln, Val or Thr; and
Xaa in position 33 is one of the twenty standard L-α-amino acids found in proteins, or is absent;
wherein the enzyme is endogenous to a strain of a fungus other than Trichoderma or Phanerochaete.

2. The enzyme according to claim 1, which is endogenous to a strain of Humicola.

3. The enzyme according to claim 1, which is endogenous to a strain of Fusarium.

4. The enzyme according to claim 1, which is endogenous to a strain of Myceliopthora.

5. The enzyme according to claim 1, wherein the carbohydrate binding domain has the core sequence:

Trp Gly Gln Cys Gly Gly Gln Gly Trp Asn Gly Pro Thr Cys Cys Glu
Ala Gly Thr Thr Cys Arg Gln Gln Asn Gln Trp Tyr Ser Gln Cys Leu (SEQ ID NO:2).

6. The enzyme according to claim 1, wherein the carbohydrate binding domain has the core sequence:

Trp Gly Gln Cys Gly Gly Ile Gly Trp Asn Gly Pro Thr Thr Cys Val
Ser Gly Ala Thr Cys Thr Lys Ile Asn Asp Trp Tyr His Gln Cys Leu (SEQ ID NO:3).

7. The enzyme according to claim 1, wherein the carbohydrate binding domain has the core sequence:

Trp Gly Gln Cys Gly Gly Ile Gly Phe Asn Gly Pro Thr Cys Cys Gln
Ser Gly Ser Thr Cys Val Lys Gln Asn Asp Trp Tyr Ser Gln Cys Leu (SEQ ID NO:4).

8. The enzyme according to claim 1, wherein the carbohydrate binding domain has the core sequence:

| Trp | Gly | Gln | Cys | Gly | Gly | Asn | Gly | Tyr | Ser | Gly | Pro | Thr | Thr | Cys | Ala |
| Glu | Gly | Thr | Cys | Lys | Lys | Gln | Asn | Asp | Trp | Tyr | Ser | Gln | Cys | Thr | Pro (SEQ ID NO:5). |

9. The enzyme according to claim 1, wherein the carbohydrate binding domain has the core sequence:

| Trp | Gly | Gln | Cys | Gly | Gly | Gln | Gly | Trp | Gln | Gly | Pro | Thr | Cys | Cys | Ser |
| Gln | Gly | Thr | Cys | Arg | Ala | Gln | Asn | Gln | Trp | Tyr | Ser | Gln | Cys | Leu | Asn (SEQ ID NO:6). |

10. The enzyme according to claim 1, wherein the carbohydrate binding domain has the core sequence:

| Trp | Gly | Gln | Cys | Gly | Gly | Gln | Gly | Tyr | Ser | Gly | Cys | Thr | Asn | Cys | Glu |
| Ala | Gly | Ser | Thr | Cys | Arg | Gln | Gln | Asn | Ala | Tyr | Tyr | Ser | Gln | Cys | Ile (SEQ ID NO:7). |

11. The enzyme according to claim 1, wherein the carbohydrate binding domain has the core sequence:

| Trp | Gly | Gln | Cys | Gly | Gly | Gln | Gly | Tyr | Ser | Gly | Cys | Arg | Asn | Cys | Glu |
| Ser | Gly | Ser | Thr | Cys | Arg | Ala | Gln | Asn | Asp | Trp | Tyr | Ser | Gln | Cys | Leu (SEQ ID NO:8). |

12. The enzyme according to claim 1, wherein the carbohydrate binding domain has the core sequence:

| Trp | Ala | Gln | Cys | Gly | Gly | Asn | Gly | Trp | Ser | Gly | Cys | Thr | Thr | Cys | Val |
| Ala | Gly | Ser | Thr | Cys | Thr | Lys | Ile | Asn | Asp | Trp | Tyr | His | Gln | Cys | Leu (SEQ ID NO:9). |

13. The enzyme according to claim 1, wherein the carbohydrate binding domain has the core sequence:

| Trp | Gly | Gln | Cys | Gly | Gly | Gln | Asn | Tyr | Ser | Gly | Pro | Thr | Thr | Cys | Lys |
| Ser | Pro | Phe | Thr | Cys | Lys | Lys | Ile | Asn | Asp | Phe | Tyr | Ser | Gln | Cys | Gln (SEQ ID NO:10). |

14. The enzyme according to claim 1, wherein the carbohydrate binding domain has the core sequence:

| Trp | Gly | Gln | Cys | Gly | Gly | Asn | Gly | Trp | Thr | Gly | Ala | Thr | Thr | Cys | Ala |
| Ser | Gly | Leu | Lys | Cys | Glu | Lys | Ile | Asn | Asp | Trp | Tyr | Tyr | Gln | Cys | Val (SEQ ID NO:11). |

15. The enzyme according to claim 1, wherein the linking B region has an amino acid sequence selected from the group consisting of:

| Ala | Arg | Thr | Asn | Val | Gly | Gly | Gly | Ser | Thr | Gly | Gly | Gly | Asn | Asn | Gly |
| Gly | Gly | Asn | Asn | Gly | Gly | Asn | Pro | Gly | Gly | Asn | Pro | Gly | Gly | Asn | Pro |
| Gly | Gly | Asn | Pro | Gly | Gly | Asn | Pro | Gly | Gly | Asn | Pro | Gly | Gly | Asn | Cys |
| Ser | Pro | Leu (SEQ ID NO:12); | | | | | | | | | | | | | |

| Pro | Gly | Gly | Asn | Asn | Asn | Asn | Pro | Pro | Pro | Ala | Thr | Thr | Ser | Gln | Trp |
| Thr | Pro | Pro | Pro | Ala | Gln | Thr | Ser | Ser | Asn | Pro | Pro | Pro | Thr | Gly | Gly |
| Gly | Gly | Gly | Asn | Thr | Leu | His | Glu | Lys (SEQ ID NO:13); | | | | | | | |

| Gly | Gly | Ser | Asn | Asn | Gly | Gly | Asn | Asn | Asn | Gly | Gly | Gly | Asn | Asn |
| Asn | Gly | Gly | Gly | Asn | Asn | Asn | Gly | Gly | Gly | Asn | Asn | Asn | Gly | Gly |
| Gly | Asn | Thr | Gly | Gly | Gly | Ser | Ala | Pro | Leu (SEQ ID NO:14); | | | | | |

| Val | Phe | Thr | Cys | Ser | Gly | Asn | Ser | Gly | Gly | Gly | Ser | Asn | Pro | Ser | Asn |
| Pro | Asn | Pro | Pro | Thr | Pro | Thr | Thr | Phe | Ile | Thr | Gln | Val | Pro | Asn | Pro |
| Thr | Pro | Val | Ser | Pro | Pro | Thr | Cys | Thr | Val | Ala | Lys (SEQ ID NO:15); | | | |

| Pro | Ala | Leu | Trp | Pro | Asn | Asn | Asn | Pro | Gln | Gln | Gly | Asn | Pro | Asn | Gln |
| Gly | Gly | Asn | Asn | Gly | Gly | Gly | Asn | Gln | Gly | Gly | Gly | Asn | Gly | Gly | Cys |
| Thr | Val | Pro | Lys (SEQ ID NO:16); | | | | | | | | | | | | |

| Pro | Gly | Ser | Gln | Val | Thr | Thr | Ser | Thr | Thr | Ser | Ser | Ser | Ser | Thr | Thr |
| Ser | Arg | Ala | Thr | Ser | Thr | Thr | Ser | Ala | Gly | Gly | Val | Thr | Ser | Ile | Thr |
| Thr | Ser | Pro | Thr | Arg | Thr | Val | Thr | Ile | Pro | Gly | Gly | Ala | Ser | Thr | Thr |
| Ala | Ser | Tyr | Asn (SEQ ID NO:17); | | | | | | | | | | | | |

| Glu | Ser | Gly | Gly | Gly | Asn | Thr | Asn | Pro | Thr | Asn | Pro | Thr | Asn | Pro | Thr |
| Asn | Pro | Thr | Asn | Pro | Thr | Asn | Pro | Trp | Asn | Pro | Gly | Asn | Pro | Thr | Asn |
| Pro | Gly | Asn | Pro | Gly | Gly | Gly | Asn | Gly | Gly | Asn | Gly | Gly | Asn | Cys | Ser |
| Pro | Leu (SEQ ID NO:18); and | | | | | | | | | | | | | | |

| Pro | Ala | Val | Gln | Ile | Pro | Ser | Ser | Ser | Thr | Ser | Ser | Pro | Val | Asn | Gln |
| Pro | Thr | Ser | Thr | Ser | Thr | Thr | Ser | Thr | Ser | Thr | Thr | Ser | Ser | Pro | Pro |
| Val | Gln | Pro | Thr | Thr | Pro | Ser | Gly | Cys | Thr | Ala | Glu | Arg (SEQ ID NO:19). | | |

16. The enzyme according to claim 1 which is a cellulase.

17. The enzyme according to claim 16 which is an endoglucanase, cellobiohydrolase or β-glucosidase.

18. An isolated and purified cellulose- or hemicellulose-degrading enzyme, comprising a catalytically active domain, a carbohydrate binding domain and a linking B region which operably links the catalytically active domain and the carbohydrate binding domain, wherein the linking B region has an amino acid sequence selected from the group consisting of:

| Ala | Arg | Thr | Asn | Val | Gly | Gly | Gly | Ser | Thr | Gly | Gly | Gly | Asn | Asn | Gly |
| Gly | Gly | Asn | Asn | Gly | Gly | Asn | Pro | Gly | Gly | Asn | Pro | Gly | Gly | Asn | Pro |
| Gly | Gly | Asn | Pro | Gly | Gly | Asn | Pro | Gly | Gly | Asn | Pro | Gly | Gly | Asn | Cys |
| Ser | Pro | Leu (SEQ ID NO:12); | | | | | | | | | | | | | |

| Pro | Gly | Gly | Asn | Asn | Asn | Asn | Pro | Pro | Pro | Ala | Thr | Thr | Ser | Gln | Trp |
| Thr | Pro | Pro | Pro | Ala | Gln | Thr | Ser | Ser | Asn | Pro | Pro | Pro | Thr | Gly | Gly |
| Gly | Gly | Gly | Asn | Thr | Leu | His | Glu | Lys (SEQ ID NO:13); | | | | | | | |

| Gly | Gly | Ser | Asn | Asn | Gly | Gly | Asn | Asn | Asn | Gly | Gly | Gly | Asn | Asn |
| Asn | Gly | Gly | Gly | Asn | Asn | Asn | Gly | Gly | Gly | Asn | Asn | Asn | Gly | Gly |
| Gly | Asn | Thr | Gly | Gly | Gly | Ser | Ala | Pro | Leu (SEQ ID NO:14); | | | | | |

| Val | Phe | Thr | Cys | Ser | Gly | Asn | Ser | Gly | Gly | Gly | Ser | Asn | Pro | Ser | Asn |
|---|---|---|---|---|---|---|---|---|---|---|---|---|---|---|---|
| Pro | Asn | Pro | Pro | Thr | Pro | Thr | Thr | Phe | Ile | Thr | Gln | Val | Pro | Asn | Pro |
| Thr | Pro | Val | Ser | Pro | Pro | Thr | Cys | Thr | Val | Ala | Lys (SEQ ID NO:15); | | | | |
| Pro | Ala | Leu | Trp | Pro | Asn | Asn | Asn | Pro | Gln | Gln | Gly | Asn | Pro | Asn | Gln |
| Gly | Gly | Asn | Asn | Gly | Gly | Asn | Gln | Gly | Gly | Gly | Asn | Gly | Gly | Cys | |
| Thr | Val | Pro | Lys (SEQ ID NO:16); | | | | | | | | | | | | |
| Pro | Gly | Ser | Gln | Val | Thr | Thr | Ser | Thr | Thr | Ser | Ser | Ser | Ser | Thr | Thr |
| Ser | Arg | Ala | Thr | Ser | Thr | Thr | Ser | Ala | Gly | Gly | Val | Thr | Ser | Ile | Thr |
| Thr | Ser | Pro | Thr | Arg | Thr | Val | Thr | Ile | Pro | Gly | Gly | Ala | Ser | Thr | Thr |
| Ala | Ser | Tyr | Asn (SEQ ID NO:17); | | | | | | | | | | | | |
| Glu | Ser | Gly | Gly | Gly | Asn | Thr | Asn | Pro | Thr | Asn | Pro | Thr | Asn | Pro | Thr |
| Asn | Pro | Thr | Asn | Pro | Thr | Asn | Pro | Trp | Asn | Pro | Gly | Asn | Pro | Thr | Asn |
| Pro | Gly | Asn | Pro | Gly | Gly | Gly | Asn | Gly | Gly | Asn | Gly | Gly | Asn | Cys | Ser |
| Pro | Leu (SEQ ID NO:18); and | | | | | | | | | | | | | | |
| Pro | Ala | Val | Gln | Ile | Pro | Ser | Ser | Ser | Thr | Ser | Ser | Pro | Val | Asn | Gln |
| Pro | Thr | Ser | Thr | Ser | Thr | Thr | Ser | Thr | Ser | Thr | Thr | Ser | Ser | Pro | Pro |
| Val | Gln | Pro | Thr | Thr | Pro | Ser | Gly | Cys | Thr | Ala | Glu | Arg (SEQ ID NO:19) | | | | wherein the enzyme is endogenous to a strain of a fungus other than Trichoderma or Phanerochaete.

19. The enzyme according to claim 18, which is endogenous to a strain of Humicola.

20. The enzyme according to claim 18, which is endogenous to a strain of Fusarium.

21. The enzyme according to claim 18, which is endogenous to a strain of Myceliopthora.

22. The enzyme according to claim 18, wherein the linking B region has the amino acid sequence:

| Ala | Arg | Thr | Asn | Val | Gly | Gly | Gly | Ser | Thr | Gly | Gly | Gly | Asn | Asn | Gly |
|---|---|---|---|---|---|---|---|---|---|---|---|---|---|---|---|
| Gly | Gly | Asn | Asn | Gly | Gly | Asn | Pro | Gly | Gly | Asn | Pro | Gly | Gly | Asn | Pro |
| Gly | Gly | Asn | Pro | Gly | Gly | Asn | Pro | Gly | Gly | Asn | Pro | Gly | Gly | Asn | Cys |
| Ser | Pro | Leu (SEQ ID NO:12). | | | | | | | | | | | | | |

23. The enzyme according to claim 18, wherein the linking B region has the amino acid sequence:

| Pro | Gly | Gly | Asn | Asn | Asn | Asn | Pro | Pro | Pro | Ala | Thr | Thr | Ser | Gln | Trp |
|---|---|---|---|---|---|---|---|---|---|---|---|---|---|---|---|
| Thr | Pro | Pro | Pro | Ala | Gln | Thr | Ser | Ser | Asn | Pro | Pro | Pro | Thr | Gly | Gly |
| Gly | Gly | Gly | Asn | Thr | Leu | His | Glu | Lys (SEQ ID NO:13). | | | | | | | |

24. The enzyme according to claim 18, wherein the linking B region has the amino acid sequence:

| Gly | Gly | Ser | Asn | Asn | Gly | Gly | Gly | Asn | Asn | Asn | Gly | Gly | Gly | Asn | Asn |
|---|---|---|---|---|---|---|---|---|---|---|---|---|---|---|---|
| Asn | Gly | Gly | Gly | Gly | Asn | Asn | Asn | Gly | Gly | Gly | Asn | Asn | Asn | Gly | Gly |
| Gly | Asn | Thr | Gly | Gly | Gly | Ser | Ala | Pro | Leu (SEQ ID NO:14). | | | | | | |

25. The enzyme according to claim 18, wherein the linking B region has the amino acid sequence:

| Val | Phe | Thr | Cys | Ser | Gly | Asn | Ser | Gly | Gly | Gly | Ser | Asn | Pro | Ser | Asn |
|---|---|---|---|---|---|---|---|---|---|---|---|---|---|---|---|
| Pro | Asn | Pro | Pro | Thr | Pro | Thr | Thr | Phe | Ile | Thr | Gln | Val | Pro | Asn | Pro |
| Thr | Pro | Val | Ser | Pro | Pro | Thr | Cys | Thr | Val | Ala | Lys (SEQ ID NO:15). | | | | |

26. The enzyme according to claim 18, wherein the linking B region has the amino acid sequence:

| | | | | | | | | | | | | | | |
|---|---|---|---|---|---|---|---|---|---|---|---|---|---|---|
| Pro | Ala | Leu | Trp | Pro | Asn | Asn | Asn | Pro | Gln | Gln | Gly | Asn | Pro | Asn | Gln |
| Gly | Gly | Asn | Asn | Gly | Gly | Gly | Asn | Gln | Gly | Gly | Gly | Asn | Gly | Gly | Cys |
| Thr | Val | Pro | Lys (SEQ ID NO:16). | | | | | | | | | | | | |

27. The enzyme according to claim 18, wherein the linking B region has the amino acid sequence:

| | | | | | | | | | | | | | | | |
|---|---|---|---|---|---|---|---|---|---|---|---|---|---|---|---|
| Pro | Gly | Ser | Gln | Val | Thr | Thr | Ser | Thr | Thr | Ser | Ser | Ser | Ser | Thr | Thr |
| Ser | Arg | Ala | Thr | Ser | Thr | Thr | Ser | Ala | Gly | Gly | Val | Thr | Ser | Ile | Thr |
| Thr | Ser | Pro | Thr | Arg | Thr | Val | Thr | Ile | Pro | Gly | Gly | Ala | Ser | Thr | Thr |
| Ala | Ser | Tyr | Asn | (SEQ ID NO:17). | | | | | | | | | | | |

28. The enzyme according to claim 18, wherein the linking B region has the amino acid sequence:

| | | | | | | | | | | | | | | | |
|---|---|---|---|---|---|---|---|---|---|---|---|---|---|---|---|
| Glu | Ser | Gly | Gly | Gly | Asn | Thr | Asn | Pro | Thr | Asn | Pro | Thr | Asn | Pro | Thr |
| Asn | Pro | Thr | Asn | Pro | Thr | Asn | Pro | Trp | Asn | Pro | Gly | Asn | Pro | Thr | Asn |
| Pro | Gly | Asn | Pro | Gly | Gly | Gly | Asn | Gly | Gly | Asn | Gly | Gly | Asn | Cys | Ser |
| Pro | Leu | (SEQ ID NO:18). | | | | | | | | | | | | | |

29. The enzyme according to claim 18, wherein the linking B region has the amino acid sequence:

| | | | | | | | | | | | | | | | |
|---|---|---|---|---|---|---|---|---|---|---|---|---|---|---|---|
| Pro | Ala | Val | Gln | Ile | Pro | Ser | Ser | Ser | Thr | Ser | Ser | Pro | Val | Asn | Gln |
| Pro | Thr | Ser | Thr | Ser | Thr | Thr | Ser | Thr | Ser | Thr | Thr | Ser | Ser | Pro | Pro |
| Val | Gln | Pro | Thr | Thr | Pro | Ser | Gly | Cys | Thr | Ala | Glu | Arg | (SEQ ID NO:19). | | |

\* \* \* \* \*

SEQUENCE LISTING ( 1 ) GENERAL INFORMATION:

( i i i ) NUMBER OF SEQUENCES: 85

( 2 ) INFORMATION FOR SEQ ID NO:1:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( v i ) ORIGINAL SOURCE:
    ( A ) ORGANISM: Synthetic ( x i ) SEQUENCE DESCRIPTION: SEQ ID NO:1:

```
Xaa Xaa Gln Cys Gly Gly Xaa Xaa Xaa Xaa Gly Xaa Xaa Xaa Cys Xaa
1               5                   10                  15

Xaa Xaa Xaa Xaa Cys Xaa Xaa Xaa Asn Xaa Xaa Tyr Xaa Gln Cys Xaa
            20                  25                  30

Xaa
```

( 2 ) INFORMATION FOR SEQ ID NO:2:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Humicola insolens (B) STRAIN: DSM 1800

(x i) SEQUENCE DESCRIPTION: SEQ ID NO:2:

```
Trp Gly Gln Cys Gly Gly Gln Gly Trp Asn Gly Pro Thr Cys Cys Glu
1               5                   10                  15
Ala Gly Thr Thr Cys Arg Gln Gln Asn Gln Trp Tyr Ser Gln Cys Leu
            20                  25                  30
```

(2) INFORMATION FOR SEQ ID NO:3:

(i) SEQUENCE CHARACTERISTICS:
        (A) LENGTH: 32 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i) ORIGINAL SOURCE:
        (A) ORGANISM: Humicola insolens
        (B) STRAIN: DSM 1800

(x i) SEQUENCE DESCRIPTION: SEQ ID NO:3:

```
Trp Gly Gln Cys Gly Gly Ile Gly Trp Asn Gly Pro Thr Thr Cys Val
1               5                   10                  15
Ser Gly Ala Thr Cys Thr Lys Ile Asn Asp Trp Tyr His Gln Cys Leu
            20                  25                  30
```

(2) INFORMATION FOR SEQ ID NO:4:

(i) SEQUENCE CHARACTERISTICS:
        (A) LENGTH: 32 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i) ORIGINAL SOURCE:
        (A) ORGANISM: Humicola insolens
        (B) STRAIN: DSM 1800

(x i) SEQUENCE DESCRIPTION: SEQ ID NO:4:

```
Trp Gly Gln Cys Gly Gly Ile Gly Phe Asn Gly Pro Thr Cys Cys Gln
1               5                   10                  15
Ser Gly Ser Thr Cys Val Lys Gln Asn Asp Trp Tyr Ser Gln Cys Leu
            20                  25                  30
```

(2) INFORMATION FOR SEQ ID NO:5:

(i) SEQUENCE CHARACTERISTICS:
        (A) LENGTH: 32 amino acids
        (B) TYPE: amino acid
        (C) STRANDEDNESS: single
        (D) TOPOLOGY: linear (i i) MOLECULE TYPE: peptide (i i i) HYPOTHETICAL: NO (v i) ORIGINAL SOURCE:
        (A) ORGANISM: Humicola insolens (x i) SEQUENCE DESCRIPTION: SEQ ID NO:5:

```
Trp Gly Gln Cys Gly Gly Asn Gly Tyr Ser Gly Pro Thr Thr Cys Ala
1               5                   10                  15
```

```
Glu  Gly  Thr  Cys  Lys  Lys  Gln  Asn  Asp  Trp  Tyr  Ser  Gln  Cys  Thr  Pro
               20                      25                      30
```

( 2 ) INFORMATION FOR SEQ ID NO:6:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Humicola insolens
    ( B ) STRAIN: DSM 1800

( x i ) SEQUENCE DESCRIPTION: SEQ ID NO:6:

```
Trp  Gly  Gln  Cys  Gly  Gly  Gln  Gly  Trp  Gln  Gly  Pro  Thr  Cys  Cys  Ser
 1                 5                        10                      15

Gln  Gly  Thr  Cys  Arg  Ala  Gln  Asn  Gln  Trp  Tyr  Ser  Gln  Cys  Leu  Asn
               20                      25                      30
```

( 2 ) INFORMATION FOR SEQ ID NO:7:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Humicola insolens
    ( B ) STRAIN: DSM 1800

( x i ) SEQUENCE DESCRIPTION: SEQ ID NO:7:

```
Trp  Gly  Gln  Cys  Gly  Gly  Gln  Gly  Tyr  Ser  Gly  Cys  Thr  Asn  Cys  Glu
 1                 5                        10                      15

Ala  Gly  Ser  Thr  Cys  Arg  Gln  Gln  Asn  Ala  Tyr  Tyr  Ser  Gln  Cys  Ile
               20                      25                      30
```

( 2 ) INFORMATION FOR SEQ ID NO:8:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v i ) ORIGINAL SOURCE:
    ( A ) ORGANISM: Humicola insolens
    ( B ) STRAIN: DSM 1800

( x i ) SEQUENCE DESCRIPTION: SEQ ID NO:8:

```
Trp  Gly  Gln  Cys  Gly  Gly  Gln  Gly  Tyr  Ser  Gly  Cys  Arg  Asn  Cys  Glu
 1                 5                        10                      15

Ser  Gly  Ser  Thr  Cys  Arg  Ala  Gln  Asn  Asp  Trp  Tyr  Ser  Gln  Cys  Leu
               20                      25                      30
```

( 2 ) INFORMATION FOR SEQ ID NO:9:

( i ) SEQUENCE CHARACTERISTICS:
       ( A ) LENGTH: 32 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( v i ) ORIGINAL SOURCE:
       ( A ) ORGANISM: Humicola insolens
       ( B ) STRAIN: DSM 1800

( x i ) SEQUENCE DESCRIPTION: SEQ ID NO:9:

```
Trp Ala Gln Cys Gly Gly Asn Gly Trp Ser Gly Cys Thr Thr Cys Val
1               5                   10                  15
Ala Gly Ser Thr Cys Thr Lys Ile Asn Asp Trp Tyr His Gln Cys Leu
            20              25                      30
```

( 2 ) INFORMATION FOR SEQ ID NO:10:

( i ) SEQUENCE CHARACTERISTICS:
       ( A ) LENGTH: 32 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( v i ) ORIGINAL SOURCE:
       ( A ) ORGANISM: Fusarium oxysporum ( x i ) SEQUENCE DESCRIPTION: SEQ ID NO:10:

```
Trp Gly Gln Cys Gly Gly Gln Asn Tyr Ser Gly Pro Thr Thr Cys Lys
1               5                   10                  15
Ser Pro Phe Thr Cys Lys Lys Ile Asn Asp Phe Tyr Ser Gln Cys Gln
            20              25                      30
```

( 2 ) INFORMATION FOR SEQ ID NO:11:

( i ) SEQUENCE CHARACTERISTICS:
       ( A ) LENGTH: 32 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( v i ) ORIGINAL SOURCE:
       ( A ) ORGANISM: Fusarium oxysporum ( x i ) SEQUENCE DESCRIPTION: SEQ ID NO:11:

```
Trp Gly Gln Cys Gly Gly Asn Gly Trp Thr Gly Ala Thr Thr Cys Ala
1               5                   10                  15
Ser Gly Leu Lys Cys Glu Lys Ile Asn Asp Trp Tyr Tyr Gln Cys Val
            20              25                      30
```

( 2 ) INFORMATION FOR SEQ ID NO:12:

( i ) SEQUENCE CHARACTERISTICS:
       ( A ) LENGTH: 51 amino acids
       ( B ) TYPE: amino acid
       ( C ) STRANDEDNESS: single
       ( D ) TOPOLOGY: linear (  i i  ) MOLECULE TYPE: peptide (  i i i  ) HYPOTHETICAL: NO (  v i  ) ORIGINAL SOURCE:
     ( A ) ORGANISM: Humicola insolens
     ( B ) STRAIN: DSM 1800

(  x i  ) SEQUENCE DESCRIPTION: SEQ ID NO:12:

```
Ala  Arg  Thr  Asn  Val  Gly  Gly  Gly  Ser  Thr  Gly  Gly  Gly  Asn  Asn  Gly
 1                  5                        10                            15

Gly  Gly  Asn  Asn  Gly  Gly  Asn  Pro  Gly  Gly  Asn  Pro  Gly  Gly  Asn  Pro
              20                        25                        30

Gly  Gly  Asn  Pro  Gly  Gly  Asn  Pro  Gly  Gly  Asn  Pro  Gly  Gly  Asn  Cys
              35                        40                        45

Ser  Pro  Leu
      50
```

( 2 ) INFORMATION FOR SEQ ID NO:13:

( i ) SEQUENCE CHARACTERISTICS:
     ( A ) LENGTH: 41 amino acids
     ( B ) TYPE: amino acid
     ( C ) STRANDEDNESS: single
     ( D ) TOPOLOGY: linear (  i i  ) MOLECULE TYPE: peptide (  i i i  ) HYPOTHETICAL: NO (  v i  ) ORIGINAL SOURCE:
     ( A ) ORGANISM: Humicola insolens
     ( B ) STRAIN: DSM 1800

(  x i  ) SEQUENCE DESCRIPTION: SEQ ID NO:13:

```
Pro  Gly  Gly  Asn  Asn  Asn  Asn  Pro  Pro  Pro  Ala  Thr  Thr  Ser  Gln  Trp
 1                  5                        10                            15

Thr  Pro  Pro  Pro  Ala  Gln  Thr  Ser  Ser  Asn  Pro  Pro  Pro  Thr  Gly  Gly
              20                        25                        30

Gly  Gly  Gly  Asn  Thr  Leu  His  Glu  Lys
              35                        40
```

( 2 ) INFORMATION FOR SEQ ID NO:14:

( i ) SEQUENCE CHARACTERISTICS:
     ( A ) LENGTH: 42 amino acids
     ( B ) TYPE: amino acid
     ( C ) STRANDEDNESS: single
     ( D ) TOPOLOGY: linear (  i i  ) MOLECULE TYPE: peptide (  i i i  ) HYPOTHETICAL: NO (  v i  ) ORIGINAL SOURCE:
     ( A ) ORGANISM: Humicola insolens
     ( B ) STRAIN: DSM 1800

(  x i  ) SEQUENCE DESCRIPTION: SEQ ID NO:14:

```
Gly  Gly  Ser  Asn  Asn  Gly  Gly  Gly  Asn  Asn  Asn  Gly  Gly  Gly  Asn  Asn
 1                  5                        10                            15

Asn  Gly  Gly  Gly  Gly  Asn  Asn  Asn  Gly  Gly  Gly  Asn  Asn  Asn  Gly  Gly
              20                        25                        30

Gly  Asn  Thr  Gly  Gly  Gly  Ser  Ala  Pro  Leu
              35                        40
```

( 2 ) INFORMATION FOR SEQ ID NO:15:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:15:

```
Val Phe Thr Cys Ser Gly Asn Ser Gly Gly Gly Ser Asn Pro Ser Asn
 1               5                  10                  15
Pro Asn Pro Pro Thr Pro Thr Thr Phe Ile Thr Gln Val Pro Asn Pro
            20                  25                  30
Thr Pro Val Ser Pro Pro Thr Cys Thr Val Ala Lys
            35                  40
```

( 2 ) INFORMATION FOR SEQ ID NO:16:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:16:

```
Pro Ala Leu Trp Pro Asn Asn Asn Pro Gln Gln Gly Asn Pro Asn Gln
 1               5                  10                  15
Gly Gly Asn Asn Gly Gly Gly Asn Gln Gly Gly Gly Asn Gly Gly Cys
            20                  25                  30
Thr Val Pro Lys
            35
```

( 2 ) INFORMATION FOR SEQ ID NO:17:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:17:

```
Pro Gly Ser Gln Val Thr Thr Ser Thr Thr Ser Ser Ser Ser Thr Thr
 1               5                  10                  15
Ser Arg Ala Thr Ser Thr Thr Ser Ala Gly Gly Val Thr Ser Ile Thr
            20                  25                  30
```

```
            Thr  Ser  Pro  Thr  Arg  Thr  Val  Thr  Ile  Pro  Gly  Gly  Ala  Ser  Thr  Thr
                      35                      40                           45

Ala  Ser  Tyr  Asn
                      50
```

( 2 ) INFORMATION FOR SEQ ID NO:18:

( i ) SEQUENCE CHARACTERISTICS:
        ( A ) LENGTH: 50 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:18:

```
            Glu  Ser  Gly  Gly  Gly  Asn  Thr  Asn  Pro  Thr  Asn  Pro  Thr  Asn  Pro  Thr
            1                   5                        10                          15

Asn  Pro  Thr  Asn  Pro  Thr  Asn  Pro  Trp  Asn  Pro  Gly  Asn  Pro  Thr  Asn
                           20                      25                         30

Pro  Gly  Asn  Pro  Gly  Gly  Gly  Asn  Gly  Gly  Asn  Gly  Gly  Asn  Cys  Ser
                           35                     40                         45

Pro  Leu
                      50
```

( 2 ) INFORMATION FOR SEQ ID NO:19:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Humicola insolens
        ( B ) STRAIN: DSM 1800

( x i ) SEQUENCE DESCRIPTION: SEQ ID NO:19:

```
            Pro  Ala  Val  Gln  Ile  Pro  Ser  Ser  Ser  Thr  Ser  Ser  Pro  Val  Asn  Gln
            1                   5                        10                          15

Pro  Thr  Ser  Thr  Ser  Thr  Thr  Ser  Thr  Ser  Thr  Thr  Ser  Ser  Pro  Pro
                           20                      25                         30

Val  Gln  Pro  Thr  Thr  Pro  Ser  Gly  Cys  Thr  Ala  Glu  Arg
                           35                     40                         45
```

( 2 ) INFORMATION FOR SEQ ID NO:20:

( i ) SEQUENCE CHARACTERISTICS:
        ( A ) LENGTH: 1695 base pairs
        ( B ) TYPE: nucleic acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Fusarium oxysporum -continued ( i x ) FEATURE:
    ( A ) NAME/KEY: CDS
    ( B ) LOCATION: 52..1593

( x i ) SEQUENCE DESCRIPTION: SEQ ID NO:20:

```
AGACCGGAAT TCGCGGCCGC CATCTATCCA ACGGTCTAGC TTCACTTCAC A ATG TAT           57
                                                          Met Tyr
                                                            1

CGC ATC GTC GCA ACC GCC TCG GCT CTT ATT GCC GCT GCT CGG GCT CAA          105
Arg Ile Val Ala Thr Ala Ser Ala Leu Ile Ala Ala Ala Arg Ala Gln
          5                  10                  15

CAG GTC TGC TCT TTG AAC ACC GAG ACC AAG CCT GCC TTG ACC TGG TCC          153
Gln Val Cys Ser Leu Asn Thr Glu Thr Lys Pro Ala Leu Thr Trp Ser
     20                  25                  30

AAG TGT ACA TCC AGC GGC TGC AGC GAT GTC AAG GGC TCC GTT GTT ATT          201
Lys Cys Thr Ser Ser Gly Cys Ser Asp Val Lys Gly Ser Val Val Ile
 35                  40                  45                  50

GAT GCC AAC TGG CGA TGG ACT CAC CAG ACT TCT GGG TCT ACC AAC TGT          249
Asp Ala Asn Trp Arg Trp Thr His Gln Thr Ser Gly Ser Thr Asn Cys
                     55                  60                  65

TAC ACC GGA AAC AAG TGG GAC ACC TCC ATC TGC ACT GAT GGC AAG ACC          297
Tyr Thr Gly Asn Lys Trp Asp Thr Ser Ile Cys Thr Asp Gly Lys Thr
             70                  75                  80

TGC GCC GAA AAG TGC TGT CTT GAT GGC GCC GAC TAT TCT GGT ACC TAC          345
Cys Ala Glu Lys Cys Cys Leu Asp Gly Ala Asp Tyr Ser Gly Thr Tyr
         85                  90                  95

GGA ATC ACC TCC AGC GGC AAC CAG CTC AGT CTT GGA TTC GTC ACC AAC          393
Gly Ile Thr Ser Ser Gly Asn Gln Leu Ser Leu Gly Phe Val Thr Asn
    100                 105                 110

GGT CCC TAC AGC AAG AAC ATC GGC AGC CGA ACC TAC CTC ATG GAG AAC          441
Gly Pro Tyr Ser Lys Asn Ile Gly Ser Arg Thr Tyr Leu Met Glu Asn
115                 120                 125                 130

GAG AAC ACC ATC CAG ATG TTC CAG CTT CTG GGC AAC GAG TTC ACC TTT          489
Glu Asn Thr Ile Gln Met Phe Gln Leu Leu Gly Asn Glu Phe Thr Phe
                    135                 140                 145

GAT GTC GAT GTC TCT GGT ATC GGC TGC GGT CTG AAC GGT GCC CCT CAC          537
Asp Val Asp Val Ser Gly Ile Gly Cys Gly Leu Asn Gly Ala Pro His
                150                 155                 160

TTC GTC AGC ATG GAC GAG GAT GGT GGC AAG GCC AAG TAC TCC GGA AAC          585
Phe Val Ser Met Asp Glu Asp Gly Gly Lys Ala Lys Tyr Ser Gly Asn
            165                 170                 175

AAG GCC GGA GCC AAG TAC GGA ACT GGC TAC TGT GAT GCC CAG TGC CCT          633
Lys Ala Gly Ala Lys Tyr Gly Thr Gly Tyr Cys Asp Ala Gln Cys Pro
        180                 185                 190

CGT GAT GTC AAG TTC ATC AAC GGA GTT GCC AAC TCT GAG GGC TGG AAG          681
Arg Asp Val Lys Phe Ile Asn Gly Val Ala Asn Ser Glu Gly Trp Lys
195                 200                 205                 210

CCC TCT GAC AGT GAT GTC AAC GCT GGT GTT GGT AAT CTG GGC ACC TGC          729
Pro Ser Asp Ser Asp Val Asn Ala Gly Val Gly Asn Leu Gly Thr Cys
                    215                 220                 225

TGC CCC GAG ATG GAT ATC TGG GAG GCC AAC TCC ATC TCC ACC GCC TTC          777
Cys Pro Glu Met Asp Ile Trp Glu Ala Asn Ser Ile Ser Thr Ala Phe
                230                 235                 240

ACT CCT CAT CCT TGC ACC AAG CTC ACA CAG CAC TCT TGC ACT GGC GAC          825
Thr Pro His Pro Cys Thr Lys Leu Thr Gln His Ser Cys Thr Gly Asp
            245                 250                 255

TCT TGT GGT GGA ACC TAC TCT AGT GAC CGA TAT GGC GGT ACT TGC GAT          873
Ser Cys Gly Gly Thr Tyr Ser Ser Asp Arg Tyr Gly Gly Thr Cys Asp
        260                 265                 270

GCC GAC GGT TGT GAT TTC AAT GCC TAC CGT CAG GGC AAC AAG ACC TTC          921
```

-continued

| | | | | | | | | | | | | | | | |
|---|---|---|---|---|---|---|---|---|---|---|---|---|---|---|---|
| Ala | Asp | Gly | Cys | Asp | Phe | Asn | Ala | Tyr | Arg | Gln | Gly | Asn | Lys | Thr | Phe |
| 275 | | | | 280 | | | | | 285 | | | | | 290 | |

| TAC | GGT | CCT | GGA | TCC | AAC | TTC | AAC | ATC | GAC | ACC | ACC | AAG | AAG | ATG | ACT | 969 |
|---|---|---|---|---|---|---|---|---|---|---|---|---|---|---|---|---|
| Tyr | Gly | Pro | Gly | Ser | Asn | Phe | Asn | Ile | Asp | Thr | Thr | Lys | Lys | Met | Thr | |
| | | | | 295 | | | | | 300 | | | | | 305 | | |

| GTT | GTC | ACT | CAG | TTC | CAC | AAG | GGC | AGC | AAC | GGA | CGT | CTT | TCT | GAG | ATC | 1017 |
|---|---|---|---|---|---|---|---|---|---|---|---|---|---|---|---|---|
| Val | Val | Thr | Gln | Phe | His | Lys | Gly | Ser | Asn | Gly | Arg | Leu | Ser | Glu | Ile | |
| | | | 310 | | | | | 315 | | | | | 320 | | | |

| ACC | CGT | CTG | TAC | GTC | CAG | AAC | GGC | AAG | GTC | ATT | GCC | AAC | TCA | GAG | TCC | 1065 |
|---|---|---|---|---|---|---|---|---|---|---|---|---|---|---|---|---|
| Thr | Arg | Leu | Tyr | Val | Gln | Asn | Gly | Lys | Val | Ile | Ala | Asn | Ser | Glu | Ser | |
| | | 325 | | | | | 330 | | | | | 335 | | | | |

| AAG | ATT | GCA | GGC | AAC | CCC | GGT | AGC | TCT | CTC | ACC | TCT | GAC | TTC | TGC | TCC | 1113 |
|---|---|---|---|---|---|---|---|---|---|---|---|---|---|---|---|---|
| Lys | Ile | Ala | Gly | Asn | Pro | Gly | Ser | Ser | Leu | Thr | Ser | Asp | Phe | Cys | Ser | |
| | 340 | | | | | 345 | | | | | 350 | | | | | |

| AAG | CAG | AAG | AGC | GTC | TTT | GGC | GAT | ATC | GAT | GAC | TTC | TCT | AAG | AAG | GGT | 1161 |
|---|---|---|---|---|---|---|---|---|---|---|---|---|---|---|---|---|
| Lys | Gln | Lys | Ser | Val | Phe | Gly | Asp | Ile | Asp | Asp | Phe | Ser | Lys | Lys | Gly | |
| 355 | | | | | 360 | | | | | 365 | | | | | 370 | |

| GGC | TGG | AAC | GGC | ATG | AGC | GAT | GCT | CTC | TCT | GCC | CCT | ATG | GTT | CTT | GTT | 1209 |
|---|---|---|---|---|---|---|---|---|---|---|---|---|---|---|---|---|
| Gly | Trp | Asn | Gly | Met | Ser | Asp | Ala | Leu | Ser | Ala | Pro | Met | Val | Leu | Val | |
| | | | | 375 | | | | | 380 | | | | | 385 | | |

| ATG | TCT | CTC | TGG | CAC | GAC | CAC | CAC | TCC | AAC | ATG | CTC | TGG | CTG | GAC | TCT | 1257 |
|---|---|---|---|---|---|---|---|---|---|---|---|---|---|---|---|---|
| Met | Ser | Leu | Trp | His | Asp | His | His | Ser | Asn | Met | Leu | Trp | Leu | Asp | Ser | |
| | | | 390 | | | | | 395 | | | | | 400 | | | |

| ACC | TAC | CCA | ACC | GAC | TCT | ACC | AAG | GTT | GGA | TCT | CAA | CGA | GGT | TCT | TGC | 1305 |
|---|---|---|---|---|---|---|---|---|---|---|---|---|---|---|---|---|
| Thr | Tyr | Pro | Thr | Asp | Ser | Thr | Lys | Val | Gly | Ser | Gln | Arg | Gly | Ser | Cys | |
| | | 405 | | | | | 410 | | | | | 415 | | | | |

| GCT | ACC | ACC | TCT | GGC | AAG | CCC | TCC | GAC | CTT | GAG | CGA | GAT | GTT | CCC | AAC | 1353 |
|---|---|---|---|---|---|---|---|---|---|---|---|---|---|---|---|---|
| Ala | Thr | Thr | Ser | Gly | Lys | Pro | Ser | Asp | Leu | Glu | Arg | Asp | Val | Pro | Asn | |
| | 420 | | | | | 425 | | | | | 430 | | | | | |

| TCC | AAG | GTT | TCC | TTC | TCC | AAC | ATC | AAG | TTC | GGT | CCC | ATC | GGA | AGC | ACC | 1401 |
|---|---|---|---|---|---|---|---|---|---|---|---|---|---|---|---|---|
| Ser | Lys | Val | Ser | Phe | Ser | Asn | Ile | Lys | Phe | Gly | Pro | Ile | Gly | Ser | Thr | |
| 435 | | | | | 440 | | | | | 445 | | | | | 450 | |

| TAC | AAG | AGC | GAC | GGC | ACC | ACC | CCC | AAC | CCC | CCT | GCC | AGC | AGC | AGC | ACC | 1449 |
|---|---|---|---|---|---|---|---|---|---|---|---|---|---|---|---|---|
| Tyr | Lys | Ser | Asp | Gly | Thr | Thr | Pro | Asn | Pro | Pro | Ala | Ser | Ser | Ser | Thr | |
| | | | | 455 | | | | | 460 | | | | | 465 | | |

| ACT | GGT | TCT | TCC | ACT | CCC | ACC | AAC | CCC | CCT | GCC | GGT | AGC | GTC | GAC | CAA | 1497 |
|---|---|---|---|---|---|---|---|---|---|---|---|---|---|---|---|---|
| Thr | Gly | Ser | Ser | Thr | Pro | Thr | Asn | Pro | Pro | Ala | Gly | Ser | Val | Asp | Gln | |
| | | | 470 | | | | | 475 | | | | | 480 | | | |

| TGG | GGA | CAG | TGC | GGT | GGC | CAG | AAC | TAC | AGC | GGC | CCC | ACG | ACC | TGC | AAG | 1545 |
|---|---|---|---|---|---|---|---|---|---|---|---|---|---|---|---|---|
| Trp | Gly | Gln | Cys | Gly | Gly | Gln | Asn | Tyr | Ser | Gly | Pro | Thr | Thr | Cys | Lys | |
| | | 485 | | | | | 490 | | | | | 495 | | | | |

| TCT | CCT | TTC | ACC | TGC | AAG | AAG | ATC | AAC | GAC | TTC | TAC | TCC | CAG | TGT | CAG | 1593 |
|---|---|---|---|---|---|---|---|---|---|---|---|---|---|---|---|---|
| Ser | Pro | Phe | Thr | Cys | Lys | Lys | Ile | Asn | Asp | Phe | Tyr | Ser | Gln | Cys | Gln | |
| | 500 | | | | | 505 | | | | | 510 | | | | | |

| TAAAGGGGCT | GCCGAGCTAT | CTAGCATGAG | ATTGAGAAAC | GATGTGATGA | GTGGACGATC | 1653 |
|---|---|---|---|---|---|---|
| AAGGAGAAGT | GTGTGGATGA | TATGAACTTG | ATGTGGGAGG | AC | | 1695 |

( 2 ) INFORMATION FOR SEQ ID NO:21:

( i ) SEQUENCE CHARACTERISTICS:
  ( A ) LENGTH: 514 amino acids
  ( B ) TYPE: amino acid
  ( D ) TOPOLOGY: linear ( i i ) MOLECULE TYPE: protein ( x i ) SEQUENCE DESCRIPTION: SEQ ID NO:21:

| Met | Tyr | Arg | Ile | Val | Ala | Thr | Ala | Ser | Ala | Leu | Ile | Ala | Ala | Arg |
|---|---|---|---|---|---|---|---|---|---|---|---|---|---|---|
| 1 | | | | 5 | | | | | 10 | | | | | 15 |

| Ala | Gln | Gln | Val | Cys | Ser | Leu | Asn | Thr | Glu | Thr | Lys | Pro | Ala | Leu | Thr |
|---|---|---|---|---|---|---|---|---|---|---|---|---|---|---|---|
| | | | 20 | | | | | 25 | | | | | 30 | | |

```
Trp Ser Lys Cys Thr Ser Ser Gly Cys Ser Asp Val Lys Gly Ser Val
         35                  40              45

Val Ile Asp Ala Asn Trp Arg Trp Thr His Gln Thr Ser Gly Ser Thr
     50              55              60

Asn Cys Tyr Thr Gly Asn Lys Trp Asp Thr Ser Ile Cys Thr Asp Gly
 65              70              75                           80

Lys Thr Cys Ala Glu Lys Cys Cys Leu Asp Gly Ala Asp Tyr Ser Gly
             85                  90                       95

Thr Tyr Gly Ile Thr Ser Ser Gly Asn Gln Leu Ser Leu Gly Phe Val
             100             105             110

Thr Asn Gly Pro Tyr Ser Lys Asn Ile Gly Ser Arg Thr Tyr Leu Met
         115             120             125

Glu Asn Glu Asn Thr Ile Gln Met Phe Gln Leu Leu Gly Asn Glu Phe
         130             135             140

Thr Phe Asp Val Asp Val Ser Gly Ile Gly Cys Gly Leu Asn Gly Ala
145             150             155                          160

Pro His Phe Val Ser Met Asp Glu Asp Gly Lys Ala Lys Tyr Ser
                 165             170                 175

Gly Asn Lys Ala Gly Ala Lys Tyr Gly Thr Gly Tyr Cys Asp Ala Gln
             180             185                 190

Cys Pro Arg Asp Val Lys Phe Ile Asn Gly Val Ala Asn Ser Glu Gly
         195             200             205

Trp Lys Pro Ser Asp Ser Asp Val Asn Ala Gly Val Gly Asn Leu Gly
     210             215             220

Thr Cys Cys Pro Glu Met Asp Ile Trp Glu Ala Asn Ser Ile Ser Thr
225             230             235                          240

Ala Phe Thr Pro His Pro Cys Thr Lys Leu Thr Gln His Ser Cys Thr
                 245             250             255

Gly Asp Ser Cys Gly Gly Thr Tyr Ser Ser Asp Arg Tyr Gly Gly Thr
             260             265             270

Cys Asp Ala Asp Gly Cys Asp Phe Asn Ala Tyr Arg Gln Gly Asn Lys
         275             280             285

Thr Phe Tyr Gly Pro Gly Ser Asn Phe Asn Ile Asp Thr Thr Lys Lys
     290             295             300

Met Thr Val Val Thr Gln Phe His Lys Gly Ser Asn Gly Arg Leu Ser
305             310             315                          320

Glu Ile Thr Arg Leu Tyr Val Gln Asn Gly Lys Val Ile Ala Asn Ser
             325             330             335

Glu Ser Lys Ile Ala Gly Asn Pro Gly Ser Ser Leu Thr Ser Asp Phe
         340             345             350

Cys Ser Lys Gln Lys Ser Val Phe Gly Asp Ile Asp Asp Phe Ser Lys
         355             360             365

Lys Gly Gly Trp Asn Gly Met Ser Asp Ala Leu Ser Ala Pro Met Val
     370             375             380

Leu Val Met Ser Leu Trp His Asp His His Ser Asn Met Leu Trp Leu
385             390             395                          400

Asp Ser Thr Tyr Pro Thr Asp Ser Thr Lys Val Gly Ser Gln Arg Gly
                 405             410             415

Ser Cys Ala Thr Thr Ser Gly Lys Pro Ser Asp Leu Glu Arg Asp Val
             420             425             430

Pro Asn Ser Lys Val Ser Phe Ser Asn Ile Lys Phe Gly Pro Ile Gly
         435             440             445

Ser Thr Tyr Lys Ser Asp Gly Thr Thr Pro Asn Pro Pro Ala Ser Ser
```

```
                    450                       455                       460
        Ser  Thr  Thr  Gly  Ser  Ser  Thr  Pro  Thr  Asn  Pro  Pro  Ala  Gly  Ser  Val
        465                      470                      475                      480

Asp  Gln  Trp  Gly  Gln  Cys  Gly  Gly  Gln  Asn  Tyr  Ser  Gly  Pro  Thr  Thr
                                 485                      490                      495

Cys  Lys  Ser  Pro  Phe  Thr  Cys  Lys  Lys  Ile  Asn  Asp  Phe  Tyr  Ser  Gln
                            500                      505                      510

Cys  Gln
```

( 2 ) INFORMATION FOR SEQ ID NO:22:

( i ) SEQUENCE CHARACTERISTICS:
        ( A ) LENGTH: 1282 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Fusarium oxysporum ( i x ) FEATURE:
        ( A ) NAME/KEY: CDS
        ( B ) LOCATION: 51..1205

( x i ) SEQUENCE DESCRIPTION: SEQ ID NO:22:

```
GAATTCGCGG  CCGCCTGCTT  CGAAGCATCA  GCTCATTGAG  ATCAGTCAAA  ATG CAT        56
                                                            Met His
                                                             1

ACC CTT TCG GTT CTC CTC GCT CTC GCT CCC GTG TCC GCC CTT GCT CAG           104
Thr Leu Ser Val Leu Leu Ala Leu Ala Pro Val Ser Ala Leu Ala Gln
         5                  10                  15

GCT CCC ATC TGG GGA CAG TGC GGT GGC AAT GGT TGG ACC GGT GCT ACA           152
Ala Pro Ile Trp Gly Gln Cys Gly Gly Asn Gly Trp Thr Gly Ala Thr
         20                  25                  30

ACC TGC GCT AGT GGT CTG AAG TGT GAG AAG ATC AAC GAC TGG TAC TAT           200
Thr Cys Ala Ser Gly Leu Lys Cys Glu Lys Ile Asn Asp Trp Tyr Tyr
 35                  40                  45                  50

CAG TGT GTT CCT GGA TCT GGA GGA TCT GAA CCC CAG CCT TCG TCA ACT           248
Gln Cys Val Pro Gly Ser Gly Gly Ser Glu Pro Gln Pro Ser Ser Thr
                 55                  60                  65

CAG GGT GGT GGC ACT CCT CAG CCT ACT GGC GGT AAC AGC GGC GGC ACT           296
Gln Gly Gly Gly Thr Pro Gln Pro Thr Gly Gly Asn Ser Gly Gly Thr
             70                  75                  80

GGT CTC GAC GCC AAA TTC AAG GCC AAG GGC AAG CAG TAC TTT GGT ACC           344
Gly Leu Asp Ala Lys Phe Lys Ala Lys Gly Lys Gln Tyr Phe Gly Thr
         85                  90                  95

GAG ATT GAC CAC TAC CAC CTT AAC AAC AAT CCT CTG ATC AAC ATT GTC           392
Glu Ile Asp His Tyr His Leu Asn Asn Asn Pro Leu Ile Asn Ile Val
     100                 105                 110

AAG GCC CAG TTT GGC CAA GTG ACA TGC GAG AAC AGC ATG AAG TGG GAT           440
Lys Ala Gln Phe Gly Gln Val Thr Cys Glu Asn Ser Met Lys Trp Asp
115                 120                 125                 130

GCC ATT GAG CCT TCA CGC AAC TCC TTC ACC TTC AGT AAC GCT GAC AAG           488
Ala Ile Glu Pro Ser Arg Asn Ser Phe Thr Phe Ser Asn Ala Asp Lys
                 135                 140                 145

GTC GTC GAC TTC GCC ACT CAG AAC GGC AAG CTC ATC CGT GGC CAC ACT           536
Val Val Asp Phe Ala Thr Gln Asn Gly Lys Leu Ile Arg Gly His Thr
             150                 155                 160

CTT CTC TGG CAC TCT CAG CTG CCT CAG TGG GTT CAG AAC ATC AAC GAT           584
```

| | | | | | | | | | | | | | | | | |
|---|---|---|---|---|---|---|---|---|---|---|---|---|---|---|---|---|
|Leu|Leu|Trp|His|Ser|Gln|Leu|Pro|Gln|Trp|Val|Gln|Asn|Ile|Asn|Asp| |
| | |165| | | | |170| | | |175| | | | | |

| | | | | | | | | | | | | | | | | |
|---|---|---|---|---|---|---|---|---|---|---|---|---|---|---|---|---|
|CGC|TCT|ACC|CTC|ACC|GCG|GTC|ATC|GAG|AAC|CAC|GTC|AAG|ACC|ATG|GTC|632|
|Arg|Ser|Thr|Leu|Thr|Ala|Val|Ile|Glu|Asn|His|Val|Lys|Thr|Met|Val| |
| |180| | | | |185| | | | |190| | | | | |

| | | | | | | | | | | | | | | | | |
|---|---|---|---|---|---|---|---|---|---|---|---|---|---|---|---|---|
|ACC|CGC|TAC|AAG|GGC|AAG|ATC|CTC|CAG|TGG|GAC|GTT|GTC|AAC|AAC|GAG|680|
|Thr|Arg|Tyr|Lys|Gly|Lys|Ile|Leu|Gln|Trp|Asp|Val|Val|Asn|Asn|Glu| |
|195| | | | |200| | | | |205| | | | |210| |

| | | | | | | | | | | | | | | | | |
|---|---|---|---|---|---|---|---|---|---|---|---|---|---|---|---|---|
|ATC|TTC|GCT|GAG|GAC|GGT|AAC|CTC|CGC|GAC|AGT|GTC|TTC|AGC|CGA|GTT|728|
|Ile|Phe|Ala|Glu|Asp|Gly|Asn|Leu|Arg|Asp|Ser|Val|Phe|Ser|Arg|Val| |
| | | | |215| | | | |220| | | | |225| | |

| | | | | | | | | | | | | | | | | |
|---|---|---|---|---|---|---|---|---|---|---|---|---|---|---|---|---|
|CTC|GGT|GAG|GAC|TTT|GTC|GGT|ATT|GCT|TTC|CGC|GCT|GCC|CGC|GCC|GCT|776|
|Leu|Gly|Glu|Asp|Phe|Val|Gly|Ile|Ala|Phe|Arg|Ala|Ala|Arg|Ala|Ala| |
| | | |230| | | | |235| | | | |240| | | |

| | | | | | | | | | | | | | | | | |
|---|---|---|---|---|---|---|---|---|---|---|---|---|---|---|---|---|
|GAT|CCC|GCT|GCC|AAG|CTC|TAC|ATC|AAC|GAT|TAT|AAC|CTC|GAC|AAG|TCC|824|
|Asp|Pro|Ala|Ala|Lys|Leu|Tyr|Ile|Asn|Asp|Tyr|Asn|Leu|Asp|Lys|Ser| |
| | |245| | | | |250| | | | |255| | | | |

| | | | | | | | | | | | | | | | | |
|---|---|---|---|---|---|---|---|---|---|---|---|---|---|---|---|---|
|GAC|TAT|GCT|AAG|GTC|ACC|CGC|GGA|ATG|GTC|GCT|CAC|GTT|AAT|AAG|TGG|872|
|Asp|Tyr|Ala|Lys|Val|Thr|Arg|Gly|Met|Val|Ala|His|Val|Asn|Lys|Trp| |
| |260| | | | |265| | | | |270| | | | | |

| | | | | | | | | | | | | | | | | |
|---|---|---|---|---|---|---|---|---|---|---|---|---|---|---|---|---|
|ATT|GCT|GCT|GGT|ATT|CCC|ATC|GAC|GGT|ATT|GGA|TCT|CAG|GGC|CAT|CTT|920|
|Ile|Ala|Ala|Gly|Ile|Pro|Ile|Asp|Gly|Ile|Gly|Ser|Gln|Gly|His|Leu| |
|275| | | | |280| | | | |285| | | | |290| |

| | | | | | | | | | | | | | | | | |
|---|---|---|---|---|---|---|---|---|---|---|---|---|---|---|---|---|
|GCT|GCT|CCT|AGT|GGC|TGG|AAC|CCT|GCC|TCT|GGT|GTT|CCT|GCT|GCT|CTC|968|
|Ala|Ala|Pro|Ser|Gly|Trp|Asn|Pro|Ala|Ser|Gly|Val|Pro|Ala|Ala|Leu| |
| | | | |295| | | | |300| | | | |305| | |

| | | | | | | | | | | | | | | | | |
|---|---|---|---|---|---|---|---|---|---|---|---|---|---|---|---|---|
|CGA|GCT|CTT|GCC|GCC|TCG|GAC|GCC|AAG|GAG|ATT|GCT|ATC|ACT|GAG|CTT|1016|
|Arg|Ala|Leu|Ala|Ala|Ser|Asp|Ala|Lys|Glu|Ile|Ala|Ile|Thr|Glu|Leu| |
| | | |310| | | | |315| | | | |320| | | |

| | | | | | | | | | | | | | | | | |
|---|---|---|---|---|---|---|---|---|---|---|---|---|---|---|---|---|
|GAT|ATT|GCC|GGT|GCC|AGT|GCT|AAC|GAT|TAC|CTT|ACT|GTC|ATG|AAC|GCT|1064|
|Asp|Ile|Ala|Gly|Ala|Ser|Ala|Asn|Asp|Tyr|Leu|Thr|Val|Met|Asn|Ala| |
| | |325| | | | |330| | | | |335| | | | |

| | | | | | | | | | | | | | | | | |
|---|---|---|---|---|---|---|---|---|---|---|---|---|---|---|---|---|
|TGC|CTT|GCC|GTT|CCC|AAG|TGT|GTC|GGC|ATC|ACT|GTC|TGG|GGT|GTC|TCT|1112|
|Cys|Leu|Ala|Val|Pro|Lys|Cys|Val|Gly|Ile|Thr|Val|Trp|Gly|Val|Ser| |
| |340| | | | |345| | | | |350| | | | | |

| | | | | | | | | | | | | | | | | |
|---|---|---|---|---|---|---|---|---|---|---|---|---|---|---|---|---|
|GAC|AAG|GAC|TCG|TGG|CGA|CCT|GGT|GAC|AAC|CCC|CTC|CTC|TAC|GAC|AGC|1160|
|Asp|Lys|Asp|Ser|Trp|Arg|Pro|Gly|Asp|Asn|Pro|Leu|Leu|Tyr|Asp|Ser| |
|355| | | | |360| | | | |365| | | | |370| |

| | | | | | | | | | | | | | | | |
|---|---|---|---|---|---|---|---|---|---|---|---|---|---|---|---|
|AAC|TAC|CAG|CCC|AAG|GCT|GCT|TTC|AAT|GCC|TTG|GCT|AAC|GCT|CTG|1205|
|Asn|Tyr|Gln|Pro|Lys|Ala|Ala|Phe|Asn|Ala|Leu|Ala|Asn|Ala|Leu| |
| | | |375| | | | |380| | | | |385| | |

| | | | | | |
|---|---|---|---|---|---|
|TGAGCTGTTG|TTGATGTATG|TCGCTGGATC|ATACAACGAA|ACGTCCTAGT|TGGATAAAGC|1265|
|GTTGATGGTA|GAATGAT| | | | |1282|

( 2 ) INFORMATION FOR SEQ ID NO:23:

( i ) SEQUENCE CHARACTERISTICS:
        ( A ) LENGTH: 385 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | | |
|---|---|---|---|---|---|---|---|---|---|---|---|---|---|---|---|
|Met|His|Thr|Leu|Ser|Val|Leu|Leu|Ala|Leu|Ala|Pro|Val|Ser|Ala|Leu|
|1| | | |5| | | | |10| | | | |15| |

| | | | | | | | | | | | | | | |
|---|---|---|---|---|---|---|---|---|---|---|---|---|---|---|
|Ala|Gln|Ala|Pro|Ile|Trp|Gly|Gln|Cys|Gly|Gly|Asn|Gly|Trp|Thr|Gly|
| | | |20| | | | |25| | | | |30| |

| | | | | | | | | | | | | | | |
|---|---|---|---|---|---|---|---|---|---|---|---|---|---|---|
|Ala|Thr|Thr|Cys|Ala|Ser|Gly|Leu|Lys|Cys|Glu|Lys|Ile|Asn|Asp|Trp|
| | |35| | | | |40| | | | |45| | |

```
Tyr Tyr Gln Cys Val Pro Gly Ser Gly Gly Ser Glu Pro Gln Pro Ser
        50              55              60

Ser Thr Gln Gly Gly Thr Pro Gln Pro Thr Gly Gly Asn Ser Gly
65              70              75                          80

Gly Thr Gly Leu Asp Ala Lys Phe Lys Ala Lys Gly Lys Gln Tyr Phe
                85              90              95

Gly Thr Glu Ile Asp His Tyr His Leu Asn Asn Asn Pro Leu Ile Asn
            100             105             110

Ile Val Lys Ala Gln Phe Gly Gln Val Thr Cys Glu Asn Ser Met Lys
        115             120             125

Trp Asp Ala Ile Glu Pro Ser Arg Asn Ser Phe Thr Phe Ser Asn Ala
130             135             140

Asp Lys Val Val Asp Phe Ala Thr Gln Asn Gly Lys Leu Ile Arg Gly
145             150             155             160

His Thr Leu Leu Trp His Ser Gln Leu Pro Gln Trp Val Gln Asn Ile
                165             170             175

Asn Asp Arg Ser Thr Leu Thr Ala Val Ile Glu Asn His Val Lys Thr
            180             185             190

Met Val Thr Arg Tyr Lys Gly Lys Ile Leu Gln Trp Asp Val Val Asn
        195             200             205

Asn Glu Ile Phe Ala Glu Asp Gly Asn Leu Arg Asp Ser Val Phe Ser
210             215             220

Arg Val Leu Gly Glu Asp Phe Val Gly Ile Ala Phe Arg Ala Ala Arg
225             230             235             240

Ala Ala Asp Pro Ala Ala Lys Leu Tyr Ile Asn Asp Tyr Asn Leu Asp
                245             250             255

Lys Ser Asp Tyr Ala Lys Val Thr Arg Gly Met Val Ala His Val Asn
            260             265             270

Lys Trp Ile Ala Ala Gly Ile Pro Ile Asp Gly Ile Gly Ser Gln Gly
        275             280             285

His Leu Ala Ala Pro Ser Gly Trp Asn Pro Ala Ser Gly Val Pro Ala
290             295             300

Ala Leu Arg Ala Leu Ala Ala Ser Asp Ala Lys Glu Ile Ala Ile Thr
305             310             315             320

Glu Leu Asp Ile Ala Gly Ala Ser Ala Asn Asp Tyr Leu Thr Val Met
                325             330             335

Asn Ala Cys Leu Ala Val Pro Lys Cys Val Gly Ile Thr Val Trp Gly
            340             345             350

Val Ser Asp Lys Asp Ser Trp Arg Pro Gly Asp Asn Pro Leu Leu Tyr
        355             360             365

Asp Ser Asn Tyr Gln Pro Lys Ala Ala Phe Asn Ala Leu Ala Asn Ala
370             375             380

Leu
385
```

( 2 ) INFORMATION FOR SEQ ID NO:24:

( i ) SEQUENCE CHARACTERISTICS:
        ( A ) LENGTH: 1584 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (vi) ORIGINAL SOURCE:
    (A) ORGANISM: Fusarium oxysporum (ix) FEATURE:
    (A) NAME/KEY: CDS
    (B) LOCATION: 55..1335

(xi) SEQUENCE DESCRIPTION: SEQ ID NO:24:

```
GAATTCGCGG CCGCCTAGAT AAGTCACTAC CTGATCTCTG AATAATCTTT CATC ATG              57
                                                              Met
                                                                1

AAG TCT CTC TCA CTC ATC CTC TCA GCC CTG GCT GTC CAG GTC GCT GTT             105
Lys Ser Leu Ser Leu Ile Leu Ser Ala Leu Ala Val Gln Val Ala Val
              5                  10                  15

GCT CAA ACC CCC GAC AAG GCC AAG GAG CAG CAC CCC AAG CTC GAG ACC             153
Ala Gln Thr Pro Asp Lys Ala Lys Glu Gln His Pro Lys Leu Glu Thr
         20                  25                  30

TAC CGC TGC ACC AAG GCC TCT GGC TGC AAG AAG CAA ACC AAC TAC ATC             201
Tyr Arg Cys Thr Lys Ala Ser Gly Cys Lys Lys Gln Thr Asn Tyr Ile
     35                  40                  45

GTC GCC GAC GCA GGT ATT CAC GGC ATT CGC AGA AGC GCC GGC TGC GGT             249
Val Ala Asp Ala Gly Ile His Gly Ile Arg Arg Ser Ala Gly Cys Gly
 50                  55                  60                  65

GAC TGG GGT CAA AAG CCC AAC GCC ACA GCC TGC CCC GAT GAG GCA TCC             297
Asp Trp Gly Gln Lys Pro Asn Ala Thr Ala Cys Pro Asp Glu Ala Ser
                 70                  75                  80

TGC GCT AAG AAC TGT ATC CTC AGT GGT ATG GAC TCA AAC GCT TAC AAG             345
Cys Ala Lys Asn Cys Ile Leu Ser Gly Met Asp Ser Asn Ala Tyr Lys
             85                  90                  95

AAC GCT GGT ATC ACT ACT TCT GGC AAC AAG CTT CGT CTT CAG CAG CTT             393
Asn Ala Gly Ile Thr Thr Ser Gly Asn Lys Leu Arg Leu Gln Gln Leu
        100                 105                 110

ATC AAC AAC CAG CTT GTT TCT CCT CGG GTT TAT CTG CTT GAG GAG AAC             441
Ile Asn Asn Gln Leu Val Ser Pro Arg Val Tyr Leu Leu Glu Glu Asn
    115                 120                 125

AAG AAG AAG TAT GAG ATG CTT CAG CTC ACT GGT ACT GAA TTC TCT TTC             489
Lys Lys Lys Tyr Glu Met Leu Gln Leu Thr Gly Thr Glu Phe Ser Phe
130                 135                 140                 145

GAC GTT GAG ATG GAG AAG CTT CCT TGT GGT ATG AAT GGT GCT TTG TAC             537
Asp Val Glu Met Glu Lys Leu Pro Cys Gly Met Asn Gly Ala Leu Tyr
                150                 155                 160

CTT TCC GAG ATG CCA CAG GAT GGT GGT AAG AGC ACG AGC CGA AAC AGC             585
Leu Ser Glu Met Pro Gln Asp Gly Gly Lys Ser Thr Ser Arg Asn Ser
            165                 170                 175

AAG GCT GGT GCC TAC TAT GGT GCT GGA TAC TGT GAT GCT CAG TGC TAC             633
Lys Ala Gly Ala Tyr Tyr Gly Ala Gly Tyr Cys Asp Ala Gln Cys Tyr
        180                 185                 190

GTC ACT CCT TTC ATC AAC GGA GTT GGC AAC ATC AAG GGA CAG GGT GTC             681
Val Thr Pro Phe Ile Asn Gly Val Gly Asn Ile Lys Gly Gln Gly Val
    195                 200                 205

TGC TGT AAC GAG CTC GAC ATC TGG GAG GCC AAC TCC CGC GCA ACT CAC             729
Cys Cys Asn Glu Leu Asp Ile Trp Glu Ala Asn Ser Arg Ala Thr His
210                 215                 220                 225

ATT GCT CCT CAC CCT TGC AGC AAG CCC GGC CTC TAC GGC TGC ACA GGC             777
Ile Ala Pro His Pro Cys Ser Lys Pro Gly Leu Tyr Gly Cys Thr Gly
                230                 235                 240

GAT GAG TGC GGC AGC TCC GGT TTC TGC GAC AAG GCC GGC TGC GGC TGG             825
Asp Glu Cys Gly Ser Ser Gly Phe Cys Asp Lys Ala Gly Cys Gly Trp
            245                 250                 255

AAC CAC AAC CGC ATC AAC GTG ACC GAC TTC TAC GGC CGC GGC AAG CAG             873
Asn His Asn Arg Ile Asn Val Thr Asp Phe Tyr Gly Arg Gly Lys Gln
        260                 265                 270
```

-continued

| | | | | | | | | | | | | | | | | |
|---|---|---|---|---|---|---|---|---|---|---|---|---|---|---|---|---|
|TAC|AAG|GTC|GAC|AGC|ACC|CGC|AAG|TTC|ACC|GTG|ACA|TCT|CAG|TTC|GTC|921|
|Tyr|Lys|Val|Asp|Ser|Thr|Arg|Lys|Phe|Thr|Val|Thr|Ser|Gln|Phe|Val| |
| |275| | | |280| | | | |285| | | | | | |
|GCC|AAC|AAG|CAG|GGT|GAT|CTC|ATC|GAG|CTG|CAC|CGC|CAC|TAC|ATC|CAG|969|
|Ala|Asn|Lys|Gln|Gly|Asp|Leu|Ile|Glu|Leu|His|Arg|His|Tyr|Ile|Gln| |
|290| | | | |295| | | | |300| | | | |305| |
|GAC|AAC|AAG|GTC|ATC|GAG|TCT|GCT|GTC|GTC|AAC|ATC|TCC|GGC|CCT|CCC|1017|
|Asp|Asn|Lys|Val|Ile|Glu|Ser|Ala|Val|Val|Asn|Ile|Ser|Gly|Pro|Pro| |
| | | | |310| | | | |315| | | | |320| | |
|AAG|ATC|AAC|TTC|ATC|AAT|GAC|AAG|TAC|TGC|GCT|GCC|ACC|GGC|GCC|AAC|1065|
|Lys|Ile|Asn|Phe|Ile|Asn|Asp|Lys|Tyr|Cys|Ala|Ala|Thr|Gly|Ala|Asn| |
| | | |325| | | |330| | | | |335| | | | |
|GAG|TAC|ATG|CGC|CTC|GGC|GGT|ACT|AAG|CAA|ATG|GGC|GAT|GCC|ATG|TCC|1113|
|Glu|Tyr|Met|Arg|Leu|Gly|Gly|Thr|Lys|Gln|Met|Gly|Asp|Ala|Met|Ser| |
| | |340| | | | |345| | | | |350| | | | |
|CGC|GGA|ATG|GTT|CTC|GCC|ATG|AGC|GTC|TGG|TGG|AGC|GAG|GGT|GAT|TTC|1161|
|Arg|Gly|Met|Val|Leu|Ala|Met|Ser|Val|Trp|Trp|Ser|Glu|Gly|Asp|Phe| |
| |355| | | | |360| | | | |365| | | | | |
|ATG|GCC|TGG|TTG|GAT|CAG|GGT|GTT|GCT|GGA|CCC|TGT|GAC|GCC|ACC|GAG|1209|
|Met|Ala|Trp|Leu|Asp|Gln|Gly|Val|Ala|Gly|Pro|Cys|Asp|Ala|Thr|Glu| |
|370| | | | |375| | | | |380| | | | |385| |
|GGC|GAT|CCC|AAG|AAC|ATC|GTC|AAG|GTG|CAG|CCC|AAC|CCT|GAA|GTG|ACA|1257|
|Gly|Asp|Pro|Lys|Asn|Ile|Val|Lys|Val|Gln|Pro|Asn|Pro|Glu|Val|Thr| |
| | | | |390| | | | |395| | | | |400| | |
|TTT|AGC|AAC|ATC|AGA|ATT|GGA|GAG|ATT|GGA|TCT|ACT|TCA|TCG|GTC|AAG|1305|
|Phe|Ser|Asn|Ile|Arg|Ile|Gly|Glu|Ile|Gly|Ser|Thr|Ser|Ser|Val|Lys| |
| | | |405| | | |410| | | | |415| | | | |
|GCT|CCT|GCG|TAT|CCT|GGT|CCT|CAC|CGC|TTG|TAAAAACATC|AAACAACACC| | | | |1355|
|Ala|Pro|Ala|Tyr|Pro|Gly|Pro|His|Arg|Leu| | | | | | | |
| | |420| | | |425| | | | | | | | | | |

| | |
|---|---|
|GTGTCCAATA TGGATCTTAG TGTCCACTTG CTGGGAAGCT ATTGGAGCAC ATATGCAAAA|1415|
|CAGATGTCCA CTAGCTTGAC ACGTATGTCG GGGCAAAAAA ATCTCTTTCT AGGATAGGAG|1475|
|AACATATTGG GTGTTGGAC TTGTATATAA ATGATACATT TTTCATATTA TATTATTTTC|1535|
|AACATATTTT ATTTCACGAA AAAAAAAAA AAAAAAAAA AAAAAAAA|1584|

( 2 ) INFORMATION FOR SEQ ID NO:25:

( i ) SEQUENCE CHARACTERISTICS:
        ( A ) LENGTH: 427 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
|Met|Lys|Ser|Leu|Ser|Leu|Ile|Leu|Ser|Ala|Leu|Ala|Val|Gln|Val|Ala|
|1| | | |5| | | | |10| | | | |15|
|Val|Ala|Gln|Thr|Pro|Asp|Lys|Ala|Lys|Glu|Gln|His|Pro|Lys|Leu|Glu|
| | | |20| | | | |25| | | | |30| |
|Thr|Tyr|Arg|Cys|Thr|Lys|Ala|Ser|Gly|Cys|Lys|Lys|Gln|Thr|Asn|Tyr|
| | |35| | | | |40| | | | |45| | |
|Ile|Val|Ala|Asp|Ala|Gly|Ile|His|Gly|Ile|Arg|Arg|Ser|Ala|Gly|Cys|
| |50| | | | |55| | | | |60| | | |
|Gly|Asp|Trp|Gly|Gln|Lys|Pro|Asn|Ala|Thr|Ala|Cys|Pro|Asp|Glu|Ala|
|65| | | | |70| | | | |75| | | | |80|
|Ser|Cys|Ala|Lys|Asn|Cys|Ile|Leu|Ser|Gly|Met|Asp|Ser|Asn|Ala|Tyr|
| | | | |85| | | | |90| | | | |95| |
|Lys|Asn|Ala|Gly|Ile|Thr|Thr|Ser|Gly|Asn|Lys|Leu|Arg|Leu|Gln|Gln|

```
                        100                       105                       110
Leu  Ile  Asn  Asn  Gln  Leu  Val  Ser  Pro  Arg  Val  Tyr  Leu  Leu  Glu  Glu
          115                      120                      125

Asn  Lys  Lys  Lys  Tyr  Glu  Met  Leu  Gln  Leu  Thr  Gly  Thr  Glu  Phe  Ser
     130                      135                      140

Phe  Asp  Val  Glu  Met  Glu  Lys  Leu  Pro  Cys  Gly  Met  Asn  Gly  Ala  Leu
145                      150                      155                      160

Tyr  Leu  Ser  Glu  Met  Pro  Gln  Asp  Gly  Gly  Lys  Ser  Thr  Ser  Arg  Asn
                    165                      170                      175

Ser  Lys  Ala  Gly  Ala  Tyr  Tyr  Gly  Ala  Gly  Tyr  Cys  Asp  Ala  Gln  Cys
               180                      185                      190

Tyr  Val  Thr  Pro  Phe  Ile  Asn  Gly  Val  Gly  Asn  Ile  Lys  Gly  Gln  Gly
          195                      200                      205

Val  Cys  Cys  Asn  Glu  Leu  Asp  Ile  Trp  Glu  Ala  Asn  Ser  Arg  Ala  Thr
     210                      215                      220

His  Ile  Ala  Pro  His  Pro  Cys  Ser  Lys  Pro  Gly  Leu  Tyr  Gly  Cys  Thr
225                      230                      235                      240

Gly  Asp  Glu  Cys  Gly  Ser  Ser  Gly  Phe  Cys  Asp  Lys  Ala  Gly  Cys  Gly
                    245                      250                      255

Trp  Asn  His  Asn  Arg  Ile  Asn  Val  Thr  Asp  Phe  Tyr  Gly  Arg  Gly  Lys
                260                      265                      270

Gln  Tyr  Lys  Val  Asp  Ser  Thr  Arg  Lys  Phe  Thr  Val  Thr  Ser  Gln  Phe
          275                      280                      285

Val  Ala  Asn  Lys  Gln  Gly  Asp  Leu  Ile  Glu  Leu  His  Arg  His  Tyr  Ile
     290                      295                      300

Gln  Asp  Asn  Lys  Val  Ile  Glu  Ser  Ala  Val  Val  Asn  Ile  Ser  Gly  Pro
305                      310                      315                      320

Pro  Lys  Ile  Asn  Phe  Ile  Asn  Asp  Lys  Tyr  Cys  Ala  Ala  Thr  Gly  Ala
                    325                      330                      335

Asn  Glu  Tyr  Met  Arg  Leu  Gly  Gly  Thr  Lys  Gln  Met  Gly  Asp  Ala  Met
               340                      345                      350

Ser  Arg  Gly  Met  Val  Leu  Ala  Met  Ser  Val  Trp  Trp  Ser  Glu  Gly  Asp
          355                      360                      365

Phe  Met  Ala  Trp  Leu  Asp  Gln  Gly  Val  Ala  Gly  Pro  Cys  Asp  Ala  Thr
     370                      375                      380

Glu  Gly  Asp  Pro  Lys  Asn  Ile  Val  Lys  Val  Gln  Pro  Asn  Pro  Glu  Val
385                      390                      395                      400

Thr  Phe  Ser  Asn  Ile  Arg  Ile  Gly  Glu  Ile  Gly  Ser  Thr  Ser  Ser  Val
                    405                      410                      415

Lys  Ala  Pro  Ala  Tyr  Pro  Gly  Pro  His  Arg  Leu
               420                      425
```

( 2 ) INFORMATION FOR SEQ ID NO:26:

( i ) SEQUENCE CHARACTERISTICS:
        ( A ) LENGTH: 1510 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Humicola insolens
        ( B ) STRAIN: DSM 1800

( i x ) FEATURE:

(A) NAME/KEY: CDS
(B) LOCATION: 109..1413

(xi) SEQUENCE DESCRIPTION: SEQ ID NO:26:

| | | | | | | |
|---|---|---|---|---|---|---|
| TTTCTTCGTC | GAGCTCGAGT | CGTCCGCCGT | CTCCTCCTCC | TCCTCCTTCC | AGTCTTTGAG | 60 |
| TTCCTTCGAC | CTGCAGCGTC | CTGAACAACT | CGCTCTAGCT | CAACAACC ATG GCT CGC | | 117 |
| | | | | Met Ala Arg | | |
| | | | | 1 | | |

```
GGT ACC GCT CTC CTC GGC CTG ACC GCG CTC CTC CTG GGG CTG GTC AAC          165
Gly Thr Ala Leu Leu Gly Leu Thr Ala Leu Leu Leu Gly Leu Val Asn
        5                  10                 15

GGC CAG AAG CCT GGT GAG ACC AAG GAG GTT CAC CCC CAG CTC ACG ACC          213
Gly Gln Lys Pro Gly Glu Thr Lys Glu Val His Pro Gln Leu Thr Thr
 20              25                  30                  35

TTC CGC TGC ACG AAG AGG GGT GGT TGC AAG CCG GCG ACC AAC TTC ATC          261
Phe Arg Cys Thr Lys Arg Gly Gly Cys Lys Pro Ala Thr Asn Phe Ile
             40                  45                  50

GTG CTT GAC TCG CTG TCG CAC CCC ATC CAC CGC GCT GAG GGC CTG GGC          309
Val Leu Asp Ser Leu Ser His Pro Ile His Arg Ala Glu Gly Leu Gly
                 55                  60                  65

CCT GGC GGC TGC GGC GAC TGG GGC AAC CCG CCG CCC AAG GAC GTC TGC          357
Pro Gly Gly Cys Gly Asp Trp Gly Asn Pro Pro Pro Lys Asp Val Cys
         70                  75                  80

CCG GAC GTC GAG TCG TGC GCC AAG AAC TGC ATC ATG GAG GGC ATC CCC          405
Pro Asp Val Glu Ser Cys Ala Lys Asn Cys Ile Met Glu Gly Ile Pro
 85                  90                  95

GAC TAC AGC CAG TAC GGC GTC ACC ACC AAC GGC ACC AGC CTC CGC CTG          453
Asp Tyr Ser Gln Tyr Gly Val Thr Thr Asn Gly Thr Ser Leu Arg Leu
100                 105                 110                 115

CAG CAC ATC CTC CCC GAC GGC CGC GTC CCG TCG CCG CGT GTC TAC CTG          501
Gln His Ile Leu Pro Asp Gly Arg Val Pro Ser Pro Arg Val Tyr Leu
                 120                 125                 130

CTC GAC AAG ACG AAG CGC CGC TAT GAG ATG CTC CAC CTG ACC GGC TTC          549
Leu Asp Lys Thr Lys Arg Arg Tyr Glu Met Leu His Leu Thr Gly Phe
             135                 140                 145

GAG TTC ACC TTC GAC GTC GAC GCC ACC AAG CTG CCC TGC GGC ATG AAC          597
Glu Phe Thr Phe Asp Val Asp Ala Thr Lys Leu Pro Cys Gly Met Asn
         150                 155                 160

AGC GCT CTG TAC CTG TCC GAG ATG CAC CCG ACC GGT GCC AAG AGC AAG          645
Ser Ala Leu Tyr Leu Ser Glu Met His Pro Thr Gly Ala Lys Ser Lys
165                 170                 175

TAC AAC TCC GGC GGT GCC TAC TAC GGT ACT GGC TAC TGC GAT GCT CAG          693
Tyr Asn Ser Gly Gly Ala Tyr Tyr Gly Thr Gly Tyr Cys Asp Ala Gln
180                 185                 190                 195

TGC TTC GTG ACG CCC TTC ATC AAC GGC TTG GGC AAC ATC GAG GGC AAG          741
Cys Phe Val Thr Pro Phe Ile Asn Gly Leu Gly Asn Ile Glu Gly Lys
             200                 205                 210

GGC TCG TGC TGC AAC GAG ATG GAT ATC TGG GAG GTC AAC TCG CGC GCC          789
Gly Ser Cys Cys Asn Glu Met Asp Ile Trp Glu Val Asn Ser Arg Ala
             215                 220                 225

TCG CAC GTG GTT CCC CAC ACC TGC AAC AAG AAG GGC CTG TAC CTT TGC          837
Ser His Val Val Pro His Thr Cys Asn Lys Lys Gly Leu Tyr Leu Cys
         230                 235                 240

GAG GGT GAG GAG TGC GCC TTC GAG GGT GTT TGC GAC AAG AAC GGC TGC          885
Glu Gly Glu Glu Cys Ala Phe Glu Gly Val Cys Asp Lys Asn Gly Cys
245                 250                 255

GGC TGG AAC AAC TAC CGC GTC AAC GTG ACT GAC TAC TAC GGC CGG GGC          933
Gly Trp Asn Asn Tyr Arg Val Asn Val Thr Asp Tyr Tyr Gly Arg Gly
260                 265                 270                 275

GAG GAG TTC AAG GTC AAC ACC CTC AAG CCC TTC ACC GTC GTC ACT CAG          981
```

-continued

| | | | | | | | | | | | | | | |
|---|---|---|---|---|---|---|---|---|---|---|---|---|---|---|
| Glu | Glu | Phe | Lys | Val 280 | Asn | Thr | Leu | Lys | Pro 285 | Phe | Thr | Val | Val | Thr 290 | Gln |

```
TTC TTG GCC AAC CGC AGG GGC AAG CTC GAG AAG ATC CAC CGC TTC TAC         1029
Phe Leu Ala Asn Arg Arg Gly Lys Leu Glu Lys Ile His Arg Phe Tyr
            295             300             305

GTG CAG GAC GGC AAG GTC ATC GAG TCC TTC TAC ACC AAC AAG GAG GGA         1077
Val Gln Asp Gly Lys Val Ile Glu Ser Phe Tyr Thr Asn Lys Glu Gly
        310             315             320

GTC CCT TAC ACC AAC ATG ATC GAT GAC GAG TTC TGC GAG GCC ACC GGC         1125
Val Pro Tyr Thr Asn Met Ile Asp Asp Glu Phe Cys Glu Ala Thr Gly
    325             330             335

TCC CGC AAG TAC ATG GAG CTC GGC GCC ACC CAG GGC ATG GGC GAG GCC         1173
Ser Arg Lys Tyr Met Glu Leu Gly Ala Thr Gln Gly Met Gly Glu Ala
340             345             350             355

CTC ACC CGC GGC ATG GTC CTG GCC ATG AGC ATC TGG TGG GAC CAG GGC         1221
Leu Thr Arg Gly Met Val Leu Ala Met Ser Ile Trp Trp Asp Gln Gly
            360             365             370

GGC AAC ATG GAG TGG CTC GAC CAC GGC GAG GCC GGC CCC TGC GCC AAG         1269
Gly Asn Met Glu Trp Leu Asp His Gly Glu Ala Gly Pro Cys Ala Lys
        375             380             385

GGC GAG GGC GCC CCG TCC AAC ATT GTC CAG GTT GAG CCC TTC CCC GAG         1317
Gly Glu Gly Ala Pro Ser Asn Ile Val Gln Val Glu Pro Phe Pro Glu
    390             395             400

GTC ACC TAC ACC AAC CTC CGC TGG GGC GAG ATC GGC TCG ACC TAC CAG         1365
Val Thr Tyr Thr Asn Leu Arg Trp Gly Glu Ile Gly Ser Thr Tyr Gln
405             410             415

GAG GTT CAG AAG CCT AAG CCC AAG CCC GGC CAC GGC CCC CGG AGC GAC         1413
Glu Val Gln Lys Pro Lys Pro Lys Pro Gly His Gly Pro Arg Ser Asp
420             425             430             435

TAAGTGGTGA TGGGATAGAG GGATAGAATA GTGGATAGCA CATAGATCGG CGGTTTTGGA       1473

TAGTTTAATA CATTCCGTTG CCGTTGTGAA AAAAAAA                                1510
```

( 2 ) INFORMATION FOR SEQ ID NO:27:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Ala Arg Gly Thr Ala Leu Leu Gly Leu Thr Ala Leu Leu Leu Gly
 1               5                  10                  15

Leu Val Asn Gly Gln Lys Pro Gly Glu Thr Lys Glu Val His Pro Gln
            20                  25                  30

Leu Thr Thr Phe Arg Cys Thr Lys Arg Gly Gly Cys Lys Pro Ala Thr
        35                  40                  45

Asn Phe Ile Val Leu Asp Ser Leu Ser His Pro Ile His Arg Ala Glu
    50                  55                  60

Gly Leu Gly Pro Gly Gly Cys Gly Asp Trp Gly Asn Pro Pro Pro Lys
65                  70                  75                  80

Asp Val Cys Pro Asp Val Glu Ser Cys Ala Lys Asn Cys Ile Met Glu
                85                  90                  95

Gly Ile Pro Asp Tyr Ser Gln Tyr Gly Val Thr Thr Asn Gly Thr Ser
                100                 105                 110

Leu Arg Leu Gln His Ile Leu Pro Asp Gly Arg Val Pro Ser Pro Arg
        115                 120                 125

Val Tyr Leu Leu Asp Lys Thr Lys Arg Arg Tyr Glu Met Leu His Leu
```

|     |     |     |     |     | 130 |     |     |     |     | 135 |     |     |     |     | 140 |     |     |     |     |
|-----|-----|-----|-----|-----|-----|-----|-----|-----|-----|-----|-----|-----|-----|-----|-----|-----|-----|-----|-----|
| Thr<br>145 | Gly | Phe | Glu | Phe | Thr<br>150 | Phe | Asp | Val | Asp | Ala<br>155 | Thr | Lys | Leu | Pro | Cys<br>160 |
| Gly | Met | Asn | Ser | Ala<br>165 | Leu | Tyr | Leu | Ser | Glu<br>170 | Met | His | Pro | Thr | Gly<br>175 | Ala |
| Lys | Ser | Lys | Tyr<br>180 | Asn | Ser | Gly | Gly | Ala<br>185 | Tyr | Tyr | Gly | Thr | Gly<br>190 | Tyr | Cys |
| Asp | Ala | Gln<br>195 | Cys | Phe | Val | Thr | Pro<br>200 | Phe | Ile | Asn | Gly | Leu<br>205 | Gly | Asn | Ile |
| Glu | Gly | Lys<br>210 | Gly | Ser | Cys | Cys<br>215 | Asn | Glu | Met | Asp | Ile<br>220 | Trp | Glu | Val | Asn |
| Ser<br>225 | Arg | Ala | Ser | His | Val<br>230 | Val | Pro | His | Thr | Cys<br>235 | Asn | Lys | Lys | Gly | Leu<br>240 |
| Tyr | Leu | Cys | Glu | Gly<br>245 | Glu | Glu | Cys | Ala | Phe<br>250 | Glu | Gly | Val | Cys | Asp<br>255 | Lys |
| Asn | Gly | Cys | Gly<br>260 | Trp | Asn | Asn | Tyr | Arg<br>265 | Val | Asn | Val | Thr | Asp<br>270 | Tyr | Tyr |
| Gly | Arg | Gly<br>275 | Glu | Glu | Phe | Lys | Val<br>280 | Asn | Thr | Leu | Lys | Pro<br>285 | Phe | Thr | Val |
| Val | Thr<br>290 | Gln | Phe | Leu | Ala | Asn<br>295 | Arg | Arg | Gly | Lys | Leu<br>300 | Glu | Lys | Ile | His |
| Arg<br>305 | Phe | Tyr | Val | Gln | Asp<br>310 | Gly | Lys | Val | Ile | Glu<br>315 | Ser | Phe | Tyr | Thr | Asn<br>320 |
| Lys | Glu | Gly | Val | Pro<br>325 | Tyr | Thr | Asn | Met | Ile<br>330 | Asp | Asp | Glu | Phe | Cys<br>335 | Glu |
| Ala | Thr | Gly | Ser<br>340 | Arg | Lys | Tyr | Met | Glu<br>345 | Leu | Gly | Ala | Thr | Gln<br>350 | Gly | Met |
| Gly | Glu | Ala<br>355 | Leu | Thr | Arg | Gly | Met<br>360 | Val | Leu | Ala | Met | Ser<br>365 | Ile | Trp | Trp |
| Asp | Gln<br>370 | Gly | Gly | Asn | Met | Glu<br>375 | Trp | Leu | Asp | His | Gly<br>380 | Glu | Ala | Gly | Pro |
| Cys<br>385 | Ala | Lys | Gly | Glu | Gly<br>390 | Ala | Pro | Ser | Asn | Ile<br>395 | Val | Gln | Val | Glu | Pro<br>400 |
| Phe | Pro | Glu | Val | Thr<br>405 | Tyr | Thr | Asn | Leu | Arg<br>410 | Trp | Gly | Glu | Ile | Gly<br>415 | Ser |
| Thr | Tyr | Gln | Glu<br>420 | Val | Gln | Lys | Pro | Lys<br>425 | Pro | Lys | Pro | Gly | His<br>430 | Gly | Pro |
| Arg | Ser | Asp<br>435 |

( 2 ) INFORMATION FOR SEQ ID NO:28:

( i ) SEQUENCE CHARACTERISTICS:
        ( A ) LENGTH: 1854 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Bacillus lautus/Humicola insolens ( i x ) FEATURE:
        ( A ) NAME/KEY: CDS
        ( B ) LOCATION: 1..1851

( x i ) SEQUENCE DESCRIPTION: SEQ ID NO:28:

| | | | | | | | | | | | | | | | | |
|---|---|---|---|---|---|---|---|---|---|---|---|---|---|---|---|---|
| ATG | CGT | TCC | TCC | CCC | CTC | CTC | CCG | TCC | GCC | GTT | GTG | GCC | GCC | CTG | CCG | 48 |
| Met | Arg | Ser | Ser | Pro | Leu | Leu | Pro | Ser | Ala | Val | Val | Ala | Ala | Leu | Pro | |
| 1 | | | | 5 | | | | | 10 | | | | | 15 | | |
| GTG | TTG | GCC | CTT | GCC | GCT | GAT | GGC | AGG | AGT | GAT | GTC | ACT | TTC | ACG | ATT | 96 |
| Val | Leu | Ala | Leu | Ala | Ala | Asp | Gly | Arg | Ser | Asp | Val | Thr | Phe | Thr | Ile | |
| | | | 20 | | | | | 25 | | | | | 30 | | | |
| AAT | ACG | CAG | TCG | GAA | CGT | GCA | GCG | ATC | AGC | CCC | AAT | ATT | TAC | GGA | ACC | 144 |
| Asn | Thr | Gln | Ser | Glu | Arg | Ala | Ala | Ile | Ser | Pro | Asn | Ile | Tyr | Gly | Thr | |
| | | 35 | | | | | 40 | | | | | 45 | | | | |
| AAT | CAG | GAT | CTG | AGC | GGG | ACG | GAG | AAC | TGG | TCA | TCC | CGC | AGG | CTC | GGA | 192 |
| Asn | Gln | Asp | Leu | Ser | Gly | Thr | Glu | Asn | Trp | Ser | Ser | Arg | Arg | Leu | Gly | |
| | 50 | | | | | 55 | | | | | 60 | | | | | |
| GGC | AAC | CGG | CTG | ACG | GGT | TAC | AAC | TGG | GAG | AAC | AAC | GCA | TCC | AGC | GCC | 240 |
| Gly | Asn | Arg | Leu | Thr | Gly | Tyr | Asn | Trp | Glu | Asn | Asn | Ala | Ser | Ser | Ala | |
| 65 | | | | | 70 | | | | | 75 | | | | | 80 | |
| GGA | AGG | GAC | TGG | CTT | CAT | TAC | AGC | GAT | GAT | TTT | CTC | TGC | GGC | AAC | GGT | 288 |
| Gly | Arg | Asp | Trp | Leu | His | Tyr | Ser | Asp | Asp | Phe | Leu | Cys | Gly | Asn | Gly | |
| | | | | 85 | | | | | 90 | | | | | 95 | | |
| GGT | GTT | CCA | GAC | ACC | GAC | TGC | GAC | AAG | CCG | GGG | GCG | GTT | GTT | ACC | GCT | 336 |
| Gly | Val | Pro | Asp | Thr | Asp | Cys | Asp | Lys | Pro | Gly | Ala | Val | Val | Thr | Ala | |
| | | | 100 | | | | | 105 | | | | | 110 | | | |
| TTT | CAC | GAT | AAA | TCT | TTG | GAG | AAT | GGA | GCT | TAC | TCC | ATT | GTA | ACG | CTG | 384 |
| Phe | His | Asp | Lys | Ser | Leu | Glu | Asn | Gly | Ala | Tyr | Ser | Ile | Val | Thr | Leu | |
| | | 115 | | | | | 120 | | | | | 125 | | | | |
| CAA | ATG | GCG | GGT | TAT | GTG | TCC | CGG | GAT | AAG | AAC | GGT | CCA | GTT | GAC | GAG | 432 |
| Gln | Met | Ala | Gly | Tyr | Val | Ser | Arg | Asp | Lys | Asn | Gly | Pro | Val | Asp | Glu | |
| | 130 | | | | | 135 | | | | | 140 | | | | | |
| AGT | GAG | ACG | GCT | CCG | TCA | CCG | CGT | TGG | GAT | AAG | GTC | GAG | TTT | GCC | AAA | 480 |
| Ser | Glu | Thr | Ala | Pro | Ser | Pro | Arg | Trp | Asp | Lys | Val | Glu | Phe | Ala | Lys | |
| 145 | | | | | 150 | | | | | 155 | | | | | 160 | |
| AAT | GCG | CCG | TTC | TCC | CTT | CAG | CCT | GAT | CTG | AAC | GAC | GGA | CAA | GTG | TAT | 528 |
| Asn | Ala | Pro | Phe | Ser | Leu | Gln | Pro | Asp | Leu | Asn | Asp | Gly | Gln | Val | Tyr | |
| | | | | 165 | | | | | 170 | | | | | 175 | | |
| ATG | GAT | GAA | GAA | GTT | AAC | TTC | CTG | GTC | AAC | CGG | TAT | GGA | AAC | GCT | TCA | 576 |
| Met | Asp | Glu | Glu | Val | Asn | Phe | Leu | Val | Asn | Arg | Tyr | Gly | Asn | Ala | Ser | |
| | | | 180 | | | | | 185 | | | | | 190 | | | |
| ACG | TCA | ACG | GGC | ATC | AAA | GCG | TAT | TCG | CTG | GAT | AAC | GAG | CCG | GCG | CTG | 624 |
| Thr | Ser | Thr | Gly | Ile | Lys | Ala | Tyr | Ser | Leu | Asp | Asn | Glu | Pro | Ala | Leu | |
| | | 195 | | | | | 200 | | | | | 205 | | | | |
| TGG | TCT | GAG | ACG | CAT | CCA | AGG | ATT | CAT | CCG | GAG | CAG | TTA | CAA | GCG | GCA | 672 |
| Trp | Ser | Glu | Thr | His | Pro | Arg | Ile | His | Pro | Glu | Gln | Leu | Gln | Ala | Ala | |
| | 210 | | | | | 215 | | | | | 220 | | | | | |
| GAA | CTC | GTC | GCT | AAG | AGC | ATC | GAC | TTG | TCA | AAG | GCG | GTG | AAG | AAC | GTC | 720 |
| Glu | Leu | Val | Ala | Lys | Ser | Ile | Asp | Leu | Ser | Lys | Ala | Val | Lys | Asn | Val | |
| 225 | | | | | 230 | | | | | 235 | | | | | 240 | |
| GAT | CCG | CAT | GCC | GAA | ATA | TTC | GGT | CCT | GCC | CTT | TAC | GGT | TTC | GGC | GCA | 768 |
| Asp | Pro | His | Ala | Glu | Ile | Phe | Gly | Pro | Ala | Leu | Tyr | Gly | Phe | Gly | Ala | |
| | | | | 245 | | | | | 250 | | | | | 255 | | |
| TAT | TTG | TCT | CTG | CAG | GAC | GCA | CCG | GAT | TGG | CCG | AGT | TTG | CAA | GGC | AAC | 816 |
| Tyr | Leu | Ser | Leu | Gln | Asp | Ala | Pro | Asp | Trp | Pro | Ser | Leu | Gln | Gly | Asn | |
| | | | 260 | | | | | 265 | | | | | 270 | | | |
| TAC | AGC | TGG | TTT | ATC | GAT | TAC | TAT | CTG | GAT | CAG | ATG | AAG | AAT | GCT | CAT | 864 |
| Tyr | Ser | Trp | Phe | Ile | Asp | Tyr | Tyr | Leu | Asp | Gln | Met | Lys | Asn | Ala | His | |
| | | 275 | | | | | 280 | | | | | 285 | | | | |
| ACG | CAG | AAC | GGC | AAA | AGA | TTG | CTC | GAT | GTG | CTG | GAC | GTC | CAC | TGG | TAT | 912 |
| Thr | Gln | Asn | Gly | Lys | Arg | Leu | Leu | Asp | Val | Leu | Asp | Val | His | Trp | Tyr | |
| | 290 | | | | | 295 | | | | | 300 | | | | | |
| CCG | GAA | GCA | CAG | GGC | GGA | GGC | CAG | CGA | ATC | GTC | TTT | GGC | GGG | GCG | GGC | 960 |
| Pro | Glu | Ala | Gln | Gly | Gly | Gly | Gln | Arg | Ile | Val | Phe | Gly | Gly | Ala | Gly | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| AAT | ATC | GAT | ACG | CAG | AAG | GCT | CGC | GTA | CAA | GCG | CCA | AGA | TCG | CTA | TGG | 1008 |
| Asn | Ile | Asp | Thr | Gln | Lys | Ala | Arg | Val | Gln | Ala | Pro | Arg | Ser | Leu | Trp | |
| | | | | 325 | | | | | 330 | | | | | 335 | | |
| GAT | CCG | GCT | TAC | CAG | GAA | GAC | AGC | TGG | ATC | GGC | ACA | TGG | TTT | TCA | AGC | 1056 |
| Asp | Pro | Ala | Tyr | Gln | Glu | Asp | Ser | Trp | Ile | Gly | Thr | Trp | Phe | Ser | Ser | |
| | | | | 340 | | | | | 345 | | | | | 350 | | |
| TAC | TTG | CCC | TTA | ATT | CCG | AAG | CTG | CAA | TCT | TCG | ATT | CAG | ACG | TAT | TAT | 1104 |
| Tyr | Leu | Pro | Leu | Ile | Pro | Lys | Leu | Gln | Ser | Ser | Ile | Gln | Thr | Tyr | Tyr | |
| | | 355 | | | | | 360 | | | | | 365 | | | | |
| CCG | GGT | ACG | AAG | CTG | GCG | ATC | ACA | GAG | TTC | AGC | TAC | GGC | GGA | GAC | AAT | 1152 |
| Pro | Gly | Thr | Lys | Leu | Ala | Ile | Thr | Glu | Phe | Ser | Tyr | Gly | Gly | Asp | Asn | |
| | 370 | | | | | 375 | | | | | 380 | | | | | |
| CAC | ATT | TCG | GGA | GGC | ATA | GCT | ACC | GCG | GAC | GCG | CTC | GGC | ATT | TTT | GGA | 1200 |
| His | Ile | Ser | Gly | Gly | Ile | Ala | Thr | Ala | Asp | Ala | Leu | Gly | Ile | Phe | Gly | |
| 385 | | | | | 390 | | | | | 395 | | | | | 400 | |
| AAA | TAT | GGC | GTT | TAT | GCC | GCG | AAT | TAC | TGG | CAG | ACG | GAG | GAC | AAT | ACC | 1248 |
| Lys | Tyr | Gly | Val | Tyr | Ala | Ala | Asn | Tyr | Trp | Gln | Thr | Glu | Asp | Asn | Thr | |
| | | | | 405 | | | | | 410 | | | | | 415 | | |
| GAT | TAT | ACC | AGC | GCT | GCT | TAC | AAG | CTG | TAT | CGC | AAC | TAC | GAC | GGC | AAT | 1296 |
| Asp | Tyr | Thr | Ser | Ala | Ala | Tyr | Lys | Leu | Tyr | Arg | Asn | Tyr | Asp | Gly | Asn | |
| | | | 420 | | | | | 425 | | | | | 430 | | | |
| AAA | TCG | GGG | TTC | GGC | TCG | ATC | AAA | GTG | GAC | GCC | GCT | ACG | TCC | GAT | ACG | 1344 |
| Lys | Ser | Gly | Phe | Gly | Ser | Ile | Lys | Val | Asp | Ala | Ala | Thr | Ser | Asp | Thr | |
| | | 435 | | | | | 440 | | | | | 445 | | | | |
| GAG | AAC | AGC | TCG | GTA | TAC | GCT | TCG | GTA | ACT | GAC | GAG | GAG | AAT | TCC | GAA | 1392 |
| Glu | Asn | Ser | Ser | Val | Tyr | Ala | Ser | Val | Thr | Asp | Glu | Glu | Asn | Ser | Glu | |
| | 450 | | | | | 455 | | | | | 460 | | | | | |
| CTC | CAC | CTG | ATC | GTG | CTG | AAT | AAA | AAT | TTC | GAC | GAT | CCG | ATC | AAC | GCT | 1440 |
| Leu | His | Leu | Ile | Val | Leu | Asn | Lys | Asn | Phe | Asp | Asp | Pro | Ile | Asn | Ala | |
| 465 | | | | | 470 | | | | | 475 | | | | | 480 | |
| ACT | TTC | CAG | CTG | TCT | GGT | GAT | AAA | ACC | TAC | ACA | TCC | GGG | AGA | GTA | TGG | 1488 |
| Thr | Phe | Gln | Leu | Ser | Gly | Asp | Lys | Thr | Tyr | Thr | Ser | Gly | Arg | Val | Trp | |
| | | | | 485 | | | | | 490 | | | | | 495 | | |
| GGC | TTC | GAC | CAA | ACC | GGA | TCC | GAC | ATT | ACG | GAA | CAA | GCA | GCT | ATA | ACG | 1536 |
| Gly | Phe | Asp | Gln | Thr | Gly | Ser | Asp | Ile | Thr | Glu | Gln | Ala | Ala | Ile | Thr | |
| | | | | 500 | | | | | 505 | | | | | 510 | | |
| AAT | ATT | AAC | AAC | AAT | CAA | TTC | ACG | TAT | ACG | CTT | CCT | CCA | TTG | TCG | GCT | 1584 |
| Asn | Ile | Asn | Asn | Asn | Gln | Phe | Thr | Tyr | Thr | Leu | Pro | Pro | Leu | Ser | Ala | |
| | | | 515 | | | | | 520 | | | | | 525 | | | |
| TAC | CAC | ATT | GTT | CTG | AAA | GCG | GAT | AGC | ACC | GAA | CCG | GTC | ATC | TCC | GAG | 1632 |
| Tyr | His | Ile | Val | Leu | Lys | Ala | Asp | Ser | Thr | Glu | Pro | Val | Ile | Ser | Glu | |
| | 530 | | | | | 535 | | | | | 540 | | | | | |
| ATC | CCC | TCC | AGC | AGC | ACC | AGC | TCT | CCG | GTC | AAC | CAG | CCT | ACC | AGC | ACC | 1680 |
| Ile | Pro | Ser | Ser | Ser | Thr | Ser | Ser | Pro | Val | Asn | Gln | Pro | Thr | Ser | Thr | |
| 545 | | | | | 550 | | | | | 555 | | | | | 560 | |
| AGC | ACC | ACG | TCC | ACC | TCC | ACC | ACC | TCG | AGC | CCG | CCA | GTC | CAG | CCT | ACG | 1728 |
| Ser | Thr | Thr | Ser | Thr | Ser | Thr | Thr | Ser | Ser | Pro | Pro | Val | Gln | Pro | Thr | |
| | | | 565 | | | | | 570 | | | | | 575 | | | |
| ACT | CCC | AGC | GGC | TGC | ACT | GCT | GAG | AGG | TGG | GCT | CAG | TGC | GGC | GGC | AAT | 1776 |
| Thr | Pro | Ser | Gly | Cys | Thr | Ala | Glu | Arg | Trp | Ala | Gln | Cys | Gly | Gly | Asn | |
| | | | 580 | | | | | 585 | | | | | 590 | | | |
| GGC | TGG | AGC | GGC | TGC | ACC | ACC | TGC | GTC | GCT | GGC | AGC | ACT | TGC | ACG | AAG | 1824 |
| Gly | Trp | Ser | Gly | Cys | Thr | Thr | Cys | Val | Ala | Gly | Ser | Thr | Cys | Thr | Lys | |
| | | 595 | | | | | 600 | | | | | 605 | | | | |
| ATT | AAT | GAC | TGG | TAC | CAT | CAG | TGC | CTG | TAG | | | | | | | 1854 |
| Ile | Asn | Asp | Trp | Tyr | His | Gln | Cys | Leu | | | | | | | | |
| 610 | | | | | 615 | | | | | | | | | | | |

( 2 ) INFORMATION FOR SEQ ID NO:29:

( i ) SEQUENCE CHARACTERISTICS:
  ( A ) LENGTH: 617 amino acids
  ( B ) TYPE: amino acid
  ( D ) TOPOLOGY: linear ( i i ) MOLECULE TYPE: protein ( x i ) SEQUENCE DESCRIPTION: SEQ ID NO:29:

```
Met Arg Ser Ser Pro Leu Leu Pro Ser Ala Val Val Ala Ala Leu Pro
 1               5                  10                  15

Val Leu Ala Leu Ala Ala Asp Gly Arg Ser Asp Val Thr Phe Thr Ile
            20                  25                  30

Asn Thr Gln Ser Glu Arg Ala Ala Ile Ser Pro Asn Ile Tyr Gly Thr
        35                  40                  45

Asn Gln Asp Leu Ser Gly Thr Glu Asn Trp Ser Ser Arg Arg Leu Gly
    50                  55                  60

Gly Asn Arg Leu Thr Gly Tyr Asn Trp Glu Asn Ala Ser Ser Ala
 65                  70                  75                  80

Gly Arg Asp Trp Leu His Tyr Ser Asp Asp Phe Leu Cys Gly Asn Gly
                    85                  90                  95

Gly Val Pro Asp Thr Asp Cys Asp Lys Pro Gly Ala Val Val Thr Ala
                100                 105                 110

Phe His Asp Lys Ser Leu Glu Asn Gly Ala Tyr Ser Ile Val Thr Leu
            115                 120                 125

Gln Met Ala Gly Tyr Val Ser Arg Asp Lys Asn Gly Pro Val Asp Glu
        130                 135                 140

Ser Glu Thr Ala Pro Ser Pro Arg Trp Asp Lys Val Glu Phe Ala Lys
145                 150                 155                 160

Asn Ala Pro Phe Ser Leu Gln Pro Asp Leu Asn Asp Gly Gln Val Tyr
                    165                 170                 175

Met Asp Glu Glu Val Asn Phe Leu Val Asn Arg Tyr Gly Asn Ala Ser
                180                 185                 190

Thr Ser Thr Gly Ile Lys Ala Tyr Ser Leu Asp Asn Glu Pro Ala Leu
            195                 200                 205

Trp Ser Glu Thr His Pro Arg Ile His Pro Glu Gln Leu Gln Ala Ala
210                 215                 220

Glu Leu Val Ala Lys Ser Ile Asp Leu Ser Lys Ala Val Lys Asn Val
225                 230                 235                 240

Asp Pro His Ala Glu Ile Phe Gly Pro Ala Leu Tyr Gly Phe Gly Ala
                    245                 250                 255

Tyr Leu Ser Leu Gln Asp Ala Pro Asp Trp Pro Ser Leu Gln Gly Asn
                260                 265                 270

Tyr Ser Trp Phe Ile Asp Tyr Tyr Leu Asp Gln Met Lys Asn Ala His
            275                 280                 285

Thr Gln Asn Gly Lys Arg Leu Leu Asp Val Leu Asp Val His Trp Tyr
290                 295                 300

Pro Glu Ala Gln Gly Gly Gly Gln Arg Ile Val Phe Gly Gly Ala Gly
305                 310                 315                 320

Asn Ile Asp Thr Gln Lys Ala Arg Val Gln Ala Pro Arg Ser Leu Trp
                    325                 330                 335

Asp Pro Ala Tyr Gln Glu Asp Ser Trp Ile Gly Thr Trp Phe Ser Ser
                340                 345                 350

Tyr Leu Pro Leu Ile Pro Lys Leu Gln Ser Ser Ile Gln Thr Tyr Tyr
            355                 360                 365

Pro Gly Thr Lys Leu Ala Ile Thr Glu Phe Ser Tyr Gly Gly Asp Asn
370                 375                 380
```

| His | Ile | Ser | Gly | Gly | Ile | Ala | Thr | Ala | Asp | Ala | Leu | Gly | Ile | Phe | Gly |
| 385 | | | | 390 | | | | | 395 | | | | | | 400 |

| Lys | Tyr | Gly | Val | Tyr | Ala | Ala | Asn | Tyr | Trp | Gln | Thr | Glu | Asp | Asn | Thr |
| | | | | 405 | | | | | 410 | | | | | 415 | |

| Asp | Tyr | Thr | Ser | Ala | Ala | Tyr | Lys | Leu | Tyr | Arg | Asn | Tyr | Asp | Gly | Asn |
| | | | 420 | | | | | 425 | | | | | 430 | | |

| Lys | Ser | Gly | Phe | Gly | Ser | Ile | Lys | Val | Asp | Ala | Ala | Thr | Ser | Asp | Thr |
| | | 435 | | | | | 440 | | | | | 445 | | | |

| Glu | Asn | Ser | Ser | Val | Tyr | Ala | Ser | Val | Thr | Asp | Glu | Glu | Asn | Ser | Glu |
| | 450 | | | | | 455 | | | | | 460 | | | | |

| Leu | His | Leu | Ile | Val | Leu | Asn | Lys | Asn | Phe | Asp | Asp | Pro | Ile | Asn | Ala |
| 465 | | | | | 470 | | | | | 475 | | | | | 480 |

| Thr | Phe | Gln | Leu | Ser | Gly | Asp | Lys | Thr | Tyr | Thr | Ser | Gly | Arg | Val | Trp |
| | | | | 485 | | | | | 490 | | | | | 495 | |

| Gly | Phe | Asp | Gln | Thr | Gly | Ser | Asp | Ile | Thr | Glu | Gln | Ala | Ala | Ile | Thr |
| | | | 500 | | | | | 505 | | | | 510 | | | |

| Asn | Ile | Asn | Asn | Asn | Gln | Phe | Thr | Tyr | Thr | Leu | Pro | Pro | Leu | Ser | Ala |
| | | | 515 | | | | | 520 | | | | 525 | | | |

| Tyr | His | Ile | Val | Leu | Lys | Ala | Asp | Ser | Thr | Glu | Pro | Val | Ile | Ser | Glu |
| | 530 | | | | | 535 | | | | | 540 | | | | |

| Ile | Pro | Ser | Ser | Ser | Thr | Ser | Ser | Pro | Val | Asn | Gln | Pro | Thr | Ser | Thr |
| 545 | | | | | 550 | | | | | 555 | | | | | 560 |

| Ser | Thr | Thr | Ser | Thr | Ser | Thr | Thr | Ser | Ser | Pro | Pro | Val | Gln | Pro | Thr |
| | | | | 565 | | | | | 570 | | | | | 575 | |

| Thr | Pro | Ser | Gly | Cys | Thr | Ala | Glu | Arg | Trp | Ala | Gln | Cys | Gly | Gly | Asn |
| | | | 580 | | | | | 585 | | | | | 590 | | |

| Gly | Trp | Ser | Gly | Cys | Thr | Thr | Cys | Val | Ala | Gly | Ser | Thr | Cys | Thr | Lys |
| | | 595 | | | | | 600 | | | | | 605 | | | |

| Ile | Asn | Asp | Trp | Tyr | His | Gln | Cys | Leu |
| | 610 | | | | | 615 | | |

( 2 ) INFORMATION FOR SEQ ID NO:30:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

CTTGCACCCG CTGTACCCAA TGCCACCGCA CTGCCCCCA     39

( 2 ) INFORMATION FOR SEQ ID NO:31:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

CGTGGGGCCG CTGTAGCCAA TACCGCCGCA CTGGCCGTA    39

( 2 ) INFORMATION FOR SEQ ID NO:32:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

AGTCGGACCC GACCAATTCT GGCCACCACA TTGGCCCCA    39

( 2 ) INFORMATION FOR SEQ ID NO:33:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

CGTAGGTCCG CTCCAACCAA TACCTCCACA CTGGCCCCA    39

( 2 ) INFORMATION FOR SEQ ID NO:34:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

GCCAACTACG GTACCGGNTA YTG YGAYDSN CARTG    35

( 2 ) INFORMATION FOR SEQ ID NO:35:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:35:

GCGTTGGCCT CTAGAATRTC CATYTCNBWR CARCA    35

( 2 ) INFORMATION FOR SEQ ID NO:36:

( i ) SEQUENCE CHARACTERISTICS:
　　　　　　　　( A ) LENGTH: 33 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:36:

TCCTGACGCC AAGCTTTDYW WHAAYGAYTA YAA　　　　　　　　　　　　　　　　　　33

( 2 ) INFORMATION FOR SEQ ID NO:37:

( i ) SEQUENCE CHARACTERISTICS:
　　　　　　　　( A ) LENGTH: 31 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:37:

CACCGGCACC ATCGATRTCN ARYTCNGTDA T　　　　　　　　　　　　　　　　　　　31

( 2 ) INFORMATION FOR SEQ ID NO:38:

( i ) SEQUENCE CHARACTERISTICS:
　　　　　　　　( A ) LENGTH: 44 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:38:

GACAGAGCAC AGAATTCACT AGTGAGCTCT TTTTTTTTTT TTTT　　　　　　　　　　　　44

( 2 ) INFORMATION FOR SEQ ID NO:39:

( i ) SEQUENCE CHARACTERISTICS:
　　　　　　　　( A ) LENGTH: 40 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:39:

ATTACCAACA CCAGCGTTGA CATCACTGTC AGAGGGCTTC　　　　　　　　　　　　　　40

( 2 ) INFORMATION FOR SEQ ID NO:40:

( i ) SEQUENCE CHARACTERISTICS:
　　　　　　　　( A ) LENGTH: 28 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (genomic)

( x i ) SEQUENCE DESCRIPTION: SEQ ID NO:40:

AACTCCGTTG ATGAAAGGAG TGACGTAG　　　　　　　　　　　　　　　　　　　　　　28

( 2 ) INFORMATION FOR SEQ ID NO:41:

( i ) SEQUENCE CHARACTERISTICS:
　　　　　　　　( A ) LENGTH: 40 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

CGGAGAGCAG CAGGAACACC AGAGGCAGGG TTCCAGCCAC 40

( 2 ) INFORMATION FOR SEQ ID NO:42:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

ATTGTTCTCG TTCCCTTTCT T 21

( 2 ) INFORMATION FOR SEQ ID NO:43:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

TGTACGCATG TAACATTA 18

( 2 ) INFORMATION FOR SEQ ID NO:44:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

TGATGTCAAG TTCATCAA 18

( 2 ) INFORMATION FOR SEQ ID NO:45:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

TCTGTACGTC CAGAACGG 18

( 2 ) INFORMATION FOR SEQ ID NO:46:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

ATGACTTCTC TAAGAAGG  18

( 2 ) INFORMATION FOR SEQ ID NO:47:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TCCAACATCA AGTTCGGT  18

( 2 ) INFORMATION FOR SEQ ID NO:48:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

AGGCCAACTC CATCTGAA  18

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

ATTACCAACA CCAGCGTTGA CATCACTGTC AGAGGGCTCC  40

( 2 ) INFORMATION FOR SEQ ID NO:50:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

CCGTTCTGGA CGTACAGA  18

( 2 ) INFORMATION FOR SEQ ID NO:51:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CCATCGACGG TATTGGAT  18

( 2 ) INFORMATION FOR SEQ ID NO:52:

( i ) SEQUENCE CHARACTERISTICS:
　　　　( A ) LENGTH: 40 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:52:

CGGAGAGCAG CAGGAACACC AGAGGCAGGG TTCCAGCCAC                    40

( 2 ) INFORMATION FOR SEQ ID NO:53:

( i ) SEQUENCE CHARACTERISTICS:
　　　　( A ) LENGTH: 18 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:53:

GAGGGTAGAG CGATCGTT                                           18

( 2 ) INFORMATION FOR SEQ ID NO:54:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:54:

TGATCTCATC GAGCTGCACC                                         20

( 2 ) INFORMATION FOR SEQ ID NO:55:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:55:

GTGATGCTCA GTGCTACGTC                                         20

( 2 ) INFORMATION FOR SEQ ID NO:56:

( i ) SEQUENCE CHARACTERISTICS:
　　　　( A ) LENGTH: 28 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:56:

AACTCCGTTG ATGAAAGGAG TGACGTAG                                28

( 2 ) INFORMATION FOR SEQ ID NO:57:

( i ) SEQUENCE CHARACTERISTICS:
　　　　( A ) LENGTH: 20 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:57:

TCCAATAGCT TCCCAGCAAG    20

( 2 ) INFORMATION FOR SEQ ID NO:58:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:58:

TGTCCCTTGA TGTTGCCAAC    20

( 2 ) INFORMATION FOR SEQ ID NO:59:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:59:

GCTTCGCCCA TGCCTTGGGT GGCGCCGAGT TCCAT    35

( 2 ) INFORMATION FOR SEQ ID NO:60:

( i ) SEQUENCE CHARACTERISTICS:
( A ) LENGTH: 69 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:60:

GTCACCTACA CCAACCTCCG CTGGGGCGAG ATCGGCTCGA CCTACCAGGA GCTGCAGTAG    60

TAATGATAG    69

( 2 ) INFORMATION FOR SEQ ID NO:61:

( i ) SEQUENCE CHARACTERISTICS:
( A ) LENGTH: 68 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:61:

GATCCTATCA TTACTACTGC AGCTCCTGGT AGGTCGAGCC GATCTCGCCC CAGCGGAGGT    60

TGGTGTAG    68

( 2 ) INFORMATION FOR SEQ ID NO:62:

( i ) SEQUENCE CHARACTERISTICS:
( A ) LENGTH: 102 base pairs
( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:62:

GTCACCTACA CCAACCTCCG CTGGGGCGAG ATCGGCTCGA CCTACCAGGA GGTTCAGAAG　　60

CCTAAGCCCA AGCCCGGGCA CGGCCCCCGA TCGGACTAAT AG　　102

( 2 ) INFORMATION FOR SEQ ID NO:63:

( i ) SEQUENCE CHARACTERISTICS:
    ( A ) LENGTH: 101 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:63:

GATCCTATTA GTCCGATCGG GGGCCGTGCC CGGGCTTGGG CTTAGGCTTC TGAACCTCCT　　60

GGTAGGTCGA GCCGATCTCG CCCCAGCGGA GGTTGGTGTA G　　101

( 2 ) INFORMATION FOR SEQ ID NO:64:

( i ) SEQUENCE CHARACTERISTICS:
    ( A ) LENGTH: 25 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:64:

GTCCAGCAGC ACCAGCTCTC CGGTC　　25

( 2 ) INFORMATION FOR SEQ ID NO:65:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:65:

GACCGGAGAG CTGGTGCTGC TGGACTGCA　　29

( 2 ) INFORMATION FOR SEQ ID NO:66:

( i ) SEQUENCE CHARACTERISTICS:
    ( A ) LENGTH: 26 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:66:

CGTCCAGCAG CACCAGCTCT CCGGTC　　26

( 2 ) INFORMATION FOR SEQ ID NO:67:

( i ) SEQUENCE CHARACTERISTICS:
    ( A ) LENGTH: 28 base pairs
    ( B ) TYPE: nucleic acid
    ( C ) STRANDEDNESS: double ( D ) TOPOLOGY: linear ( i i ) MOLECULE TYPE: DNA (genomic)

( x i ) SEQUENCE DESCRIPTION: SEQ ID NO:67:

GACCGGAGAG CTGGTGCTGC TGGACGAT 28

( 2 ) INFORMATION FOR SEQ ID NO:68:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

CGACAACATC ACATCAAGCT CTCC 24

( 2 ) INFORMATION FOR SEQ ID NO:69:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

CCATCCTTTA ACTATAGCGA 20

( 2 ) INFORMATION FOR SEQ ID NO:70:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

GCTGGTGCTG GTACCCGGGA TCTGGACGGC AGGG 34

( 2 ) INFORMATION FOR SEQ ID NO:71:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

GCATCGGTAC CGGCGGCGGC TCCACTGGCG 30

( 2 ) INFORMATION FOR SEQ ID NO:72:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

CTCACTCCAT CTCGAGTCTT TCAATTTACA 30

(2) INFORMATION FOR SEQ ID NO:73:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

CTTTTCTCGA GTCCCTTAGT TCAAGCACTG C 31

(2) INFORMATION FOR SEQ ID NO:74:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

TGACCGGTAC CGGCGGCGGC AACACCAACC 30

(2) INFORMATION FOR SEQ ID NO:75:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

TCACCGGTAC CGGCGGTGGA AGCAACAATG 30

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

TCTTCGGTAC CAGCGGCAAC AGCGGCGGCG 30

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

CGCTGGGTAC CAACAACAAT CCTCAGCAGG 30

(2) INFORMATION FOR SEQ ID NO:78:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:78:

CTCCCAGCAG CTGCACTGCT GAGAGGTGGG    30

( 2 ) INFORMATION FOR SEQ ID NO:79:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

CGGCCTCGAG ACCTTACAGG CACTGCGAGT    30

( 2 ) INFORMATION FOR SEQ ID NO:80:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

AATTCCGCGG AACGATATCT CCGA    24

( 2 ) INFORMATION FOR SEQ ID NO:81:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

GATCTCGGAG ATATACGTTC CGCGG    25

( 2 ) INFORMATION FOR SEQ ID NO:82:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

TTGAATTCTG ATCAAGATGC GTTCCTCCC    29

( 2 ) INFORMATION FOR SEQ ID NO:83:

( i ) SEQUENCE CHARACTERISTICS:
        ( A ) LENGTH: 42 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:83:

AATGGTGAAA GTGACATCAC TCCTGCCATC AGCGGCAAGG GC  42

( 2 ) INFORMATION FOR SEQ ID NO:84:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:84:

GCCCTTGCCG CTGATGGCAG GAGTGATGTC ACTTTCACCA TT  42

( 2 ) INFORMATION FOR SEQ ID NO:85:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:85:

AGCGCGTCCG CGGTAGCTAT G  21